United States Patent
Zheng et al.

(10) Patent No.: US 9,172,051 B2
(45) Date of Patent: Oct. 27, 2015

(54) ORGANIC LIGHT EMITTING HOST MATERIALS

(71) Applicant: Nitto Denko Corporation, Osaka (JP)

(72) Inventors: Shijun Zheng, San Deigo, CA (US);
David T. Sisk, San Diego, CA (US);
Liping Ma, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 13/971,081

(22) Filed: Aug. 20, 2013

(65) Prior Publication Data

US 2014/0066627 A1    Mar. 6, 2014

Related U.S. Application Data

(60) Provisional application No. 61/695,716, filed on Aug. 31, 2012.

(51) Int. Cl.
*C07D 401/14* (2006.01)
*H01L 51/00* (2006.01)
*C09K 11/06* (2006.01)
*H01L 51/50* (2006.01)

(52) U.S. Cl.
CPC .......... *H01L 51/0072* (2013.01); *C07D 401/14* (2013.01); *C09K 11/06* (2013.01); *H01L 51/006* (2013.01); *H01L 51/0061* (2013.01); *C09K 2211/1029* (2013.01); *C09K 2211/1044* (2013.01); *H01L 51/0037* (2013.01); *H01L 51/0052* (2013.01); *H01L 51/0067* (2013.01); *H01L 51/0085* (2013.01); *H01L 51/5016* (2013.01); *H01L 2251/308* (2013.01)

(58) Field of Classification Search
CPC ..................................................... C07D 401/14
USPC ........................................................ 546/256
See application file for complete search history.

(56) References Cited

PUBLICATIONS

Wang et al., "Carbazole and arylamine, etc.," Inorganica Chimica Acta 370 (2011) 340-345.*
Dorwald, Side Reactions in Organic Synthesis, 2005, Wiley: VCH Weinheim Preface, pp. 1-15 & Chapter 8, pp. 279-308.*

* cited by examiner

*Primary Examiner* — Patricia L Morris
(74) *Attorney, Agent, or Firm* — K&L Gates LLP; Louis C. Cullman; Brent A. Johnson

(57) ABSTRACT

Polyphenylene compounds such as compounds represented by Formulas 1-28 may be used in electronic devices such as organic light-emitting devices. For example, the compounds may be used as host material in an emissive layer.

12 Claims, 1 Drawing Sheet

ORGANIC LIGHT EMITTING HOST MATERIALS

CROSS REFERENCE TO RELATED APPLICATIONS

The present application claims the benefit under 35 U.S.C. §119(e) to U.S. Provisional Application Ser. No. 61/695,716 filed Aug. 31, 2012, the entire contents of all of which are hereby incorporated by reference in their entirety.

BACKGROUND

The embodiments disclosed herein include emissive compounds that can be used for light-emitting layers in devices.

Organic light-emitting devices (OLEDs) are becoming increasingly important in lighting and display applications. OLEDs may include an emissive or light-emitting layer that includes a host material and an emissive component dispersed within the host material. However, emissive material-containing OLED devices can have problems with low stability. These problems with emissive materials can contribute to low efficiency and a short lifetime of the devices comprising the emissive materials.

SUMMARY

Some embodiments include a compound represented by Formula 1:

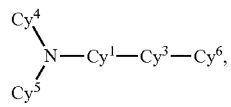

wherein $Cy^1$ is an optionally substituted p-phenylene; $Cy^3$ is an optionally substituted 2,3'-bipyridinyl, an optionally substituted 3,3'-bi-pyridinyl, or an optionally substituted 3,2':5',3''-terpyridinyl; $Cy^4$ and $Cy^5$ are optionally substituted phenyl or optionally substituted naphthyl; and, $Cy^6$ is optionally substituted 1-phenyl-1H-benzo[d]imidazol-2-yl.

Some embodiments include a compound represented by Formula 2:

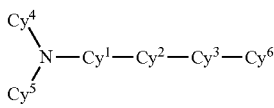

wherein $Cy^1$ and $Cy^2$ are independently p-phenylene optionally substituted with 1 or 2 substituents, wherein each substituent is independently $C_{1-6}$ alkyl or F, wherein $Cy^1$ and $Cy^2$ optionally link together to form a third ring; $Cy^3$ is independently an optionally substituted 2,5-pyridyl with 1, 2, or 3 substituents, an optionally substituted 2,3'-bipyridyl with 1, 2, or 3 substituents, or an optionally substituted 3,3-bipyridinyl with 1, 2, or 3 substituents, wherein each substituent is independently $C_{1-6}$ alkyl or F; $Cy^4$ and $Cy^5$ are optionally substituted phenyl or optionally substituted naphthyl; and, $Cy^6$ is 1-phenyl-1H-benzo[d]imidazol-2-yl optionally substituted with 1, 2, 3, 4, or 5 substituents, wherein each substituent is independently $C_{1-6}$ alkyl or F. In some embodiments, $Cy^3$ is independently an optionally substituted p-pyridinylene with 1, 2, or 3 substituents, an optionally substituted 2,3-bipyridyl with 1, 2, or 3 substituents, or an optionally substituted 3,3-bipyridinyl with 1, 2, or 3 substituents, wherein each substituent is independently $C_{1-6}$ alkyl or F.

Some embodiments include a compound represented by Formula 3:

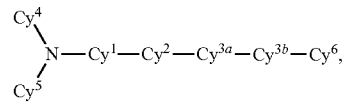

wherein $Cy^1$ is optionally substituted p-phenylene; $Cy^2$ is a bond, optionally substituted p-phenylene, or optionally substituted p-pyridinylene; wherein $Cy^1$ and $Cy^2$ can share a substituent that links $Cy^1$ and $Cy^2$ to form a fused ring system incorporating $Cy^1$ and $Cy^2$; $Cy^{3a}$ is optionally substituted p-pyridinylene; $Cy^{3b}$ is a bond or optionally substituted p-pyridinylene; $Cy^4$ and $Cy^5$ are independently optionally substituted phenyl or optionally substituted naphthyl; and, $Cy^6$ is optionally substituted benzimidazol-2-yl, optionally substituted benzoxazol-2-yl, or optionally substituted benzothiazol-2-yl.

Some embodiments include a compound represented by Formula 4:

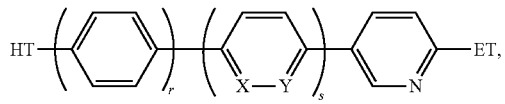

wherein HT is optionally substituted diphenylamine or optionally substituted phenylnaphthylamine; ET is optionally substituted benzimidazol-2-yl, optionally substituted benzoxazol-2-yl, or optionally substituted benzothiazol-2-yl; X is CH or N; Y is CH or N, provided that when X is N, Y is CH and when Y is N, X is CH; r is 1 or 2; and, s is 0 or 1, provided that when s is 0, r is 2.

With respect to Formula 4, in some embodiments HT is optionally substituted diphenylamine or an unsubstituted phenylnaphthylamine. In some embodiments, ET is an unsubstituted benzimidazol-2-yl.

Some embodiments include an emissive layer comprising a compound of any of Formulas 1-17; optionally substituted N,N-diphenyl-4-(6-(1-phenyl-1H-benzo[d]imidazol-2-yl)pyridin-3-yl)aniline; optionally substituted N-phenyl-N-(4'-(6-(1-phenyl-1H-benzo[d]imidazol-2-yl)pyridin-3-yl)-[1,1'-biphenyl]-4-yl)naphthalen-1-amine; optionally substituted 4'-(6'-(1-phenyl-1H-benzo[d]imidazol-2-yl)-[3,3'-bipyridin]-6-yl)-N,N-di-p-tolyl-[1,1'-biphenyl]-4-amine; optionally substituted 9,9-dimethyl-N,N-diphenyl-7-(6'-(1-phenyl-1H-benzo[d]imidazol-2-yl)-[3,3'-bipyridin]-6-yl)-9H-fluoren-2-amine; optionally substituted N,N-diphenyl-4'-(6'-(1-phenyl-1H-benzo[d]imidazol-2-yl)-[3,3'-bipyridin]-6-yl)-[1,1'-biphenyl]-4-amine; optionally substituted N,N-diphenyl-4'-(6'-(1-phenyl-1H-benzo[d]imidazol-2-yl)-[2,3'-bipyridin]-5-yl)-[1,1'-biphenyl]-4-amine; optionally substituted 4'-(3-methyl-6'-(1-phenyl-1H-benzo[d]imidazol-2-yl)-[2,3'-bipyridin]-5-yl)-N,N-diphenyl-[1,1'-biphenyl]-4-amine; optionally substituted N-phenyl-N-(4'-(6'-(1-phenyl-1H-benzo[d]imidazol-2-yl)-[2,3'-bipyridin]-5-yl)-[1,1'-biphenyl]-4-yl)naphthalen-2-amine; optionally substituted N-phenyl-N-(4'-(6'-(1-phenyl-1H-benzo[d]imidazol-2-yl)-[2,3'-bipyridin]-5-yl)-[1,1'-biphenyl]-4-yl)naphthalen-1-amine; optionally substituted N,N-diphenyl-4-(6-(1-phenyl- 1H-benzo[d]imidazol-2-yl)-[3,2':5',3"-terpyridin]-6"-yl)aniline; optionally substituted 4-methyl-N-(4-(6'-(1-phenyl-1H-benzo[d]imidazol-2-yl)-[3,3'-bipyridin]-6-yl)phenyl)-N-(p-tolyl)aniline; optionally substituted 4-methyl-N-(4-(6'-(1-phenyl-1H-benzo[d]imidazol-2-yl)-[2,3'-bipyridin]-5-yl)phenyl)-N-(p-tolyl)aniline; optionally substituted N-phenyl-N-(4-(6'-(1-phenyl-1H-benzo[d]imidazol-2-yl)-[3,3'-bipyridin]-6-yl)phenyl)naphthalen-1-amine; or, optionally substituted 9,9-dimethyl-7-(6'-(1-phenyl-1H-benzo[d]imidazol-2-yl)-[3,3'-bipyridin]-6-yl)-N,N-di-p-tolyl-9H-fluoren-2-amine.

Some embodiments provide a compound described herein in an emissive layer. Some embodiments include a light-emitting device comprising a compound described herein. Some embodiments provide a light-emitting device comprising the emissive layer described herein.

These and other embodiments are described in more detail herein.

DETAILED DESCRIPTION

Figure 1:
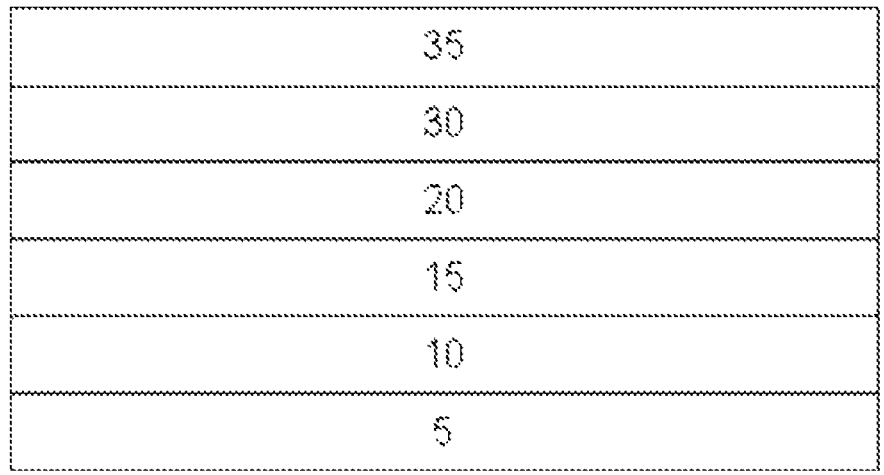
FIG. 1 is a schematic drawing of an embodiment of an OLED device comprising a compound disclosed herein.

By employing a newly designed molecular structure, embodiments of which are demonstrated in Examples below, a new series of host materials is produced that can be used in OLED device applications. The synthesis of this series of host materials is straightforward and results in a high yield.

Unless otherwise indicated, when a compound or chemical structural feature such as aryl is referred to as being "optionally substituted," it is meant that the feature may have no substituents (i.e., unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g., the sum of the atomic masses of the atoms of the substituent) of 15 g/mol to 50 g/mol, 15 g/mol to 100 g/mol, 15 g/mol to 200 g/mol, 15 g/mol to 300 g/mol, or 15 g/mol to 500 g/mol. In some embodiments, the substituent comprises, or consists of, 0-30, 0-20, 0-10, or 0-5 carbon atoms, and 0-30, 0-20, 0-10, or 0-5 heteroatoms independently selected from N, O, S, Si, F, Cl, Br, or I; provided that the substituent comprises at least one atom selected from C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, etc. In some embodiments, two substituents may combine to form a ring.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by |, attachment may occur at any position normally occupied by a hydrogen atom.

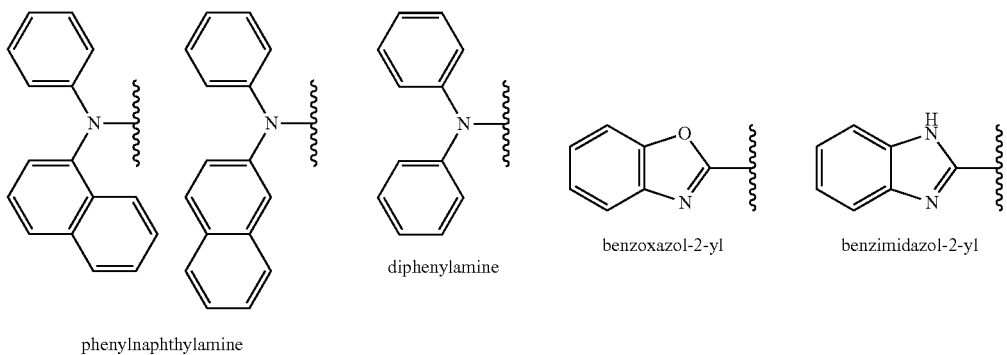

phenylnaphthylamine     diphenylamine     benzoxazol-2-yl     benzimidazol-2-yl

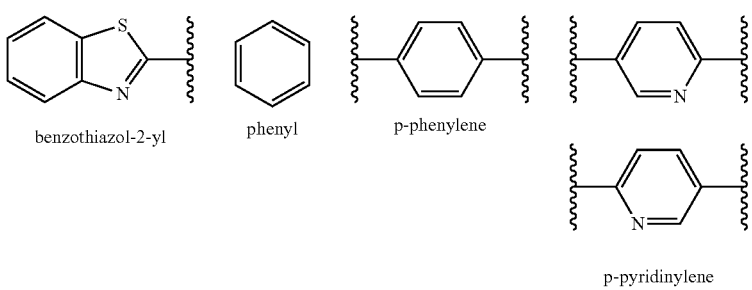

benzothiazol-2-yl     phenyl     p-phenylene p-pyridinylene

-continued naphthyl naphth-1-yl naphth-2-yl bipyridinyl 2,3'-bipyridinyl 3,3'-bipyridinyl 3,2':5', 3"-terpyridinyl 1-phenyl-1H-benzo[d]imidazol-2-yl

BE-1

N,N-diphenyl-4-(6-(1-phenyl-1H-benzo[d]imidazol-2-yl)pyridin-3-yl)aniline,

BE-2

N-phenyl-N-(4'-(6-(1-phenyl-1H-benzo[d]imidazol-2-yl)pyridin-3-yl)-[1,1'-biphenyl]-4-yl)naphthanen-1-amine, -continued
BE-3
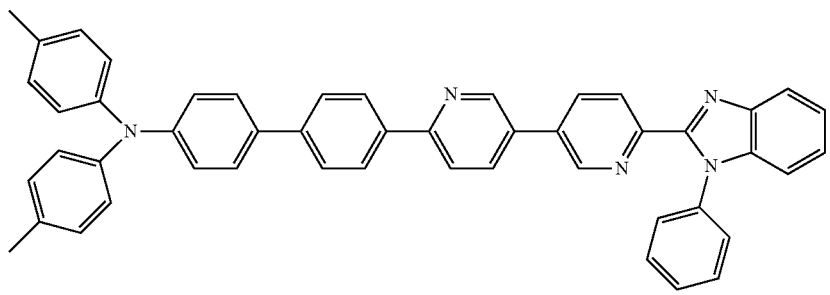
4'-(6'-(1-phenyl-1H-benzo[d]imidazol-2-yl)-[3,3'-bipyridin]-6-yl)-N,N-di-p-tolyl-[1,1'-biphenyl]-4-amine,
BE-4
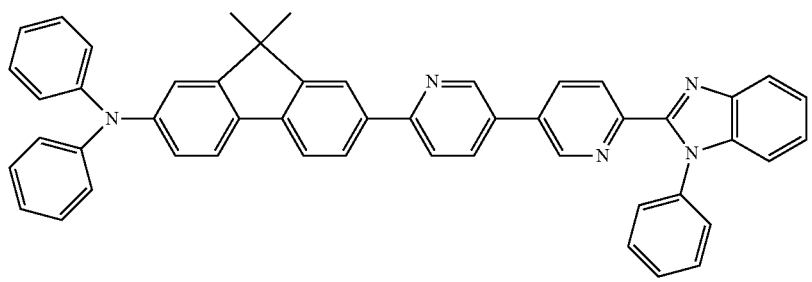
9,9-dimethyl-N,N-diphenyl-7-(6'-(1-phenyl-1H-benzo[d]imidazol-2-yl)-[3,3'-bipyridin]-6-yl)-9H-fluoren-2-amine,
BE-5
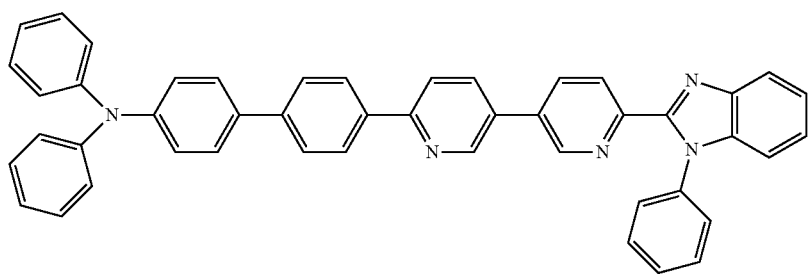
N,N-diphenyl-4'-(6'-(1-phenyl-1H-benzo[d]imidazol-2-yl)-[3,3'-bipyridin]-6-yl)-[1,1'-biphenyl]-4-amine,
BE-6
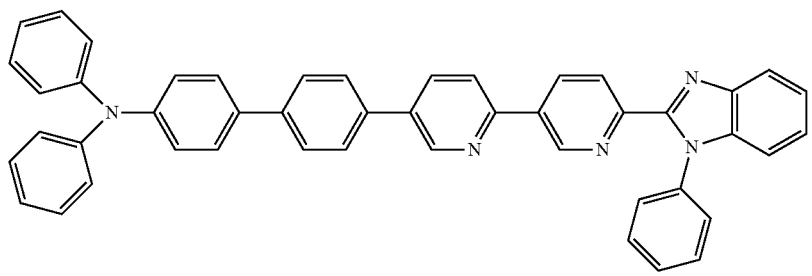
N,N-diphenyl-4'-(6'-(1-phenyl-1H-benzo[d]imidazol-2-yl)-[2,3'-bipyridin]-5-yl)-[1,1'-biphenyl]-4-amine, BE-7
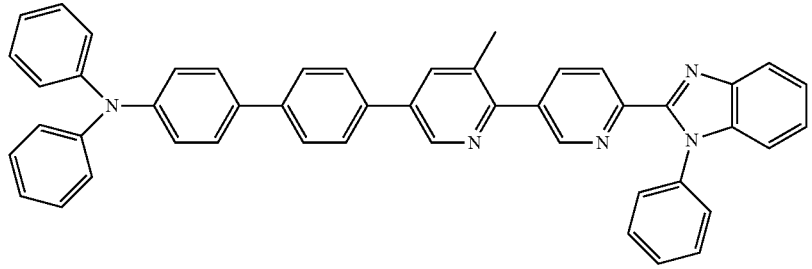
4'-(3-methyl-6'-(1-phenyl-1H-benzo[d]imidazol-2-yl)-[2,3'-bipyridin]-5-yl)-N,N-diphenyl-[1,1'-biphenyl]-4-amine,
BE-8
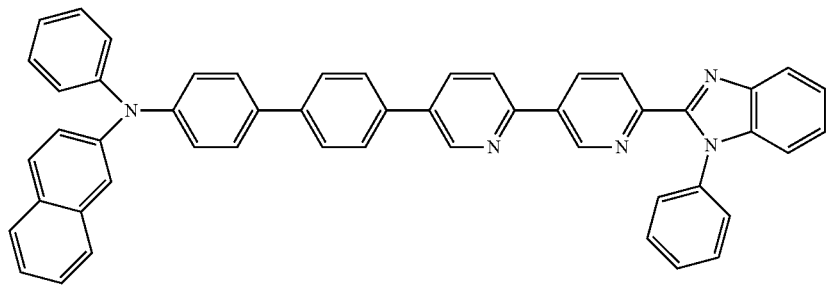
N-phenyl-N-(4'-(6'-(1-phenyl-1H-benzo[d]imidazol-2-yl)-[2,3'-bipyridin]-5-yl)-[1,1'-biphenyl]-4-yl)naphthalen-2-amine,
BE-9
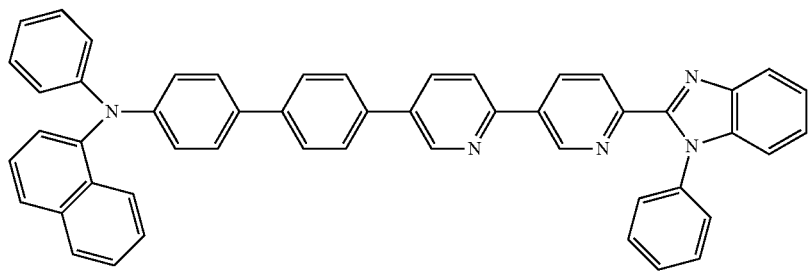
N-phenyl-N-(4'-(6'-(1-phenyl-1H-benzo[d]imidazol-2-yl)-[2,3'-bipyridin]-5-yl)-[1,1'-biphenyl]-4-yl)naphthalen-1-amine,
BE-10
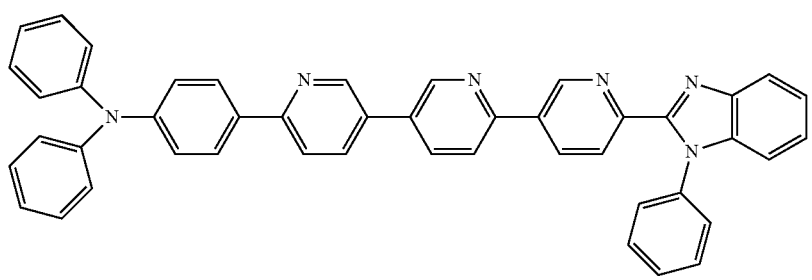
N,N-diphenyl-4-(6-(1-phenyl-1H-benzo[d]imidazol-2-yl)-[3,2':5',3''-terpyridin]-6''-yl)aniline, -continued
BE-11
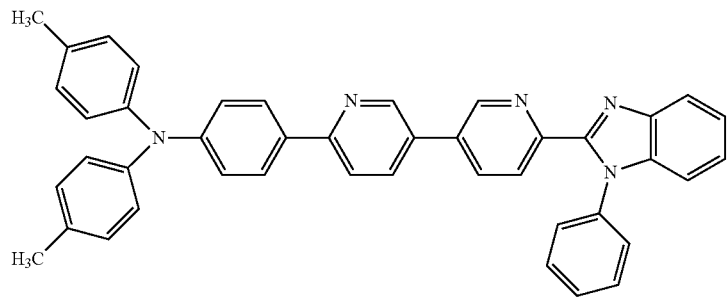
4-methyl-N-(4-(6'-(1-phenyl-1H-benzo[d]imidazol-2-yl)-[3,3'-bipyridin]-6-yl)phenyl)-N-(p-tolyl)aniline,
BE-12
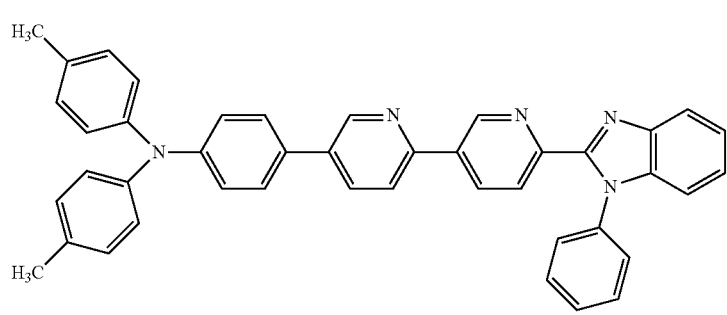
4-methyl-N-(4-(6'-(1-phenyl-1H-benzo[d]imidazol-2-yl)-[2,3'-bipyridin]-5-yl)phenyl)-N-(p-tolyl)aniline,
BE-13
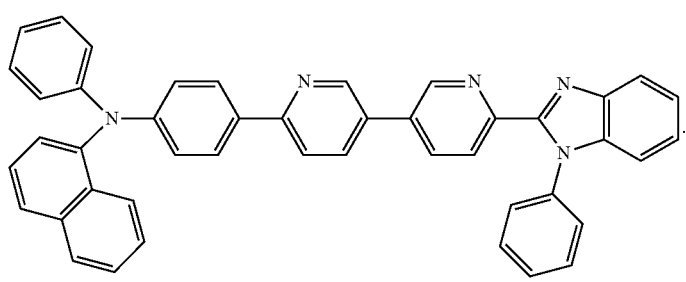
N-phenyl-N-(4-(6'-(1-phenyl-1H-benzo[d]imidazol-2-yl)-[3,3'-bipyridin]-6-yl)phenyl)naphthalen-1-amine, or
BE-14
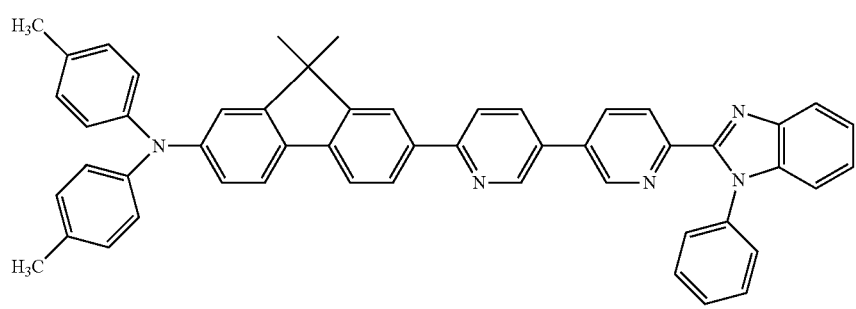
9,9-dimethyl-7-(6'-(1-phenyl-1H-benzo[d]imidazol-2-yl)-[3,3'-bipyridin]-6-yl)-N,N-di-*p*-tolyl-9H-fluoren-2-amine Some embodiments herein comprise optionally substituted N,N-diphenyl-4-(6-(1-phenyl-1H-benzo[d]imidazol-2-yl)pyridin-3-yl)aniline (BE-1); optionally substituted N-phenyl-N-(4'-(6-(1-phenyl-1H-benzo[d]imidazol-2-yl)pyridin-3-yl)-[1,1'-biphenyl]-4-yl)naphthalen-1-amine (BE-2); optionally substituted 4'-(6'-(1-phenyl-1H-benzo[d]imidazol-2-yl)-[3,3'-bipyridin]-6-yl)-N,N-di-p-tolyl-[1,1'-biphenyl]-4-amine (BE-3); optionally substituted 9,9-dimethyl-N,N-diphenyl-7-(6'-(1-phenyl-1H-benzo[d]imidazol-2-yl)-[3,3'-bipyridin]-6-yl)-9H-fluoren-2-amine (BE-4); optionally substituted N,N-diphenyl-4'-(6'-(1-phenyl-1H-benzo[d]imidazol-2-yl)-[3,3'-bipyridin]-6-yl)-[1,1'-biphenyl]-4-amine (BE-5); optionally substituted N,N-diphenyl-4'-(6'-(1-phenyl-1H-benzo[d]imidazol-2-yl)-[2,3'-bipyridin]-5-yl)-[1,1'-biphenyl]-4-amine (BE-6); optionally substituted 4'-(3-methyl-6'-(1-phenyl-1H-benzo[d]imidazol-2-yl)-[2,3'-bipyridin]-5-yl)-N,N-diphenyl-[1,1'-biphenyl]-4-amine (BE-7); optionally substituted N-phenyl-N-(4'-(6'-(1-phenyl-1H-benzo[d]imidazol-2-yl)-[2,3'-bipyridin]-5-yl)-[1,1'-biphenyl]-4-yl)naphthalen-2-amine (BE-8); optionally substituted N-phenyl-N-(4'-(6'-(1-phenyl-1H-benzo[d]imidazol-2-yl)-[2,3'-bipyridin]-5-yl)-[1,1'-biphenyl]-4-yl)naphthalen-1-amine (BE-9); optionally substituted N,N-diphenyl-4-(6-(1-phenyl-1H-benzo[d]imidazol-2-yl)-[3,2':5',3"-terpyridin]-6"-yl)aniline (BE-10); optionally substituted 4-methyl-N-(4-(6'-(1-phenyl-1H-benzo[d]imidazol-2-yl)-[3,3'-bipyridin]-6-yl)phenyl)-N-(p-tolyl)aniline (BE-11); optionally substituted 4-methyl-N-(4-(6'-(1-phenyl-1H-benzo[d]imidazol-2-yl)-[2,3'-bipyridin]-5-yl)phenyl)-N-(p-tolyl)aniline (BE-12); optionally substituted N-phenyl-N-(4-(6'-(1-phenyl-1H-benzo[d]imidazol-2-yl)-[3,3'-bipyridin]-6-yl)phenyl)naphthalen-1-amine (BE-13); or, optionally substituted 9,9-dimethyl-7-(6'-(1-phenyl-1H-benzo[d]imidazol-2-yl)-[3,3'-bipyridin]-6-yl)-N,N-di-p-tolyl-9H-fluoren-2-amine (BE-14).

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—$CH_3$), ethyl (—$CH_2CH_3$), n-propyl (—$CH_2CH_2CH_3$), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g., iso-propyl), $C_4H_9$ (e.g., branched butyl isomers), $C_5H_{11}$ (e.g., branched pentyl isomers), $C_6H_{13}$ (e.g., branched hexyl isomers), $C_7H_{15}$ (e.g., heptyl isomers), etc.; $C_{3-10}$ cycloalkyl, such as $C_3H_5$ (e.g., cyclopropyl), $C_4H_7$ (e.g., cyclobutyl isomers such as cyclobutyl, methylcyclopropyl, etc.), $C_5H_9$ (e.g., cyclopentyl isomers such as cyclopentyl, methylcyclobutyl, dimethylcyclopropyl, etc.), $C_6H_{11}$ (e.g., cyclohexyl isomers), $C_7H_{13}$ (e.g., cycloheptyl isomers), etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. A phrase such as "$C_{1-12}$ optionally substituted alkyl" refers to unsubstituted $C_{1-12}$ alkyl, or substituted alkyl wherein both the alkyl parent and all substituents have from 1-12 carbon atoms. Similar conventions may be applied to other optionally substituted moieties such as aryl and heteroaryl.

Substituents on alkyl may be the same as those described generally above, except that alkyl may not have an alkyl substituent. In some embodiments, substituents on alkyl are independently selected from F, Cl, Br, I, CN, $CO_2H$, —O-alkyl, ester groups, acyl, amine groups, and amide groups, and may have a molecular weight of about 15 to about 100 or about 500.

The term "perfluoroalkyl" refers to fluoroalkyl with a formula $C_nF_{2n}$—$F_1$ for a linear or branched structure. Perfluoroalkyl can be, for example: $CF_3$, $C_2F_5$, $C_3F_7$, $C_4F_9$, $C_5F_{11}$, $C_6F_{13}$, etc.; or, $C_nF_{2n}$ for a cyclic structure, e.g., cyclic $C_3F_6$, cyclic $C_4F_8$, cyclic $C_5F_{10}$, cyclic $C_6F_{12}$, etc. In other words, every hydrogen atom in the alkyl is replaced by fluorine. For example, $C_{1-3}$ perfluoroalkyl refers to $CF_3$, $C_2F_5$, and $C_3F_7$ isomers.

As used herein the term "aryl" has the broadest meaning generally understood in the art, and may include an aromatic ring or aromatic ring system such as phenyl, naphthyl, etc. The term "heteroaryl" also has the meaning understood by a person of ordinary skill in the art, and includes an "aryl" which has one or more heteroatoms in the ring or ring system, such as pyridinyl, furyl, thienyl, oxazolyl, thiazolyl, imidazolyl, indolyl, quinolinyl, benzofuranyl, benzothienyl, benzoxazolyl, benzothiazolyl, benzimidazolyl, etc.

If stereochemistry is not indicated, a name or structural depiction includes any stereoisomer or any mixture of stereoisomers.

With respect to any relevant formula or structural depiction herein, HT can be optionally substituted diphenylamine or optionally substituted phenylnaphthylamine. If HT is substituted, it may have 1, 2, 3, 4, 5, or more, substituents. Any substituent may be included on HT. In some embodiments, some or all of the substituents on HT may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy, such as —$OCH_3$, —$OC_2H_5$, —$OC_3H_7$, cyclic —$OC_3H_5$, —$OC_4H_9$, cyclic —$OC_4H_7$, —$CO_5H_{11}$, cyclic —$CO_5H_9$, —$OC_6H_{13}$, cyclic —$OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, HT is unsubstituted. In some embodiments, HT may have 0, 1, 2, 3, or 4 electron-donating substituents, such as $C_{1-6}$ alkyl, OH, $C_{1-6}$ alkoxy, or a $C_{1-10}$ amine. In some embodiments, HT is unsubstituted, or any substituents of HT are independently F, methyl, ethyl, propyl, or isopropyl.

With respect to any relevant formula or structural depiction herein, ET can be optionally substituted benzimidazol-2-yl, optionally substituted benzoxazol-2-yl, or optionally substituted benzothiazol-2-yl. If ET is substituted, it may have 1, 2, 3, 4, 5, or more substituents. Any substituent may be included on ET. In some embodiments, some or all of the substituents on ET may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, ET is unsubstituted. With respect to any relevant formula or structural depiction herein, $Cy^1$ can be optionally substituted p-phenylene. If the p-phenylene is substituted, it may have 1, 2, 3, or 4 substituents. Any substituent may be included on the p-phenylene. In some embodiments, some or all of the substituents on the p-phenylene may have: from 0 to 10 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the p-phenylene is optionally substituted with 1 or 2 substituents independently selected from $C_{1-6}$ alkyl and F. In some embodiments, $Cy^1$ is unsubstituted.

With respect to any relevant formula or structural depiction herein, $Cy^2$ can be a bond.

With respect to any relevant formula or structural depiction herein, $Cy^2$ can be optionally substituted p-phenylene. If the p-phenylene is substituted, it may have 1, 2, 3, or 4 substituents. Any substituent can be included on the p-phenylene. In some embodiments, some or all of the substituents on the p-phenylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the p-phenylene is optionally substituted with 1 or 2 substituents independently selected from $C_{1-6}$ alkyl and F. If the p-phenylene is substituted, it may have 1, 2, 3, or 4 substituents.

With respect to any relevant formula or structural depiction herein, $Cy^2$ can be optionally substituted p-pyridinylene. Any substituent can be included on the p-pyridinylene. In some embodiments, some or all of the substituents on the p-pyridinylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the p-pyridinylene is optionally substituted with 1 or 2 substituents independently selected from $C_{1-6}$ alkyl and F.

In some embodiments, $Cy^2$ is unsubstituted.

With respect to any relevant formula or structural depiction herein, $Cy^1$ and $Cy^2$ can share a substituent that links $Cy^1$ and $Cy^2$ to form a fused ring system incorporating $Cy^1$ and $Cy^2$.

With respect to any relevant formula or structural depiction herein, $Cy^3$ can be optionally substituted p-pyridinylene. Any substituent can be included on the p-pyridinylene. In some embodiments, some or all of the substituents on the p-pyridinylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the p-pyridinylene is optionally substituted with 1 or 2 substituents independently selected from $C_{1-6}$ alkyl and F.

With respect to any relevant formula or structural depiction herein, $Cy^3$ can be optionally substituted 2,3-bipyridinyl. Any substituent can be included on the 2,3-bipyridinyl. In some embodiments, some or all of the substituents on the 2,3-bipyridinyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the 2,3-bipyridinyl is optionally substituted with 1 or 2 substituents independently selected from $C_{1-6}$ alkyl and F.

With respect to any relevant formula or structural depiction herein, $Cy^3$ can be optionally substituted 3,3-bipyridinyl. Any substituent can be included on the 3,3-bipyridinyl. In some embodiments, some or all of the substituents on the 3,3-bipyridinyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, the 3,3-bipyridinyl is optionally substituted with 1 or 2 substituents independently selected from $C_{1-6}$ alkyl and F.

In some embodiments, $Cy^3$ is unsubstituted.

With respect to any relevant formula or structural depiction herein, $Cy^{3a}$ can be optionally substituted p-pyridinylene.

Any substituent can be included on the p-pyridinylene. In some embodiments, some or all of the substituents on the p-pyridinylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the p-pyridinylene is optionally substituted with 1 or 2 substituents independently selected from $C_{1-6}$ alkyl and F. In some embodiments, $Cy^{3a}$ is unsubstituted.

With respect to any relevant formula or structural depiction herein, $Cy^{3b}$ can be a bond.

With respect to any relevant formula or structural depiction herein, $Cy^{3b}$ can be optionally substituted p-pyridinylene. Any substituent can be included on the p-pyridinylene. In some embodiments, some or all of the substituents on the p-pyridinylene may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the p-pyridinylene is optionally substituted with 1 or 2 substituents independently selected from $C_{1-6}$ alkyl and F. In some embodiments, $Cy^{3b}$ is unsubstituted.

With respect to any relevant formula or structural depiction herein, $Cy^4$ can be optionally substituted phenyl. Any substituent can be included on the phenyl. In some embodiments, some or all of the substituents on the phenyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1, 2, 3, 4 or 5 substituents independently selected from $C_{1-6}$ alkyl and F. In some embodiments, the phenyl may have 0, 1, 2, 3, or 4 electron-donating substituents, such as $C_{1-6}$ alkyl, OH, $C_{1-6}$ alkoxy, or a $C_{1-10}$ amine. In some embodiments, the phenyl is unsubstituted, or any substituents of the phenyl are independently F, methyl, ethyl, propyl, or isopropyl.

With respect to any relevant formula or structural depiction herein, $Cy^4$ can be optionally substituted naphthyl. Any substituent can be included on the naphthyl. In some embodiments, some or all of the substituents on the naphthyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the naphthyl is optionally substituted with 1, 2, 3, 4, 5, 6 or 7 substituents independently selected from $C_{1-6}$ alkyl and F. In some embodiments, the naphthyl may have 0, 1, 2, 3, or 4 electron-donating substituents, such as $C_{1-6}$ alkyl, OH, $C_{1-6}$ alkoxy, or a $C_{1-10}$ amine. In some embodiments, the naphthyl is unsubstituted, or any substituents of the naphthyl are independently F, methyl, ethyl, propyl, or isopropyl.

In some embodiments, $Cy^4$ is unsubstituted.

With respect to any relevant formula or structural depiction herein, $Cy^5$ can be optionally substituted phenyl. Any substituent can be included on the phenyl. In some embodiments, some or all of the substituents on the phenyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the phenyl is optionally substituted with 1, 2, 3, 4 or 5 substituents independently selected from $C_{1-6}$ alkyl and F. In some embodiments, the phenyl may have 0, 1, 2, 3, or 4 electron-donating substituents, such as $C_{1-6}$ alkyl, OH, $C_{1-6}$ alkoxy, or a $C_{1-10}$ amine. In some embodiments, the phenyl is unsubstituted, or any substituents of the phenyl are independently F, methyl, ethyl, propyl, or isopropyl.

With respect to any relevant formula or structural depiction herein, $Cy^5$ can be optionally substituted naphthyl. Any substituent can be included on the naphthyl. In some embodiments, some or all of the substituents on the naphthyl may have: from 0 to 15 carbon atoms and from 0 to 10 heteroatoms independently selected from: O, N, S, F, Cl, Br, and I; and/or a molecular weight of 15 g/mol to 500 g/mol. For example, the substituents may be $C_{1-10}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc.; $C_{1-10}$ alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —$CO$-phenyl, etc.; or a $C_{1-10}$ amine such as $NH_2$, $NH(CH_3)$, $N(CH_3)_2$, $N(CH_3)C_2H_5$, etc. In some embodiments, the naphthyl is optionally substituted with 1, 2, 3, 4, 5, 6 or 7 substituents independently selected from $C_{1-6}$ alkyl and F. In some embodiments, the naphthyl may have 0, 1, 2, 3, or 4 electron-donating substituents, such as $C_{1-6}$ alkyl, OH, $C_{1-6}$ alkoxy, or a $C_{1-10}$ amine. In some embodiments, the naphthyl is unsubstituted, or any substituents of the naphthyl are independently F, methyl, ethyl, propyl, or isopropyl.

In some embodiments, Cy$^5$ is unsubstituted.

With respect to any relevant formula or structural depiction herein, Cy$^6$ can be optionally substituted benzimidazol-2-yl, optionally substituted benzothiazol-2-yl, or optionally substituted benzoxazol-2-yl.

In some embodiments Cy$^6$ may be optionally substituted. If Cy$^6$ is substituted, it may have 1, 2, 3, 4, or 5 substituents. Any substituent may be included on Cy$^6$. In some embodiments, some or all of the substituents on Cy$^6$ may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. For example, the substituents may independently be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy; halo, such as F, Cl, Br, I; OH; CN; $NO_2$; $C_{1-6}$ fluoroalkyl, such as $CF_3$, $CF_2H$, $C_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$-phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, Cy$^6$ is unsubstituted. In some embodiments, Cy$^6$ may have 0, 1, 2, 3, 4, 5, or 6 electron-withdrawing substituents, such as F, $C_{1-6}$ perfluoroalkyl, $NO_2$, CN, etc. In some embodiments, Cy$^6$ is unsubstituted, or any substituents of Cy$^6$ are independently F or $C_{1-3}$ alkyl.

In some embodiments, HT can be

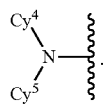

In some embodiments, HT can be:

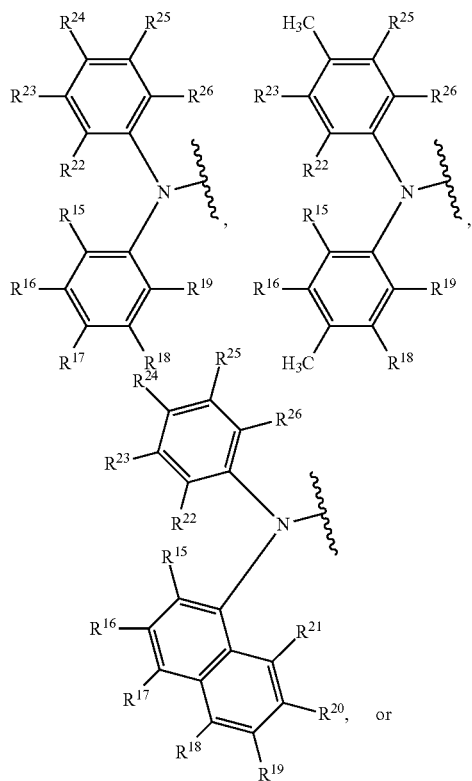

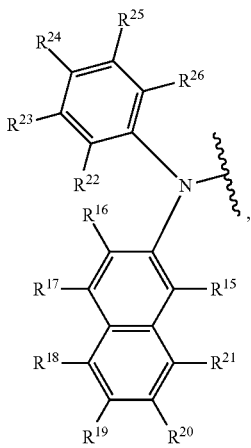

wherein $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently H or any substituent. In some embodiments, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently H, F, or $C_{1-3}$ alkyl. In some embodiments, HT can be:

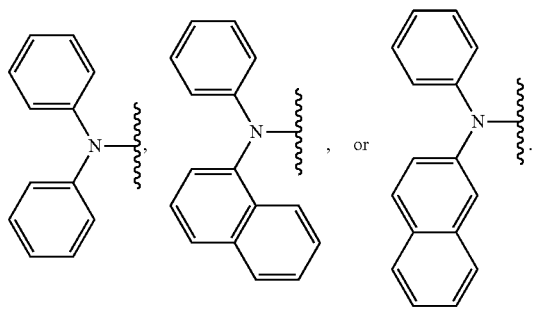

In some embodiments, ET can be Cy$^6$. In some embodiments, ET can be:

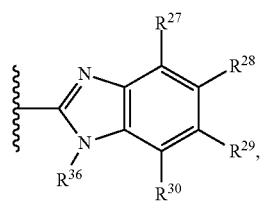

wherein $R^{27}$, $R^{28}$, $R^{28}$, $R^{30}$, and $R^{36}$ are independently H or any substituent. In some embodiments, $R^{27}$, $R^{28}$, $R^{28}$, and $R^{30}$ are independently H or any electron-withdrawing substituent, such as F, $C_{1-6}$ perfluoroalkyl, $NO_2$, CN, etc. In some embodiments, $R^{27}$, $R^{28}$, $R^{28}$, and $R^{30}$ are independently H, F or $C_{1-3}$ alkyl. In some embodiments $R^{27}$, $R^{28}$, $R^{28}$, and $R^{30}$ are independently H, F, $C_{1-3}$ alkyl, or $C_{1-3}$ perfluoroalkyl. In some embodiments, $R^{36}$ is H, $C_{1-3}$ alkyl, $C_{1-3}$ perfluoroalkyl, or optionally substituted phenyl. In some embodiments, ET can be:

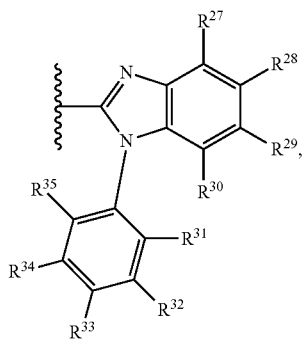

wherein $R^{27}$, $R^{28}$, $R^{29}$, $R^{30}$, $R^{31}$, $R^{32}$, $R^{33}$, $R^{34}$, and $R^{35}$ are independently H, F, methyl, ethyl, propyl, or isopropyl. In some embodiments, ET can be:

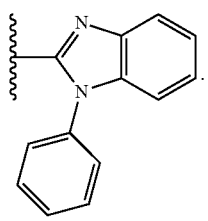 [SMILES: *c1nc2ccccc2n1-c1ccccc1]

In some embodiments, $Cy^1$ can be:

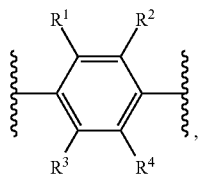

wherein $R^1$, $R^2$, $R^3$, and $R^4$ are independently H or any substituent. In some embodiments, $R^1$, $R^2$, $R^3$, and $R^4$ are independently H, F, or $C_{1-3}$ alkyl. In some embodiments, $R^1$, $R^2$, $R^3$, and $R^4$ are independently H, F, methyl, ethyl, propyl, or isopropyl.

In some embodiments, $Cy^2$ can be a bond. In some embodiments, $Cy^2$ can be:

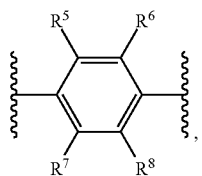

wherein $R^5$, $R^6$, $R^7$, and $R^8$ are independently H or any substituent. In some embodiments, $R^5$, $R^6$, $R^7$, and $R^8$ are independently H, F, or $C_{1-3}$ alkyl.

In some embodiments, $Cy^2$ can be:

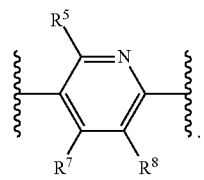

In some embodiments, $Cy^1$ and $Cy^2$ can be:

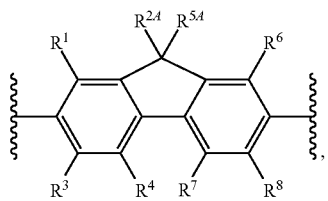

wherein $R^{2A}$ and $R^{5A}$ are independently H or any substituent. In some embodiments, $R^{2A}$ and $R^{5A}$ are independently H, F, or $C_{1-3}$ alkyl.

In some embodiments, $Cy^3$ can be:

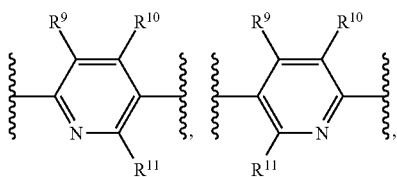

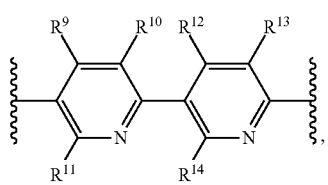

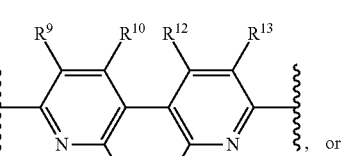

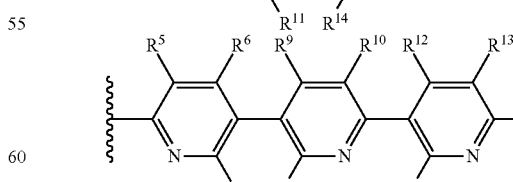

wherein $R^5$, $R^6$, $R^7$, $R^8$, $R^9$, $R^{10}$, $R^{11}$, $R^{12}$, $R^{13}$, and $R^{14}$ are independently H or any substituent. In some embodiments, $R^5$, $R^6$, $R^7$, $R^8$, $R^9$, $R^{10}$, $R^{11}$, $R^{12}$, $R^{13}$, and $R^{14}$ are independently H, F, or $C_{1-3}$ alkyl.

In some embodiments, $Cy^{3a}$ can be:

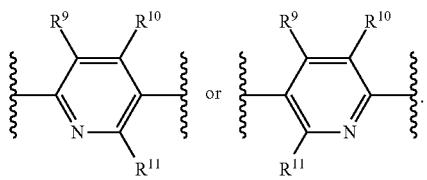

In some embodiments, $Cy^{3b}$ can be:

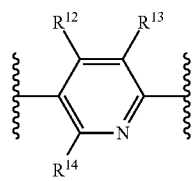

wherein $R^9$, $R^{10}$, $R^{11}$, $R^{12}$, $R^{13}$, and $R^{14}$ are independently H or any substituent. In some embodiments, $R^9$, $R^{10}$, $R^{11}$, $R^{12}$, and $R^{14}$ are independently H, F, or $C_{1-3}$ alkyl.

In some embodiments, $Cy^4$ can be:

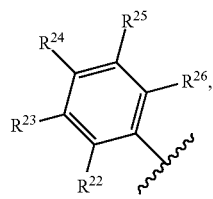

wherein $R^{22}$, $R^{23}$, $R^{24}$, $R^{25}$ and $R^{26}$ are independently H or any substituent. In some embodiments, $R^{29}$, $R^{39}$, $R^{31}$, $R^{32}$ and $R^{33}$ are independently H, F, $C_{1-3}$ alkyl, or $C_{1-3}$ perfluoroalkyl. In some embodiments, $R^{29}$, $R^{30}$, $R^{31}$, $R^{32}$ and $R^{33}$ are independently H, F, or $C_{1-3}$ alkyl.

In some embodiments, $Cy^5$ can be:

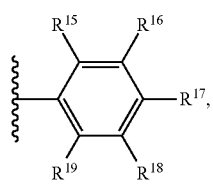

wherein $R^{15}$, $R^{16}$, $R^{17}$, $R^{18}$, and $R^{19}$ are independently H or any substituent. In some embodiments $R^{15}$, $R^{16}$, $R^{17}$, $R^{18}$, and $R^{19}$ are independently H, F, $C_{1-3}$ alkyl, or $C_{1-3}$ perfluoroalkyl.

In some embodiments $R^{15}$, $R^{16}$, $R^{17}$, $R^{18}$, and $R^{19}$ are independently H, F, or $C_{1-3}$ alkyl.

In some embodiments, $Cy^5$ can be:

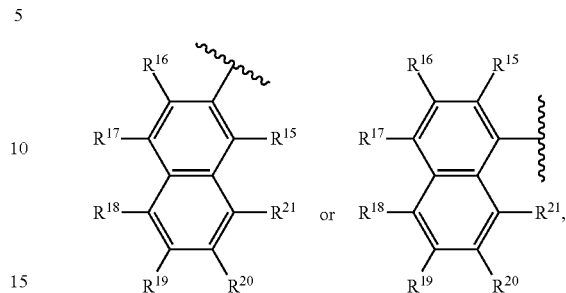

wherein $R^{15}$, $R^{16}$, $R^{17}$, $R^{18}$, $R^{19}$, $R^{20}$, and $R^{21}$ are independently H or any substituent. In some embodiments $R^{15}$, $R^{16}$, $R^{17}$, $R^{18}$, $R^{19}$, $R^{20}$, and $R^{21}$ are independently H, F, $C_{1-3}$ alkyl, or $C_{1-3}$ perfluoroalkyl. In some embodiments $R^{15}$, $R^{16}$, $R^{17}$, $R^{18}$, $R^{19}$, $R^{20}$, and $R^{21}$ are independently H, F, or $C_{1-3}$ alkyl.

In some embodiments, $Cy^6$ can be:

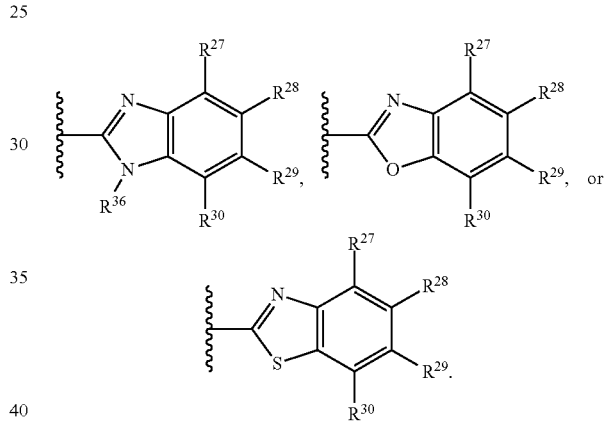

wherein $R^{27}$, $R^{28}$, $R^{28}$, and $R^{30}$, and $R^{36}$ are independently H or any substituent. In some embodiments, $R^{27}$, $R^{28}$, $R^{28}$, and $R^{30}$ are independently H or any electron-withdrawing substituent, such as F, $C_{1-6}$ perfluoroalkyl, $NO_2$, CN, etc. In some embodiments, $R^{27}$, $R^{28}$, $R^{28}$, and $R^{30}$ are independently H, F or $C_{1-3}$ alkyl. In some embodiments $R^{27}$, $R^{28}$, $R^{28}$, and $R^{30}$ are independently H, F, $C_{1-3}$ alkyl, or $C_{1-3}$ perfluoroalkyl. In some embodiments, $R^{36}$ is H, $C_{1-3}$ alkyl, $C_{1-3}$ perfluoroalkyl, or optionally substituted phenyl.

Some embodiments can include a compound represented by one or more of Formulas 5-28, as follows:

Formula 5

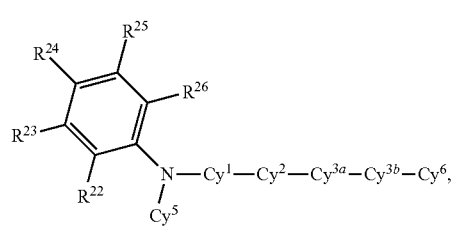

Formula 6

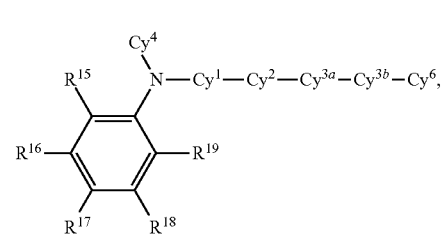

-continued
Formula 7
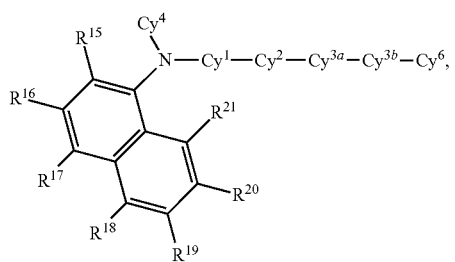
Formula 8
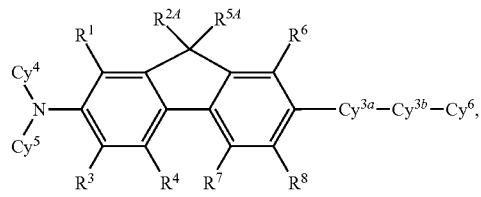
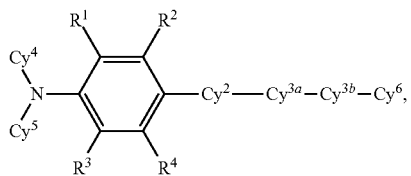
Formula 9
Formula 10
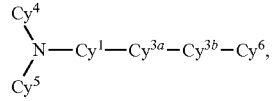
Formula 11
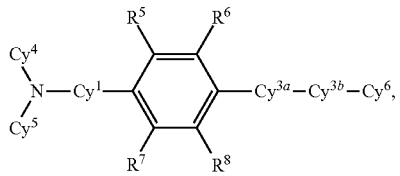
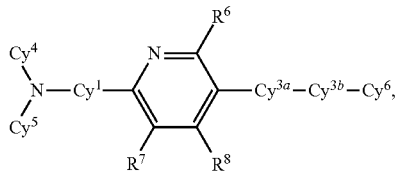
Formula 12
Formula 13
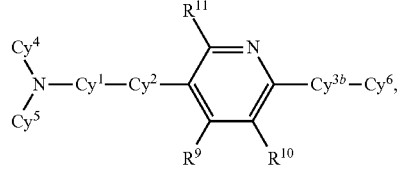
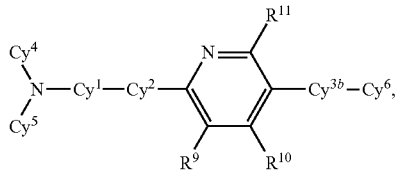
Formula 14
Formula 15
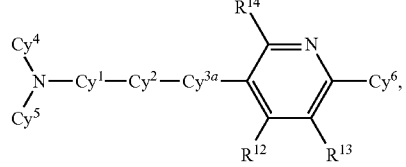
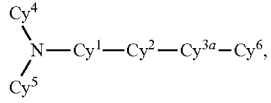
Formula 16
Formula 17
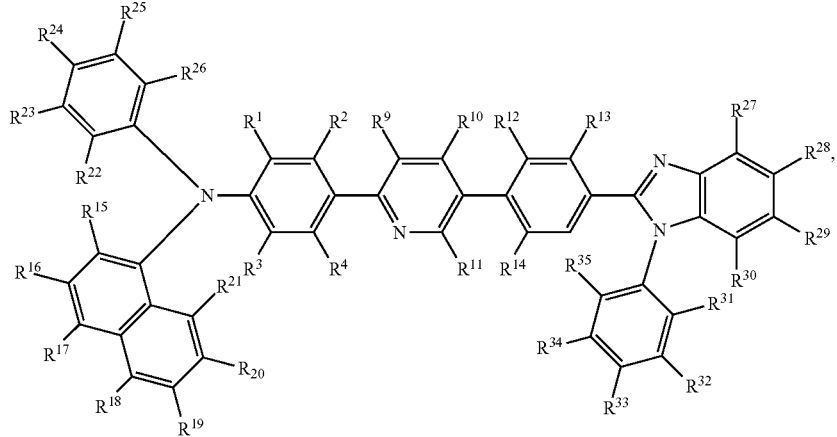
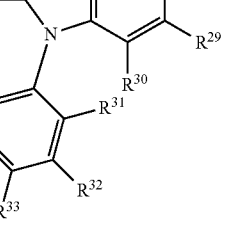

Formula 18
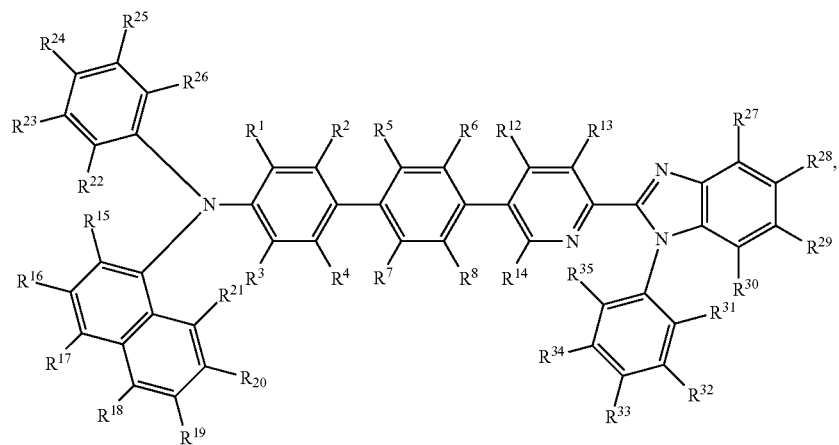
Formula 19
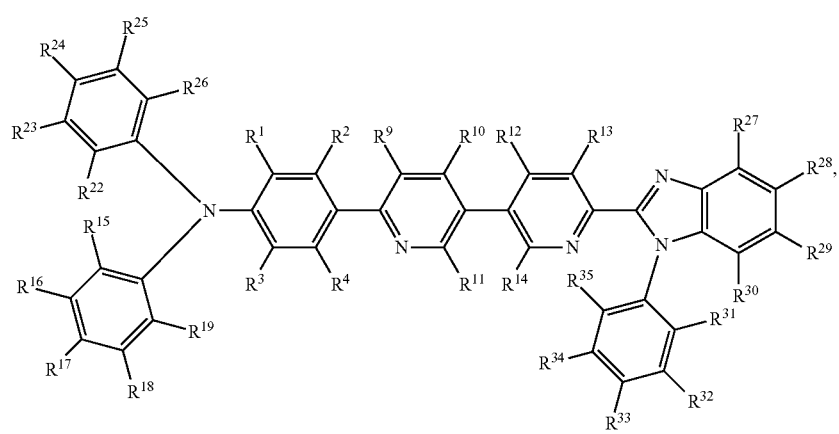
Formula 20
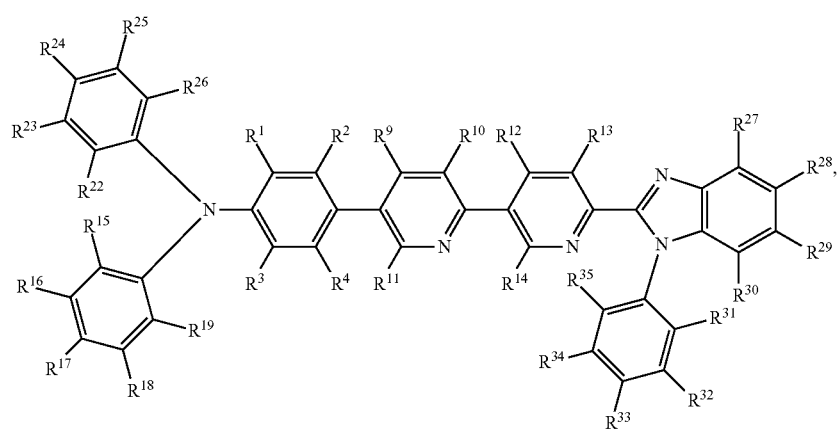

-continued
Formula 21
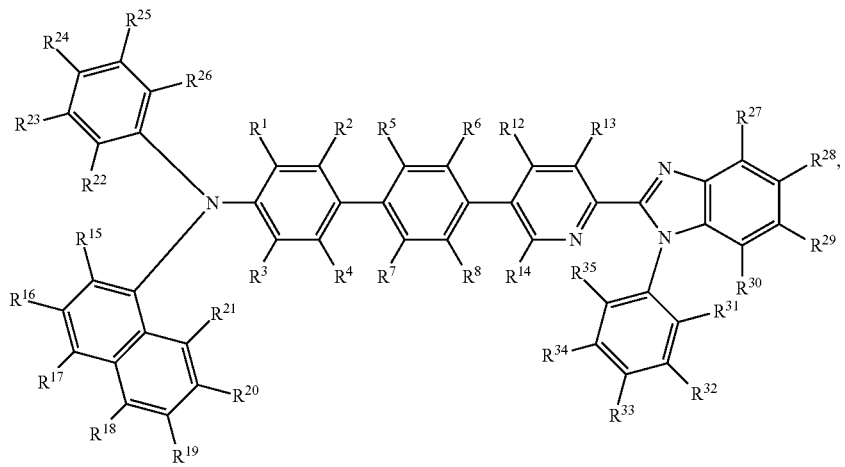
Formula 22
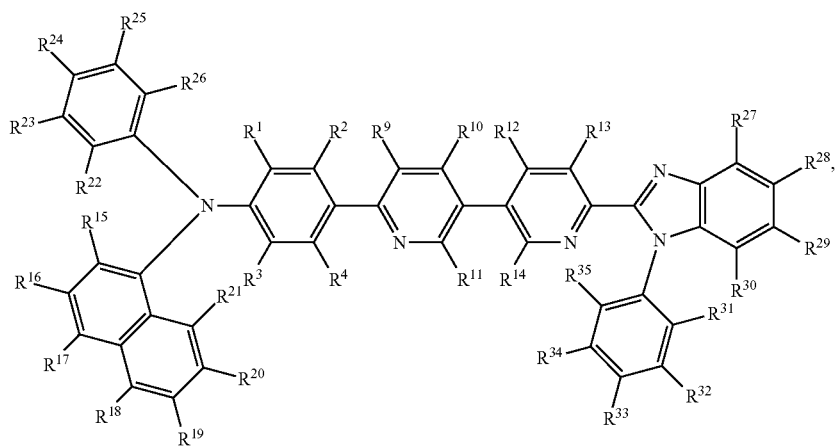
Formula 23
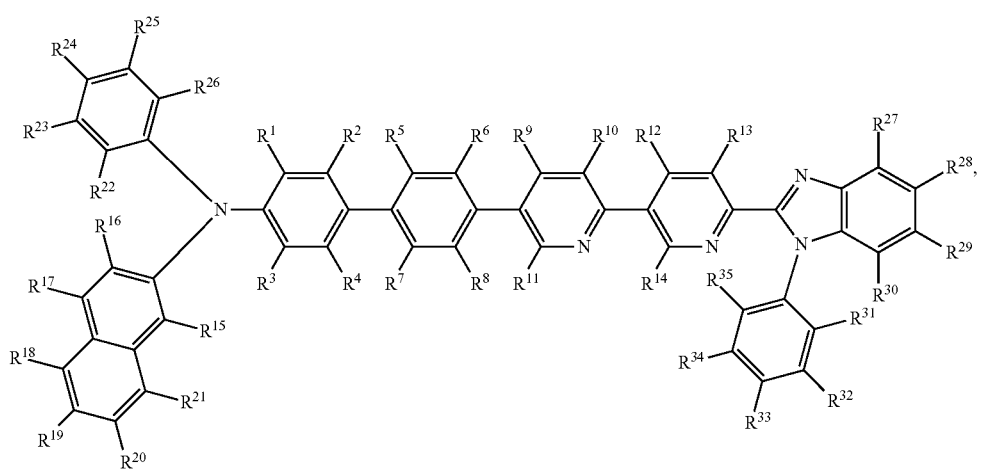

Formula 24
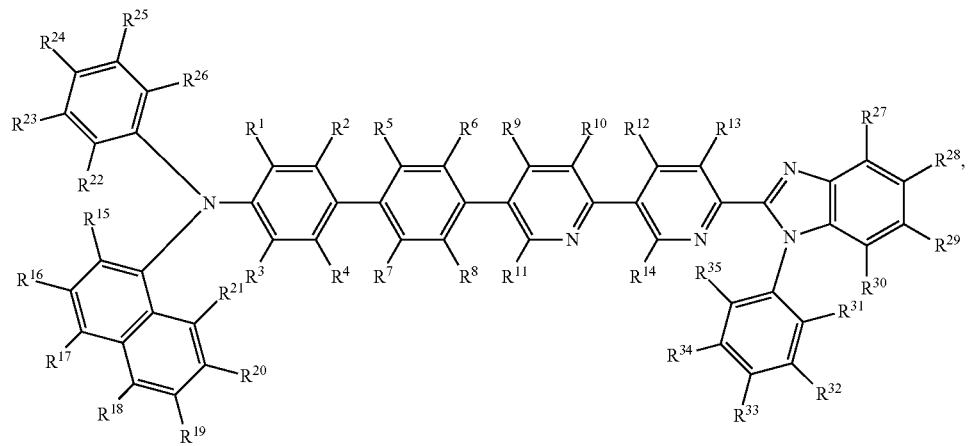
Formula 25
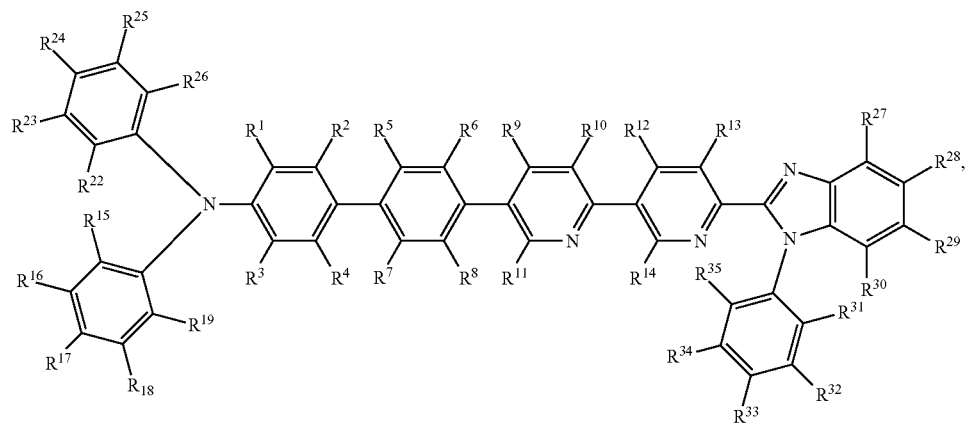
Formula 26
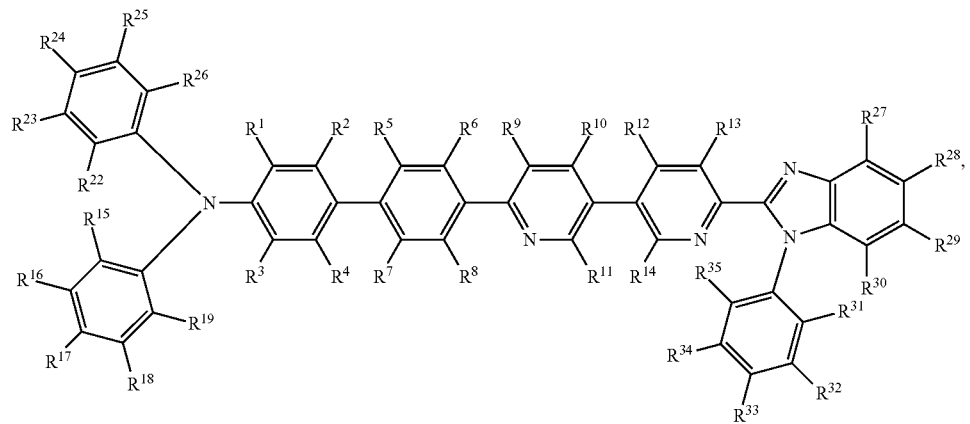

Formula 27

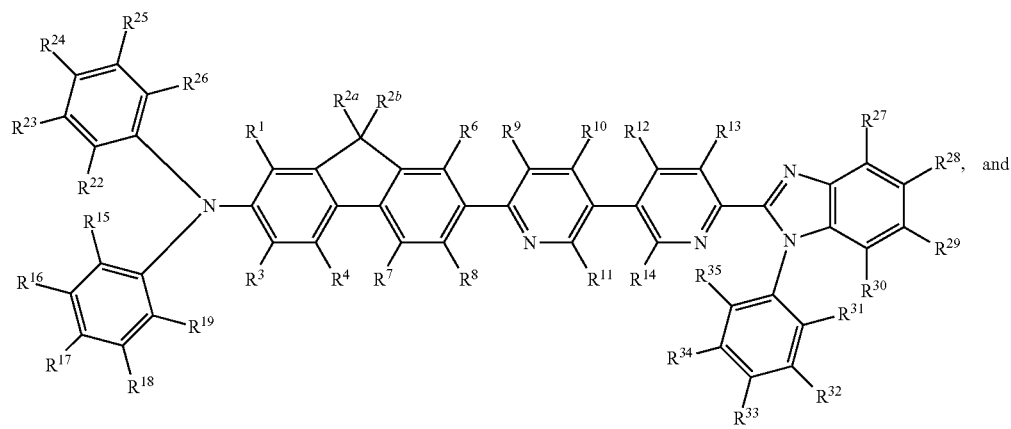

Formula 28

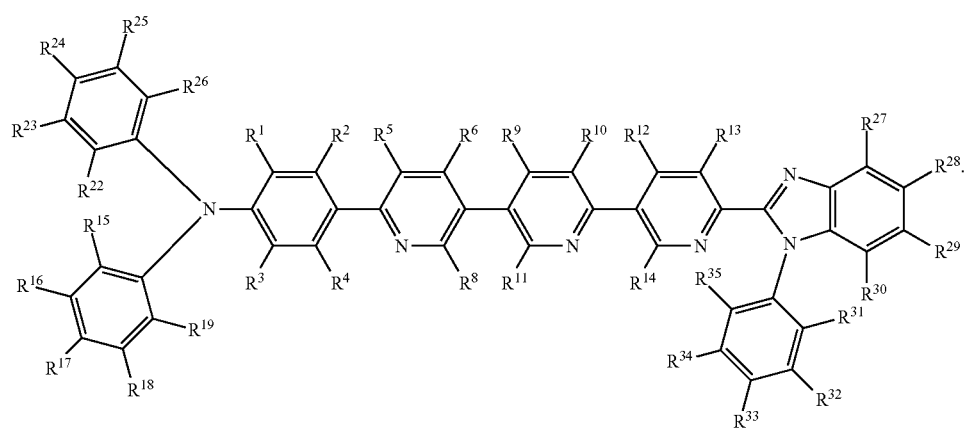

Generally $R^1$-$R^{36}$, $R^{2A}$, and $R^{5A}$ can be H or any substituent, such as a substituent having from 0 to 6 carbon atoms and from 0 to 5 heteroatoms, wherein each heteroatom is independently: O, N, S, F, Cl, Br, or I, and/or having a molecular weight of 15 g/mol to 300 g/mol. Any of $R^1$-$R^{36}$ may comprise: a) one or more alkyl moieties optionally substituted with, or optionally connected by or to, b) one or more functional groups, such as C=C, C≡C, CO, $CO_2$, CON, $NCO_2$, OH, SH, O, S, N, N=C, F, Cl, Br, I, CN, $NO_2$, $CO_2H$, $NH_2$, etc.; or, may be a substituent having no alkyl portion, such as F, Cl, Br, I, $NO_2$, CN, $NH_2$, OH, COH, $CO_2H$, etc. In some embodiments $R^1$-$R^{36}$ are independently H, $C_{1-3}$ alkyl, or $C_{1-3}$ perfluoroalkyl.

With respect to any relevant formula or structural depiction herein, some non-limiting examples of $R^1$ may include $R^A$, F, CN, $OR^A$, $CF_3$, $NO_2$, $NR^A R^B$, $COR^A$, $CO_2 R^A$, $OCOR^A$ $NR^A COR^B$, $CONR^A R^B$, etc. In some embodiments, $R^1$ may be H; $C_{1-3}$ alkyl, such as methyl, ethyl, propyl isomers (e.g., n-propyl and isopropyl), cyclopropyl, etc.; or, $C_{1-3}$ perfluoroalkyl, such as perfluoromethyl, perfluoroethyl, perfluoropropyl isomers, perfluorocyclopropyl, etc. In some embodiments, $R^1$ is H, F, or $C_{1-3}$ alkyl. In some embodiments, $R^1$ may be H. In some embodiments, $R^1$ is methyl.

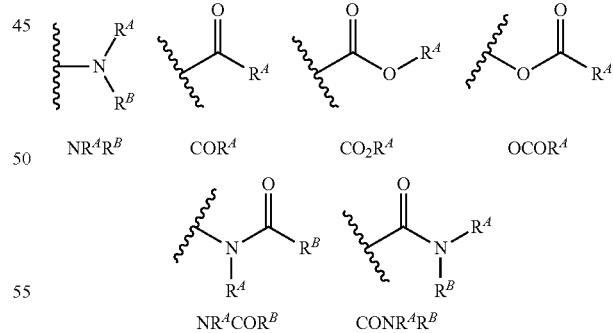

$NR^A R^B$    $COR^A$    $CO_2 R^A$    $OCOR^A$ $NR^A COR^B$    $CONR^A R^B$

Each $R^A$ may independently be H, or $C_{1-12}$ alkyl, including: linear or branched alkyl having a formula $C_a H_{a+1}$, or cycloalkyl having a formula $C_a H_{a-1}$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^A$ may be H or $C_{1-6}$ alkyl. In some embodiments, $R^4$ may be H or $C_{1-3}$ alkyl. In some embodiments, $R^4$ may be H or $CH_3$. In some embodiments, $R^4$ may be H.

Each $R^B$ may independently be H, or $C_{1-12}$ alkyl, including: linear or branched alkyl having a formula $C_aH_{a+1}$, or cycloalkyl having a formula $C_aH_a$, wherein a is 1, 2, 3, 4, 5, 6, 7, 8, 9, 10, 11, or 12, such as linear or branched alkyl of a formula: $CH_3$, $C_2H_5$, $C_3H_7$, $C_4H_9$, $C_5H_{11}$, $C_6H_{13}$, $C_8H_{17}$, $C_7H_{15}$, $C_9H_{19}$, $C_{10}H_{21}$, etc., or cycloalkyl of a formula: $C_3H_5$, $C_4H_7$, $C_5H_9$, $C_6H_{11}$, $C_7H_{13}$, $C_8H_{15}$, $C_9H_{17}$, $C_{10}H_{19}$, etc. In some embodiments, $R^B$ may be H or $C_{1-3}$ alkyl. In some embodiments, $R^B$ may be H or $CH_3$. In some embodiments, $R^B$ may be H.

With respect to any relevant formula or structural depiction herein, some non-limiting examples of $R^2$ may include $R^A$, F, Cl, $OR^A$, $CF_3$, $NO_2$, $NR^AR^B$, $COR^A$, $CO_2R^A$, $OCOR^A$ $NR^ACOR^B$, $CONR^AR^B$, etc. In some embodiments, $R^2$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^2$ is H, F, or $C_{1-3}$ alkyl. In some embodiments, $R^2$ may be H. In some embodiments, $R^2$ is ethyl.

With respect to any relevant formula or structural depiction herein, some non-limiting examples of $R^{2A}$ may include $R^A$, F, Cl, $OR^A$, $CF_3$, $NO_2$, $NR^AR^B$, $COR^A$, $CO_2R^A$, $OCOR^A$ $NR^ACOR^B$, $CONR^AR^B$, etc. In some embodiments, $R^{2A}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{2A}$ may be $CH_3$.

With respect to any relevant formula or structural depiction herein, some non-limiting examples of $R^3$ may include $R^A$, F, Cl, CN, $CF_3$, $NO_2$, $NR^AR^B$, $COR^A$, $CO_2R^A$, $OCOR^A$N-$R^ACOR^B$, $CONR^AR^B$, etc. In some embodiments, $R^3$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^3$ may be H. In some embodiments, $R^3$ is H, F, or $C_{1-3}$ alkyl. In some embodiments, $R^3$ is $OCH_3$.

With respect to any relevant formula or structural depiction herein, some non-limiting examples of $R^4$ may include $R^A$, F, Cl, CN, $OR^A$, $CF_3$, $NO_2$, $COR^A$, $CO_2R^A$, $OCOR^ANR^ACOR^B$, $CONR^AR^B$, etc. In some embodiments, $R^4$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^4$ may be H. In some embodiments, $R^4$ is H, F, or $C_{1-3}$ alkyl. In some embodiments, $R^4$ is F.

With respect to any relevant formula or structural depiction herein, some non-limiting examples of $R^5$ may include $R^A$, F, $CF_3$, $NO_2$, $NR^AR^B$, $COR^A$, $CO_2R^A$, $OCOR^ANR^ACOR^B$, $CONR^AR^B$, etc. In some embodiments, $R^5$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^5$ may be H. In some embodiments, $R^5$ is H, F, or $C_{1-3}$ alkyl. In some embodiments, $R^5$ is methyl.

With respect to any relevant formula or structural depiction herein, some non-limiting examples of $R^{5A}$ may include $R^A$, F, Cl, $OR^A$, $CF_3$, $NO_2$, $NR^AR^B$, $COR^A$, $CO_2R^A$, $OCOR^A$ $NR^ACOR^B$, $CONR^AR^B$, etc. In some embodiments, $R^{5A}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{5A}$ may be $CH_3$.

With respect to any relevant formula or structural depiction herein, some non-limiting examples of $R^6$ may include $R^A$, F, Cl, CN, $OR^A$, $CF_3$, $COR^A$, $CO_2R^A$, $OCOR^A$ etc. In some embodiments, $R^6$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^6$ may be H. In some embodiments, $R^6$ is H, F, or $C_{1-3}$ alkyl. In some embodiments, $R^6$ is methyl.

With respect to any relevant formula or structural depiction herein, some non-limiting examples of $R^7$ may include $R^A$, F, CN, $OR^A$, $CF_3$, $NR^AR^B$, $COR^A$, $CO_2R^A$, $OCOR^ANR^ACOR^B$, $CONR^AR^B$, etc. In some embodiments, $R^7$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^7$ may be H. In some embodiments, $R^7$ is H, F, or $C_{1-3}$ alkyl. In some embodiments, $R^7$ is F.

With respect to any relevant formula or structural depiction herein, some non-limiting examples of $R^8$ may include $R^A$, F, $CF_3$, $OCOR^A$, etc. In some embodiments, $R^8$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, etc. In some embodiments, $R^8$ may be H. In some embodiments, $R^8$ is H, F, or $C_{1-3}$ alkyl. In some embodiments, $R^8$ is OH.

With respect to any relevant formula or structural depiction herein, some non-limiting examples of $R^9$ may include $R^A$, F, $OR^A$, $CF_3$, $NO_2$, $NR^AR^B$, $COR^A$, $CO_2R^A$, $OCOR^A$, $CONR^AR^B$, etc. In some embodiments, $R^9$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^9$ may be H. In some embodiments, $R^9$ is H, F, or $C_{1-3}$ alkyl. In some embodiments, $R^9$ may be $CH_3$.

With respect to any relevant formula or structural depiction herein, some non-limiting examples of $R^{10}$ may include $R^A$, F, $CF_3$, $NO_2$, etc. In some embodiments, $R^{10}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{10}$ may be H. In some embodiments, $R^{10}$ is H, F, or $C_{1-3}$ alkyl. In some embodiments, $R^{10}$ is methyl.

With respect to any relevant formula or structural depiction herein, some non-limiting examples of $R^{11}$ may include $R^A$, F, CN, $OR^A$, $CF_3$, $NO_2$, $NR^ACOR^B$, $CONR^AR^B$, etc. In some embodiments, $R^{11}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{11}$ may be H. In some embodiments, $R^{11}$ is H, F, or $C_{1-3}$ alkyl. In some embodiments, $R^{11}$ is F.

With respect to any relevant formula or structural depiction herein, some non-limiting examples of $R^{12}$ may include $R^A$, F, $CF_3$, $NR^AR^B$, $COR^A$, $CO_2R^A$, $OCOR^ANR^ACOR^B$, $CONR^AR^B$, etc. In some embodiments, $R^{12}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{12}$ may be H. In some embodiments, $R^{12}$ is H, F, or $C_{1-3}$ alkyl. In some embodiments, $R^{12}$ is COH.

With respect to any relevant formula or structural depiction herein, some non-limiting examples of $R^{13}$ may include $R^A$, F, Cl, $CF_3$, $NO_2$, $COR^A$, $CO_2R^A$, $OCOR^A$ etc. In some embodiments, $R^{13}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{13}$ may be H. In some embodiments, $R^{13}$ is H, F, or $C_{1-3}$ alkyl. In some embodiments, $R^{13}$ is methyl.

With respect to any relevant formula or structural depiction herein, some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$ $NR^ACOR^B$, $CONR^AR^B$, etc. In some embodiments, $R^{14}$ may be H; $C_{1-3}$ alkyl, such as methyl, ethyl, propyl isomers, cyclopropyl, etc.; or $C_{1-3}$ perfluoroalkyl, such as perfluoromethyl, perfluoroethyl, perfluoropropyl isomers, perfluorocyclopropyl, etc. In some embodiments, $R^{14}$ may be H. In some embodiments, $R^{14}$ is H, F, or $C_{1-3}$ alkyl. In some embodiments, $R^{14}$ is CN.

With respect to any relevant formula or structural depiction herein, some non-limiting examples of $R^{15}$ may include $R^A$, F, $OR^A$, $SR^A$, $NR^AR^B$, etc. In some embodiments, $R^{15}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{15}$ is H, OH, $NH_2$, $C_{1-3}$ alkyl (such as methyl, ethyl, propyl, isopropyl, etc.), $C_{1-3}$—O-alkyl (such as —O-methyl, —O-ethyl, —O-propyl, —O-isopropyl, etc.), or $C_{1-3}$ amino (such as —$NHCH_3$, —$N(CH_3)_2$, etc.). In some embodiments, $R^{15}$ is H, F, methyl, ethyl, propyl, or isopropyl. In some embodiments, $R^{15}$ may be H.

With respect to any relevant formula or structural depiction herein, some non-limiting examples of $R^{16}$ may include $R^A$, F, $OR^A$, $NR^AR^B$, etc. In some embodiments, $R^{16}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{16}$ is H, OH, $NH_2$, $C_{1-3}$ alkyl, —$OCH_3$, $OC_2H_5$, or $C_{1-3}$ amino. In some embodiments, $R^{16}$ is H, F, methyl, ethyl, propyl, or isopropyl. In some embodiments, $R^{16}$ may be H. In some embodiments, $R^{16}$ may be $CH_3$.

With respect to any relevant formula or structural depiction herein, some non-limiting examples of $R^{17}$ may include $R^A$, F, $OR^A$, $NR^AR^B$, etc. In some embodiments, $R^{17}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{17}$ is H, OH, $NH_2$, $C_{1-3}$ alkyl, $C_{1-3}$—O-alkyl, or $C_{1-3}$ amino. In some embodiments, $R^{17}$ is H, F, methyl, ethyl, propyl, or isopropyl. In some embodiments, $R^{17}$ may be H.

With respect to any relevant formula or structural depiction herein, some non-limiting examples of $R^{18}$ may include $R^A$, F, $OR^A$, $NR^AR^B$, etc. In some embodiments, $R^{18}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{18}$ is H, OH, $NH_2$, $C_{1-3}$ alkyl, $C_{1-3}$—O-alkyl, or $C_{1-3}$ amino. In some embodiments, $R^{18}$ is H, F, methyl, ethyl, propyl, or isopropyl. In some embodiments, $R^{18}$ may be H.

With respect to any relevant formula or structural depiction herein, some non-limiting examples of $R^{19}$ may include $R^A$, F, $OR^A$, $NR^AR^B$, etc. In some embodiments, $R^{19}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{19}$ is H, OH, $NH_2$, $C_{1-3}$ alkyl, $C_{1-3}$—O-alkyl, or $C_{1-3}$ amino. In some embodiments, $R^{19}$ is H, F, methyl, ethyl, propyl, or isopropyl. In some embodiments, $R^{19}$ may be H.

With respect to any relevant formula or structural depiction herein, some non-limiting examples of $R^{20}$ may include $R^A$, F, $OR^A$, $NR^AR^B$, $NR^ACOR^B$, etc. In some embodiments, $R^{20}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{20}$ is H, OH, $NH_2$, $C_{1-3}$ alkyl, $C_{1-3}$—O-alkyl, or $C_{1-3}$ amino. In some embodiments, $R^{20}$ is H, F, methyl, ethyl, propyl, or isopropyl. In some embodiments, $R^{20}$ may be H.

With respect to any relevant formula or structural depiction herein, some non-limiting examples of $R^{21}$ may include $R^A$, F, $OR^A$, $NR^AR^B$, $NR^ACOR^B$, etc. In some embodiments, $R^{21}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{21}$ is H, OH, $NH_2$, $C_{1-3}$ alkyl, $C_{1-3}$—O-alkyl, or $C_{1-3}$ amino. In some embodiments, $R^{21}$ is H, F, methyl, ethyl, propyl, or isopropyl. In some embodiments, $R^{21}$ may be H.

With respect to any relevant formula or structural depiction herein, some non-limiting examples of $R^{22}$ may include $R^A$, F, $OR^A$, $NR^AR^B$, $NR^ACOR^B$, etc. In some embodiments, $R^{22}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{22}$ is H, OH, $NH_2$, $C_{1-3}$ alkyl, or methoxy. In some embodiments, $R^{22}$ is H, F, methyl, ethyl, propyl, or isopropyl. In some embodiments, $R^{22}$ may be H.

With respect to any relevant formula or structural depiction herein, some non-limiting examples of $R^{23}$ may include $R^A$, F, $OR^A$, $NR^AR^B$, $NR^ACOR^B$, etc. In some embodiments, $R^{23}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{23}$ is H, OH, $NH_2$, $C_{1-3}$ alkyl, $C_{1-3}$—O-alkyl, or $C_{1-3}$ amino. In some embodiments, $R^{23}$ is H, F, methyl, ethyl, propyl, or isopropyl. In some embodiments, $R^{23}$ may be H.

With respect to any relevant formula or structural depiction herein, some non-limiting examples of $R^{24}$ may include $R^A$, F, $C^1$, $OR^A$, $NR^AR^B$, etc. In some embodiments, $R^{24}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{24}$ is H, OH, $NH_2$, $C_{1-3}$ alkyl, $C_{1-3}$—O-alkyl, or $C_{1-3}$ amino. In some embodiments, $R^{24}$ is H, F, methyl, ethyl, propyl, or isopropyl. In some embodiments, $R^{24}$ may be H or $CH_3$. In some embodiments, $R^{24}$ may be H. In some embodiments, $R^{24}$ may be $CH_3$.

With respect to any relevant formula or structural depiction herein, some non-limiting With respect to any relevant formula or structural depiction herein, some non-limiting examples of $R^{25}$ may include $R^A$, F, $OR^A$, $NR^AR^B$, $NR^ACOR^B$, etc. In some embodiments, $R^{25}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{25}$ is H, OH, $NH_2$, $C_{1-3}$ alkyl, or $C_{1-2}$—O-alkyl. In some embodiments, $R^{25}$ is H, F, methyl, ethyl, propyl, or isopropyl. In some embodiments, $R^{25}$ may be H.

With respect to any relevant formula or structural depiction herein, some non-limiting examples of $R^{26}$ may include $R^A$, F, $OR^A$, $NR^AR^B$, $NR^ACOR^B$, etc. In some embodiments, $R^{26}$ may be H; or $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc. In some embodiments, $R^{26}$ is H, OH, $NH_2$, methyl, or methoxy. In some embodiments, $R^{26}$ is H, F, methyl, ethyl, propyl, or isopropyl. In some embodiments, $R^{26}$ may be H.

With respect to any relevant formula or structural depiction herein, some non-limiting examples of $R^{27}$ may include $R^A$, F, CN, $CF_3$, $NO_2$, $COR^A$, $CO_2R^A$, $NR^ACOR^B$, $CONR^AR^B$, etc. In some embodiments, $R^{27}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{27}$ may be H, F, CN, $CF_3$, COH, $CO_2H$, $CO_2CH_3$, or $NO_2$. In some embodiments, $R^{27}$ may be H or F.

With respect to any relevant formula or structural depiction herein, some non-limiting examples of $R^{28}$ may include $R^A$, F, CN, $CF_3$, $NO_2$, $COR^A$, $CO_2R^A$, $NR^ACOR^B$, $CONR^AR^B$, etc. In some embodiments, $R^{28}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{28}$ may be H, F, CN, $CF_3$, COH, $COCH_3$, $CO_2CH_3$, or $NO_2$. In some embodiments, $R^{28}$ may be H or F.

With respect to any relevant formula or structural depiction herein, some non-limiting examples of $R^{29}$ may include $R^A$, F, CN, $CF_3$, $NO_2$, $COR^A$, $CO_2R^A$, $NR^ACOR^B$, $CONR^AR^B$, etc. In some embodiments, $R^{29}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{29}$ may be H, F, CN, $CF_3$, COH, $CO_2H$, $CO_2CH_3$, $COCH_3$, or $NO_2$. In some embodiments, $R^{29}$ may be H or F.

With respect to any relevant formula or structural depiction herein, some non-limiting examples of $R^{30}$ may include $R^A$, F, CN, $CF_3$, $NO_2$, $COR^A$, $CO_2R^A$, $NR^ACOR^B$, $CONR^AR^B$, etc. In some embodiments, $R^{30}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{30}$ may be H, F, CN, $CF_3$, or COH. In some embodiments, $R^{30}$ may be H or F.

With respect to any relevant formula or structural depiction herein, some non-limiting examples of $R^{31}$ may include $R^A$, F, CN, $CF_3$, $NO_2$, $COR^A$, $CO_2R^A$, $NR^ACOR^B$, $CONR^AR^B$, etc. In some embodiments, $R^{31}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{31}$ may be H, F, Cl, CN, $CF_3$, COH, $CO_2H$, NHCOH, $CO_2CH_3$, or $NO_2$. In some embodiments, $R^{31}$ may be H or F.

With respect to any relevant formula or structural depiction herein, some non-limiting examples of $R^{32}$ may include $R^A$, F, CN, $CF_3$, $NO_2$, $COR^A$, $CO_2R^A$, $NR^ACOR^B$, $CONR^AR^B$, etc. In some embodiments, $R^{32}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{32}$ may be H, F, CN, $CF_3$, COH, or $NO_2$. In some embodiments, $R^{32}$ may be H or F.

With respect to any relevant formula or structural depiction herein, some non-limiting examples of $R^{33}$ may include $R^A$, F, CN, $CF_3$, $NO_2$, COH, $COR^A$, $CO_2R^A$, $NR^ACOR^B$, $CONR^AR^B$, etc. In some embodiments, $R^{33}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{33}$ may be H, F, CN, $CF_3$, COH, $CO_2H$, $CO_2CH_3$, or $NO_2$. In some embodiments, $R^{33}$ may be H or F.

With respect to any relevant formula or structural depiction herein, some non-limiting examples of $R^{34}$ may include $R^A$, F, CN, $CF_3$, $CO_2R^A$, $NO_2$, etc. In some embodiments, $R^{34}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{34}$ may be H, F, CN, $CF_3$, COH, $CO_2H$, $CO_2CH_3$, or $NO_2$. In some embodiments, $R^{34}$ may be H or F.

With respect to any relevant formula or structural depiction herein, some non-limiting examples of $R^{35}$ may include $R^A$, F, CN, $CF_3$, $COCH_3$, $NO_2$, etc. In some embodiments, $R^{35}$ may be H; F; $C_{1-6}$ alkyl, such as methyl, ethyl, propyl isomers, butyl isomers, pentyl isomers, hexyl isomers, cyclopropyl, cyclobutyl isomers, cyclopentyl isomers, cyclohexyl isomers, etc.; or $C_{1-6}$ perfluoroalkyl, such as perfluoromethyl, perfluoroethyl, perfluoropropyl isomers, perfluorocyclopropyl, etc. In some embodiments, $R^{35}$ may be H, F, CN, or $CF_3$. In some embodiments, $R^{35}$ may be H or F.

With respect to any relevant formula or structural depiction herein, some non-limiting examples of $R^{36}$ may include $R^A$, $CF_3$, optionally substituted phenyl, etc. In some embodiments, $R^{36}$ may be unsubstituted phenyl.

Some embodiments include optionally substituted BE-1, optionally substituted BE-2, optionally substituted BE-3, optionally substituted BE-4, optionally substituted BE-5, optionally substituted BE-6, optionally substituted BE-7, optionally substituted BE-8, optionally substituted BE-9, optionally substituted BE-10, optionally substituted BE-11, optionally substituted BE-12, optionally substituted BE-13, or optionally substituted BE-14.

The compounds and compositions described herein can be incorporated into light-emitting devices in various ways. For example, an embodiment provides an organic component disposed between an anode and a cathode. In some embodiments, the device may be configured so that holes can be transferred from the anode to the organic component. In some embodiments, the device may be configured so that electrons can be transferred from the cathode to the organic component. The organic component may comprise the compounds and/or compositions described herein.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in, e.g., "Flexible light-emitting diodes made from soluble conducting polymer," Nature, vol. 357, pp. 477-479 (11 Jun. 1992), which is incorporated by reference herein for its relevant teachings. Examples of suitable high work function metals and metal oxides include but are not limited to Au, Pt, or alloys thereof; ITO; IZO; and the like. In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host. A host may comprise a compound described herein, a hole-transport material, an electron-transport material, and/or an ambipolar material. In some embodiments, the device may be configured so that holes can be transferred from the anode to the light-emitting layer. In some embodiments, the device may be configured so that electrons can be transferred from the cathode to the light-emitting layer. If present, the amount of the host in a light-emitting layer can vary. In one embodiment, the amount of a host in a light-emitting layer may be in the range of from about 1% to about 99.9% by weight of the light-emitting layer. In another embodiment, the amount of a host in a light-emitting layer may be in the range of from about 90% to about 99% by weight of the light-emitting layer. In another embodiment, the amount of a host in a light-emitting layer may be about 97% by weight of the light-emitting layer.

In some embodiments, the mass of the light-emitting component may be about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium(III)-picolinate, bis-(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis (4,6-difluorophenylpyridinato)-5-(pyridine-2-yl)-1H-tetrazolate, bis[2-(4,6-difluorophenyl)pyridinato-N,C$^{2'}$]iridium (III)tetra(1-pyrazolyl)borate, etc. The structures corresponding to these compounds are as follows:

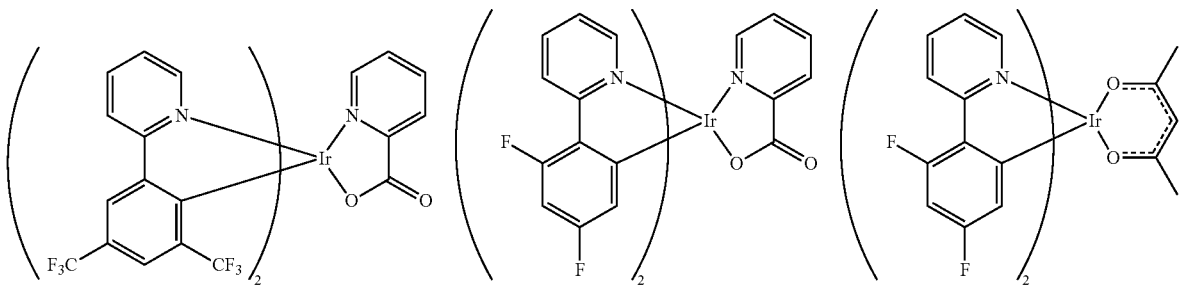

bis-{2-[3,5-bis(trifluoromethyl)phenyl]pyridinato-N,C2'}iridium(III)-picolinate (Ir(CF$_3$ppy)$_2$(Pic)

bis(2-[4,6-difluorophenyl]pyridinato-N,C2')iridium (III) picolinate [FIrPic]

bis(2-[4,6-difluorophenyl]pyridinato-N,C2')iridium(acetylacetonate) [FIr(acac)]

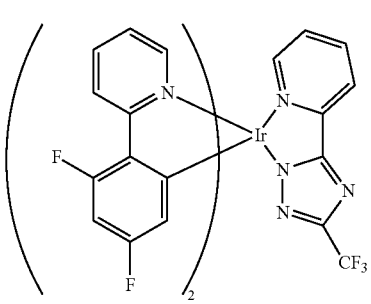

Iridium (III) bis(4,6-difluorophenylpyridinato)-3-(trifluoromethyl)-5-(pyridine-2-yl)-1,2,4-triazolate (FIrtaz)

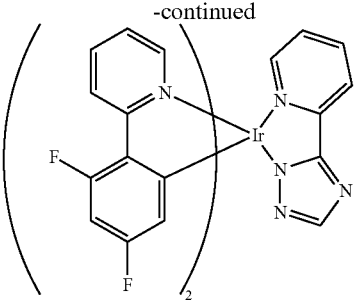

Iridium (III) bis(4,6-difluorophenylpyridinato)-5-(pyridine-2-yl)-1H-tetrazolate (FIrN4)

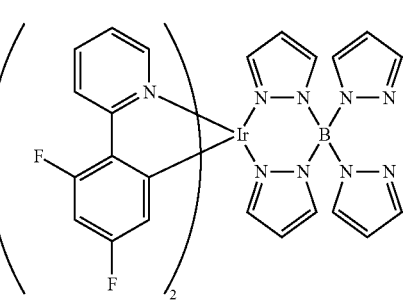

bis[2-(4,6-difluorophenyl)pyridinato-N,C$^{2'}$]iridium(III)tetra(1-pyrazolyl)borate (Fir6)

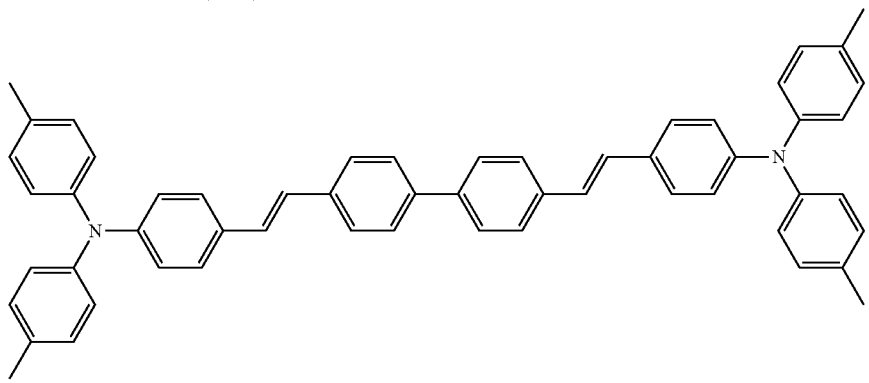

4,4'-((1E,1'E)-[1,1'-biphenyl]-4,4'-diylbis(ethene-2,1-diyl))bis(N,N-di-p-tolylaniline) (DPAVBi).

The thickness of a light-emitting layer may vary. In one embodiment, a light-emitting layer may have a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate (Alq$_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI or TPBi), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron injection layer between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4] triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer; e.g., between the light-emitting layer and the anode. In an embodiment, the band gap energy of the material(s) that comprise exciton-blocking layer may be large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl ($\alpha$-NPD), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenyl-benzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component can be deposited on the anode, the hole-transport layer, or the hole-injection layer. The light-emitting layer may contain a compound described herein, and/or a compound described herein may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

Some embodiments may have a structure represented by FIG. 1. A hole-injection layer 10 is disposed on the anode 5. A hole-transport layer 15 is disposed on the hole-injection layer 15. The emissive layer 20 is disposed on the hole-transport layer 15. An electron-transport layer 30 is disposed on the emissive layer 20, and the cathode 35 is disposed on the electron-transport layer 30.

In some embodiments, the OLED may be made by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material described herein and a solvent.

In some embodiments, a device comprising the subject compounds can provide a significantly increased device lifetime compared with commercially available compounds. In some embodiments, the devices can provide a T50(h) @ 10000 nit lifetime of at least about 125, 150, 175, 185, and/or 200 hours. In some embodiments, the desired lifetime can be determined by examining the luminescent/emissive decay of the device by measuring the luminescent, e.g., $cd/m^2$, after applying a constant current of a 16 mA to device (corresponding to about 10000 $cd/m^2$) for a device having an active emissive area of about 13.2 $mm^2$.

EXAMPLES

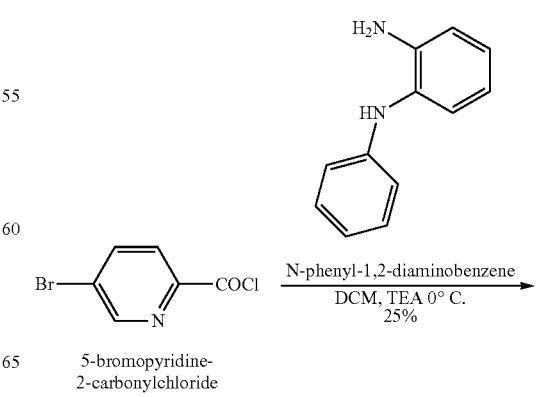

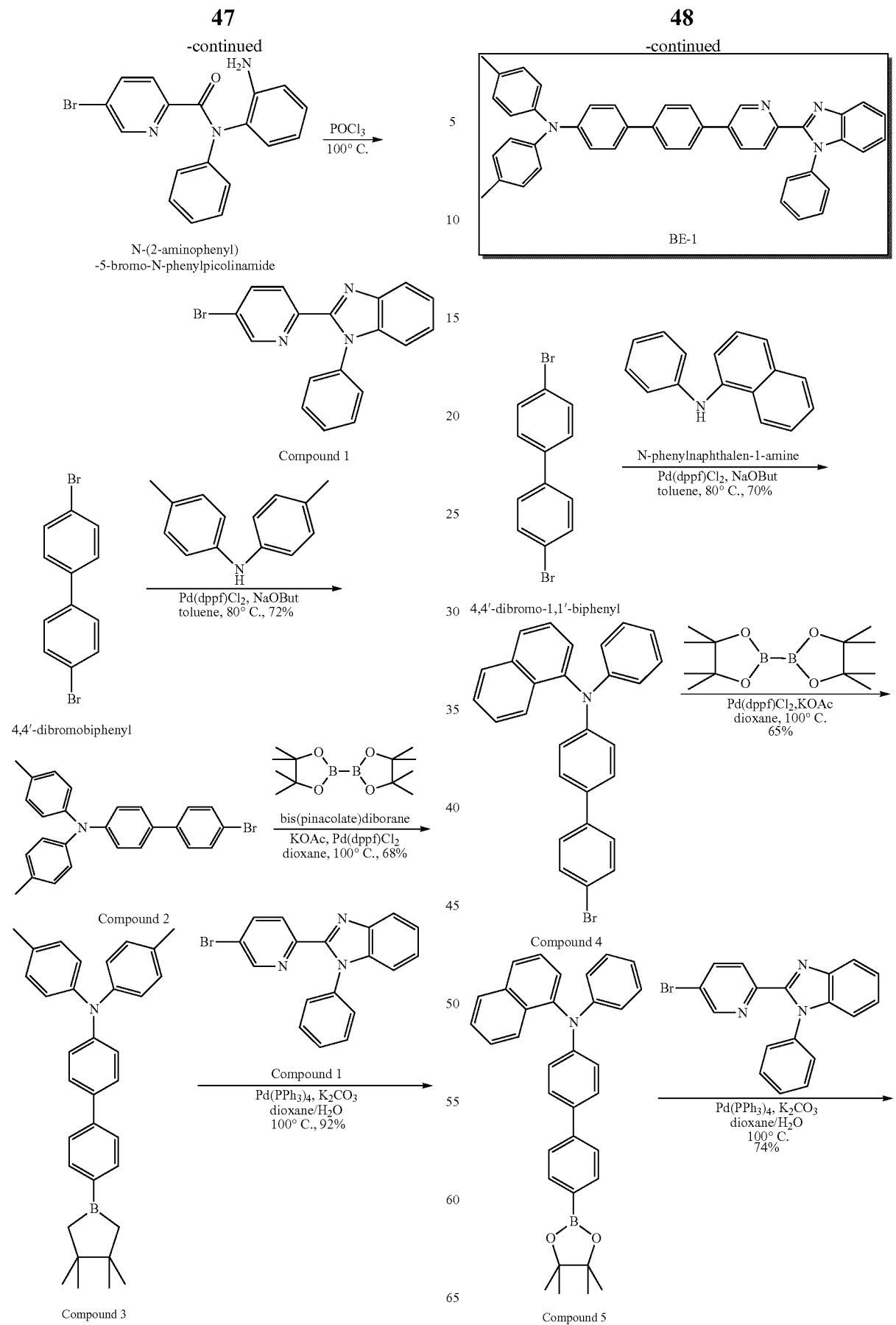

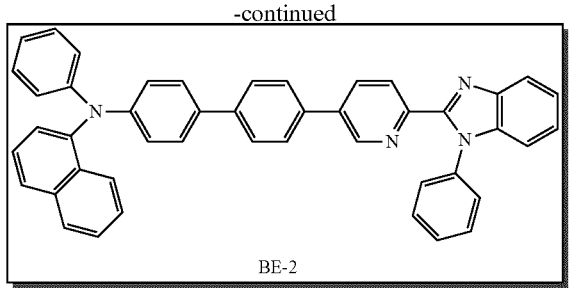

BE-2

Example 1

Synthesis Examples

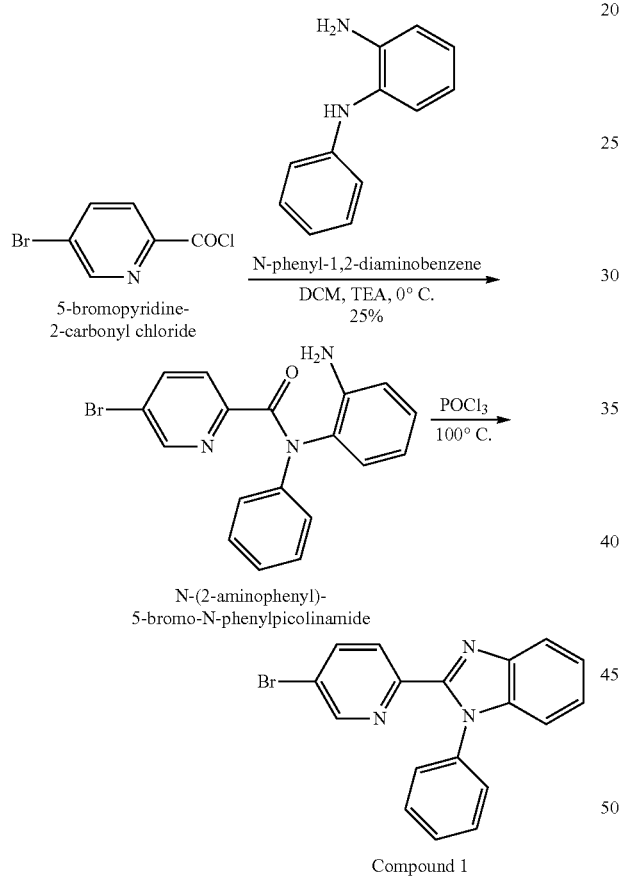

2-(5-bromopyridin-2-yl)-1-phenyl-1H-benzo[d]imidazole (Compound 1)

To a suspension of 5-bromopyridine-2-carbonyl chloride (10.11 g, 46 mmol), N-phenyl-1,2-diaminobenzene (8.46 g, 46 mmol) in anhydrous dichloromethane (DCM) (100 mL), was added triethylamine (TEA) at 0° C. Then the whole was stirred at room temperature (RT) for about 20 hours. The mixture was poured into water, extracted with dichloromethane (100 mL×2). The organic phase was collected, dried over sodium sulfate ($Na_2SO_4$), and passed through a pad of silica gel (hexanes/ethyl acetate 4:1). After removal of solvent, a brown oil was obtained, which was dissolved in dioxane (150 mL), phosphoryl chloride ($POCl_3$) (25 mL) was added at 0° C., and the mixture was then heated at about 100° C. under argon overnight. Then the whole was poured into ice (200 g) after being cooled to RT, then neutralized by sodium carbonate ($Na_2CO_3$), and extracted with dichloromethane (DCM) (200 mL×2). The organic phase was dried over $Na_2SO_4$, absorbed on silica gel, and purified by a silica gel column (hexanes/ethyl acetate 4:1). The desired fraction was collected, concentrated, and reprecipitated with hexanes. After filtration and being washed with methanol, an off-white crystalline solid (Compound 1) was obtained, 4.02 g, with an overall 25% yield.

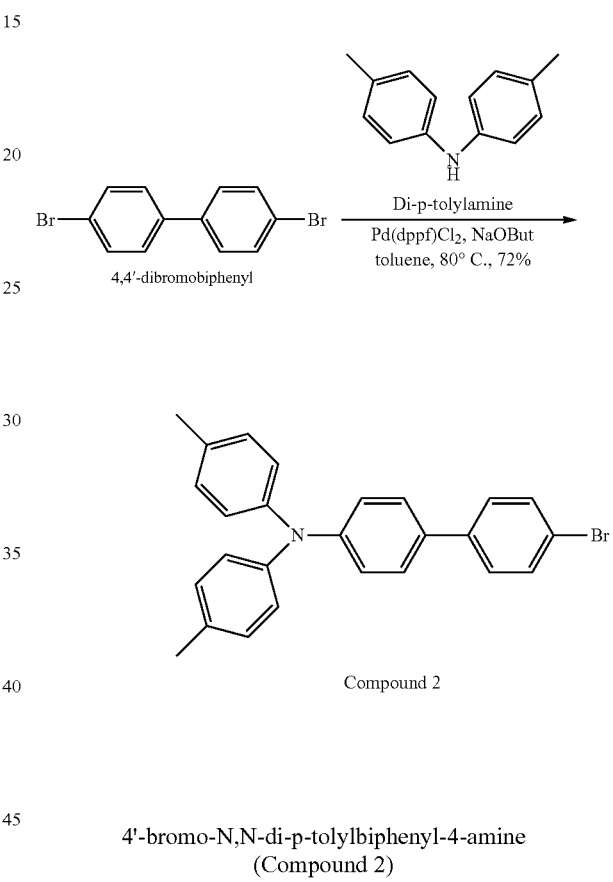

4'-bromo-N,N-di-p-tolylbiphenyl-4-amine (Compound 2)

Di-p-tolylamine (6.0 g, 30.4 mmol), 4,4'-dibromobiphenyl (23.7 g, 76.0 mmol), sodium tert-butoxide (NaOBut) (7.26 g, 91.2 mmol), and [1,1-bis(diphenylphosphino)ferrocene]palladium(11)dichloride (Pd(dppf)$Cl_2$) (666 mg, 0.912 mmol, 3 mol %) were added to anhydrous toluene (about 250 mL) and degassed in argon for about 30 minutes. The resulting mixture was heated to about 80° C. for about 6 hours, after which a TLC analysis indicated that most of the di-p-tolylamine was consumed. After being cooled to RT, the mixture was poured into saturated aqueous sodium bicarbonate ($NaHCO_3$) and extracted with two portions of ethyl acetate (EtOAc). The organic layers were pooled and washed with water and brine, then dried over magnesium sulfate ($MgSO_4$). After filtration the extract was concentrated to dryness on a rotary evaporator, then loaded onto silica gel. A flash column (gradient of 100% hexane to 1% methylene chloride in hexane) resulted in 9.4 g (72%) of a white solid (Compound 2) confirmed by $^1$H NMR in deuterated chloroform ($CDCl_3$).

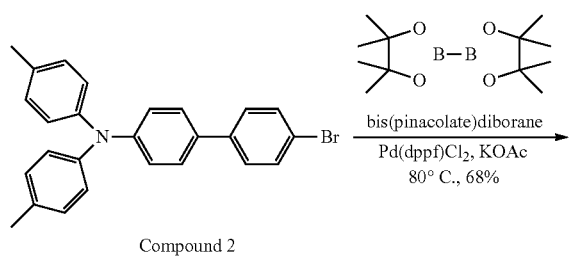

Compound 2

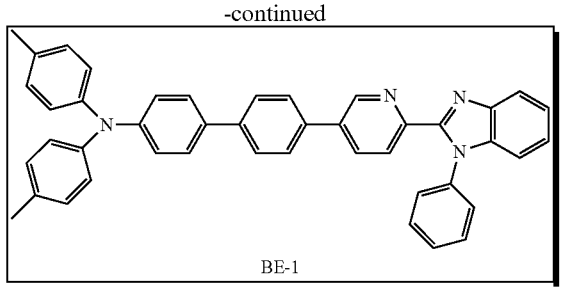

BE-1

Chemical Formula: $C_{44}H_{34}N_4$
Molecular Weight: 618.77

Compound BE-1

A mixture of Compound 3 (1.426 g, 3 mmol), Compound 1 (1.05 g, 3 mmol), potassium carbonate ($K_2CO_3$) (0.828 g, 6 mmol) and tetrakis(triphenylphosphine)Palladium(0) (Pd(PPh$_3$)$_4$) in dioxane/water (30 mL/8 mL) was degassed for 30 min., then heated at 100° C. overnight. The whole was poured into ethyl acetate (250 mL), absorbed on silica gel, and purified by flash column (hexanes/ethyl acetate 4:1) to give a light yellow solid (Compound BE-1) after removal of solvents (1.7 g, in 92% yield). LCMS (APCI+) was calculated for $C_{44}H_{35}N_4$ (M+H)=619. found: m/e=619.

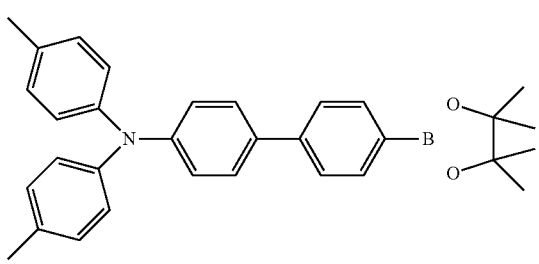

Compound 3

4'-(4,4,5,5-tetramethyl-1,3,2-dioxaborolan-2-yl)-N,N-di-p-tolyl-[1,1'-biphenyl]-4-amine (Compound 3)

A mixture of Compound 2 (2.0 g, 4.67 mmol), bis(pinacolate)diborane (1.27 g, 5 mmol), Pd(dppf)Cl$_2$ (0.18 g, 0.25 mmol) and potassium acetate (0.98 g, 10 mmol) in anhydrous dioxane (50 mL) was degassed and heated at about 80° C. for 16 hours. After being cooled to RT, the whole was poured into ethyl acetate (100 mL) and the solid filtered off. The organic solution was loaded on silica gel, and purified by flash column (hexanes/ethyl acetate 6:1) to give a white solid Compound 3 (1.5 g, in 68% yield).

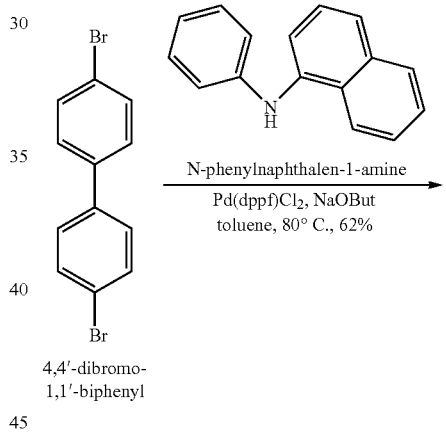

4,4'-dibromo-1,1'-biphenyl

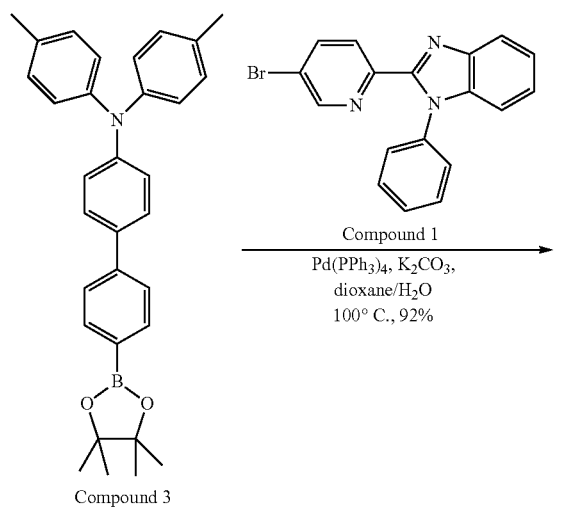

Compound 3

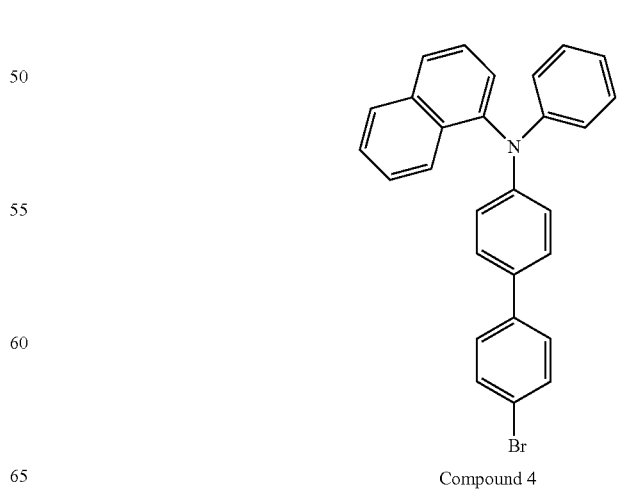

Compound 4

N-(4'-bromo-[1,1'-biphenyl]-4-yl)-N-phenylnaphthalen-1-amine (Compound 4)

A mixture of N-phenylnaphthalen-1-amine (4.41 g, 20 mmol), 4,4'-dibromo-1,1'-biphenyl (15 g, 48 mmol), sodium tert-butoxide (NaOBut) (4.8 g, 50 mmol) and Pd(dppf)Cl$_2$ (0.44 g, 0.6 mmol) in anhydrous toluene (100 mL) was degassed and heated at 80° C. for about 10 hours. After cooling to RT, the mixture was poured into dichloromethane (400 mL) and stirred for about 30 min., then washed with brine (100 mL). The organic solution was collected and dried over Na$_2$SO$_4$, loaded on silica gel, and purified by flash column (hexanes to hexanes/ethyl acetate 90:1) to give a solid which was washed with methanol and dried under air to give a white solid Compound 4 (5.58 g, in 62% yield).

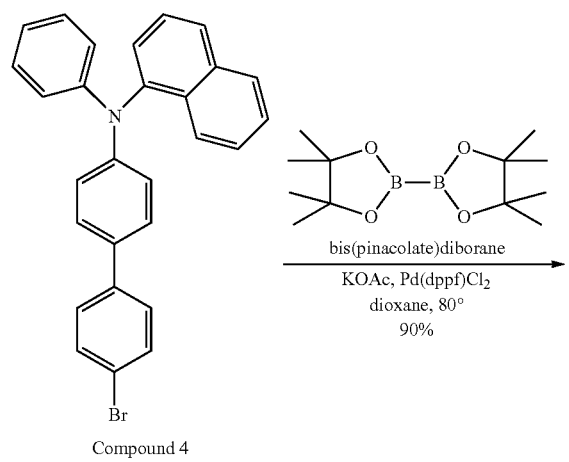

N-phenyl-N-(4'-(4,4,5,5-tetramethyl-1,3,2-dioxaborolan-2-yl)-[1,1'-biphenyl]-4-yl)naphthalen-1-amine (Compound 5)

A mixture of Compound 4 (5.5 g, 12.2 mmol), bis(pinacolate)diborane (3.10 g, 12.2 mmol), Pd(dppf)Cl$_2$ (0.446 mg, 0.6 mmol) and KOAc (5.5 g, 56 mmol) in anhydrous dioxane (60 mL) was degassed and heated at about 80° C. overnight. After being cooled to RT, the mixture was poured into ethyl acetate (200 mL), and washed with brine (150 mL). The organic solution was dried over Na$_2$SO$_4$, loaded on silica gel and purified by flash column (hexanes to hexanes/ethyl acetate 30:1) to collect the major fraction. After removal of solvent, the solid was washed with methanol, filtered and dried in air to give a white solid Compound 5 (5.50 g, in 90% yield).

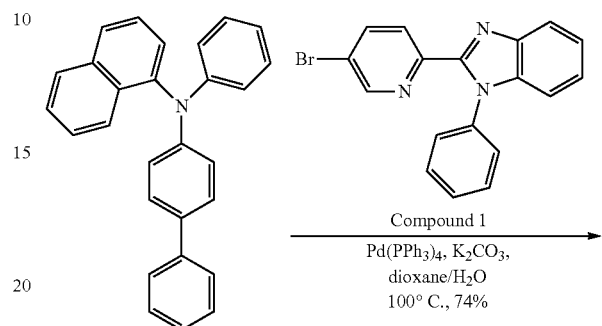

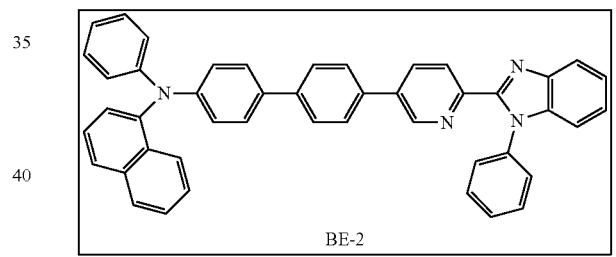

Compound BE-2

Chemical Formula: C$_{46}$H$_{32}$N$_4$
Molecular Weight: 640.77

A mixture of Compound 5 (1.744 g, 3.5 mmol), Compound 1 (1.171 g, 3.34 mmol), K$_2$CO$_3$ (1.38 g, 10 mmol) and Pd(PPh$_3$)$_4$ (0.231 g, 0.2 mmol) in dioxane/water (40 mL/10 mL) was degassed, then heated to 100° C. overnight. The whole was poured into ethyl acetate (200 mL), washed with brine, then dried over Na$_2$SO$_4$ and purified by flash silica gel column using eluents of (hexanes/ethyl acetate 9:1 to 6:1 to 3:1). The desired fraction was collected, concentrated and recrystallized in dichloromethane/hexanes to give a yellow solid (Compound BE-2) (1.65 g, in 74% yield). LCMS (APCI+) was calculated for C$_{46}$H$_{33}$N$_4$ (M+H)=641. found: m/e=641.

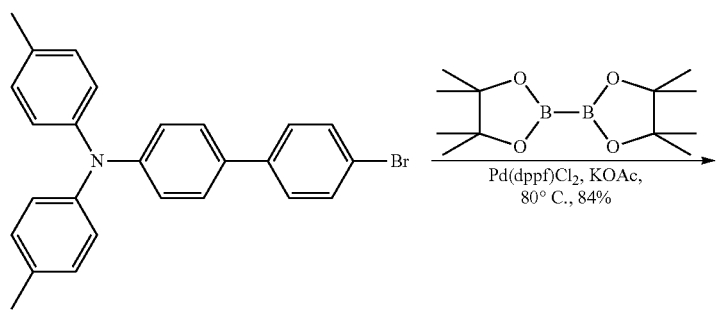
Compound 2
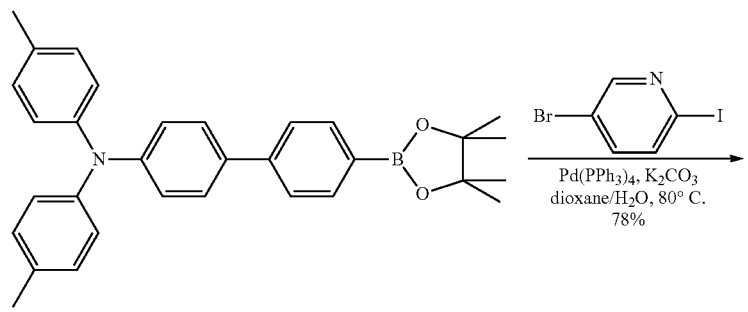
Compound 3
Molecular Weight: 475.43
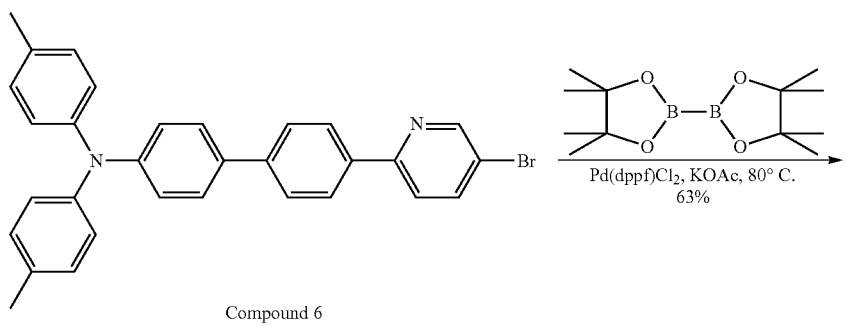
Compound 6
Molecular Weight: 505.45
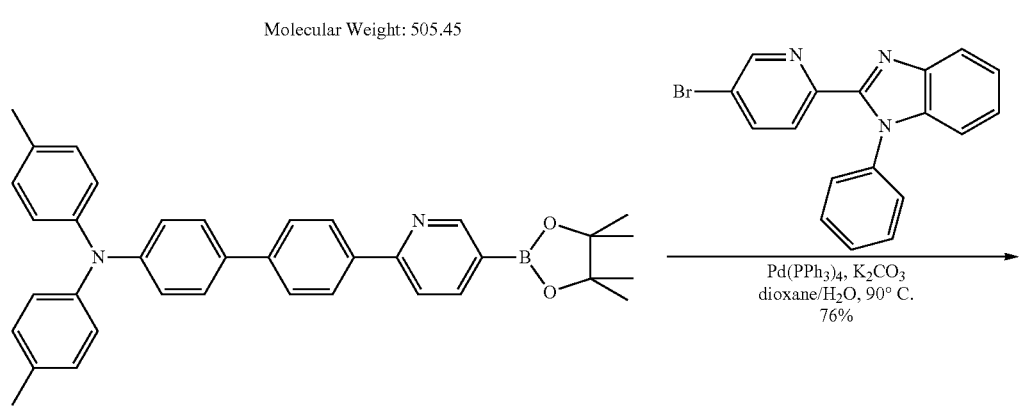
Compound 7
Molecular Weight: 552.51

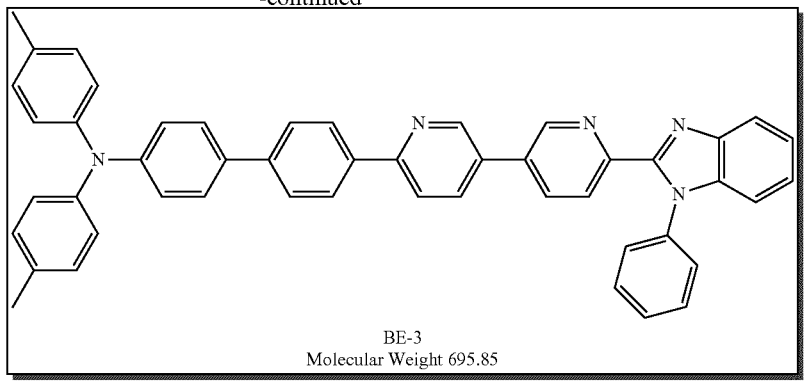
BE-3
Molecular Weight 695.85
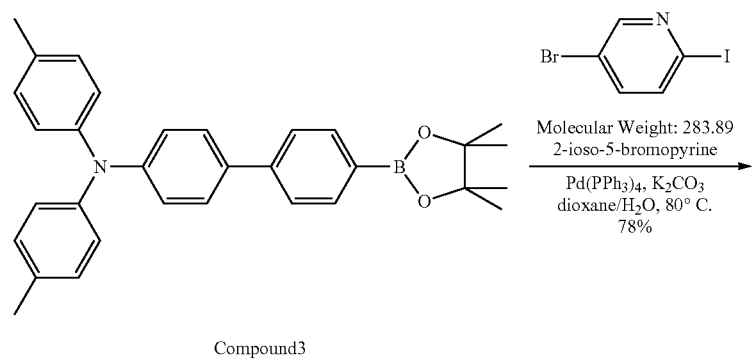
Compound3
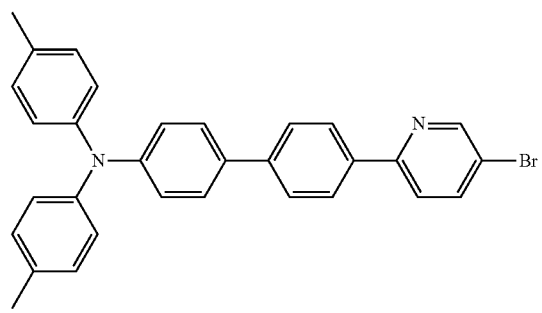
Compound 6
Molecular Weight: 475.43

4'-(5-bromopyridin-2-yl)-N,N-di-p-tolyl-[1,1'-biphenyl]-4-amine (Compound 6)

A mixture of 4'-(4,4,5,5-tetramethyl-1,3,2-dioxaborolan-2-yl)-N,N-di-p-tolyl-[1,1'-biphenyl]-4-amine (Compound 3) (1.82 g, 3.83 mmol), 2-iodo-5-bromopyrine (2.18 g, 7.7 mmol), $K_2CO_3$ (1.38 g, 10 mmol) and $Pd(PPh_3)_4$ (0.313 g, 0.27 mmol) in dioxane/water (80 mL/15 mL) was degassed, then heated at about 80° C. for 36 hours. The resulting mixture was cooled to RT. The yellow precipitate was filtered and collected (1.1 g). The filtrate was diluted with ethyl acetate (100 mL), washed with brine, dried over $Na_2SO_4$, loaded on silica gel and purified by flash column (hexanes to hexanes/ethyl acetate 40:1). The desired fraction was collected and concentrated, resulting in a yellow solid. This was filtered and washed with methanol to give a pale yellow solid (Compound 6) (0.40 g). Total amount obtained was 1.50 g in 77.6% yield.

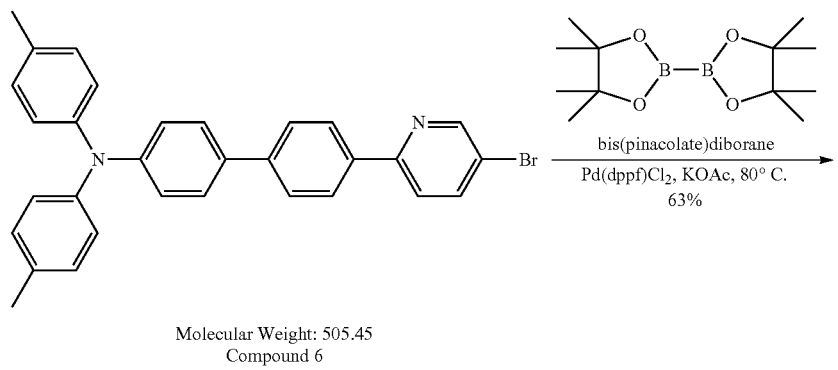

Molecular Weight: 505.45
Compound 6

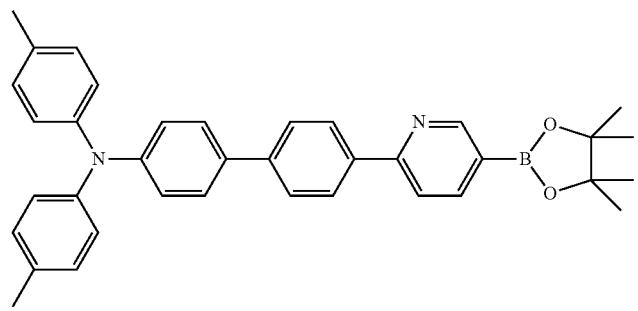

Compound 7

4'-(5-(4,4,5,5-tetramethyl-1,3,2-dioxaborolan-2-yl) pyridin-2-yl)-N,N-di-p-tolyl-[1,1'-biphenyl]-4-amine (Compound 7)

A mixture of 4'-(5-bromopyridin-2-yl)-N,N-di-p-tolyl-[1,1'-biphenyl]-4-amine (Compound 6) (1.454 g, 2.87 mmol), bis(pinacolate)diborane (0.762 g, 3.0 mmol), Pd(dppf)Cl$_2$ (0.22 g, 0.3 mmol) and KOAc (0.882 g, 9 mmol) in dioxane (50 mL) was degassed and heated at about 80° C. for 18 hours. The mixture was poured into ethyl acetate (300 mL), washed with brine, dried over Na$_2$SO$_4$, concentrated and loaded on silica gel, then purified by flash column (hexanes/ethyl acetate 10:1 to 2:1 to dichloromethane/ethyl acetate 10:1). The desired fraction was collected, dried under vacuum to give yellow oil (Compound 7) (1.0 g, in 63% yield).

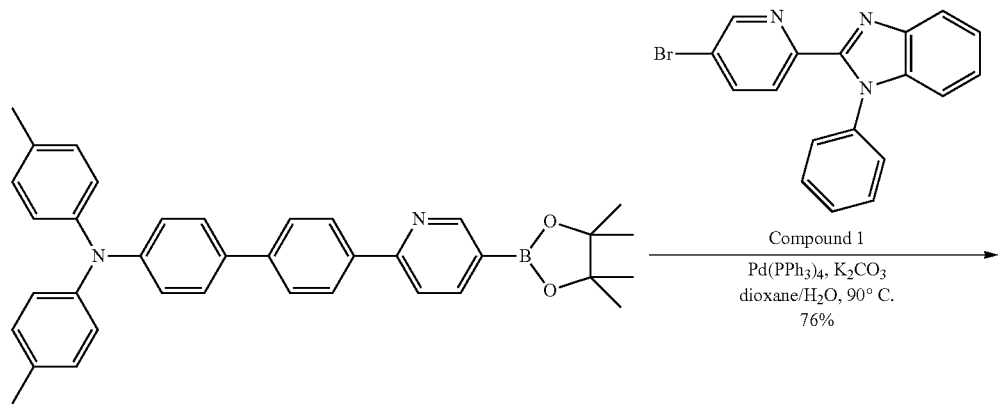

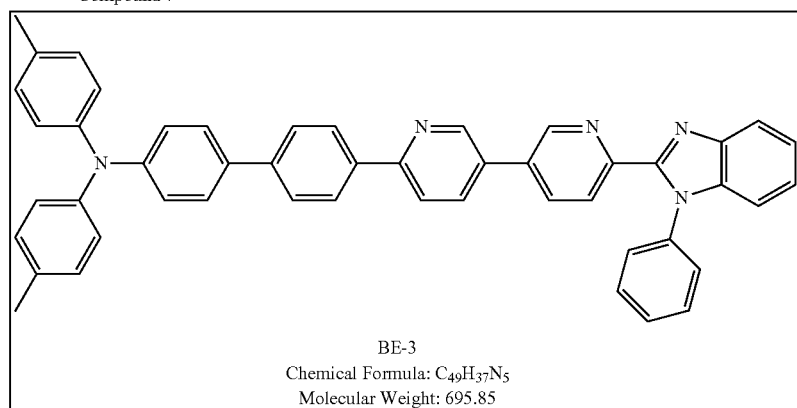

Compound BE-3

A mixture of 4'-(5-(4,4,5,5-tetramethyl-1,3,2-dioxaborolan-2-yl)pyridin-2-yl)-N,N-di-p-tolyl-[1,1'-biphenyl]-4-amine (Compound 7) (1.0 g, 1.8 mmol), 2-(5-bromopyridin-2-yl)-1-phenyl-1H-benzo[d]imidazole (Compound 1) (0.595 g, 1.7 mmol), K$_2$CO$_3$ (0.69 g, 5 mmol) and Pd(PPh$_3$)$_4$ (0.17 g, 0.15 mmol) in dioxane/water (50 mL/10 mL) was degassed and heated at about 90° C. for 18 hours. After being cooled to RT, a yellow precipitate formed. This was filtered, washed with methanol and dried in air. Then the solid was dissolved in dichloromethane (250 mL) and loaded on silica gel, then purified by flash column (dichloromethane to dichloromethane/ethyl acetate 9:1 to 4:1 to 7:3). After removal of solvent, a light yellow solid (Compound BE-3) was obtained (0.90 g, in 76% yield). LCMS (APCI+) was calculated for C$_{49}$H$_{38}$N$_5$ (M+H)=696. found: m/e=696.

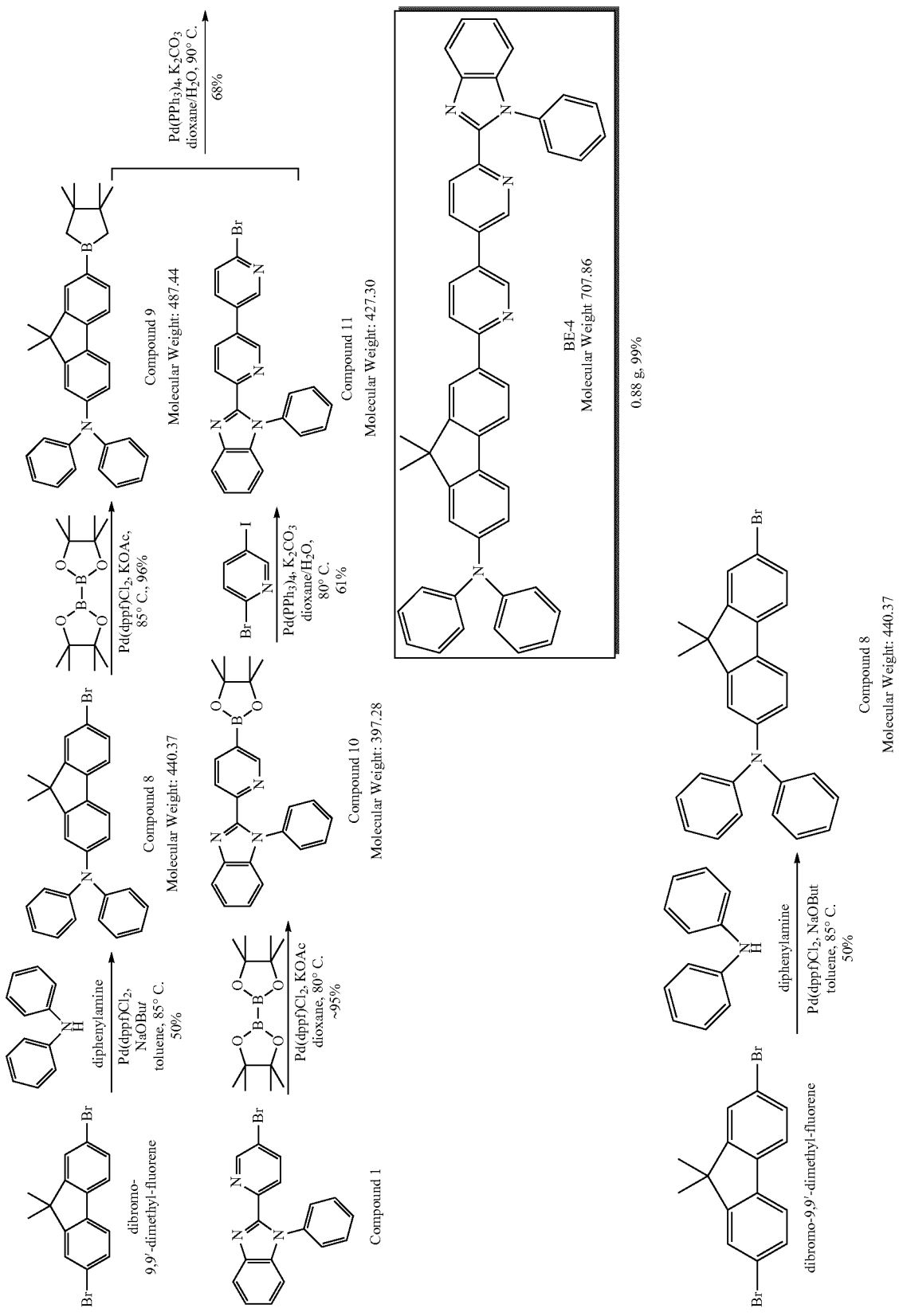

7-bromo-9,9-dimethyl-N,N-diphenyl-9H-fluoren-2-amine (Compound 8)

A mixture of diphenylamine (3.06 g, 20 mmol), dibromo-9,9'-dimethyl-fluorene (14.08 g, 40 mmol), sodium tert-butoxide (NaOBut) (3.84 g, 40 mmol) and Pd(dppf)Cl$_2$ (1.46 g, 2 mmol) in toluene (200 mL) was degassed and heated at about 85° C. for about 16 hours. The resulting mixture was mixed with water and extracted with ethyl acetate. The organic phase was collected, dried over Na$_2$SO$_4$, loaded on silica gel and purified by flash column (hexanes to hexanes/dichloromethane 30:1). The desired fraction was collected and a white solid (Compound 8) was obtained after removal of solvent (4.5 g, in 50% yield).

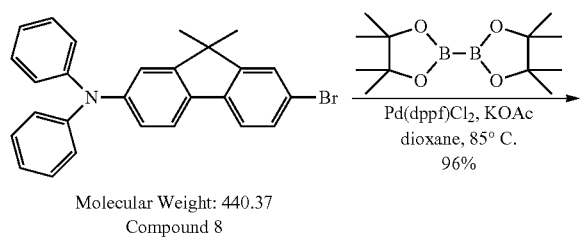

Molecular Weight: 440.37
Compound 8

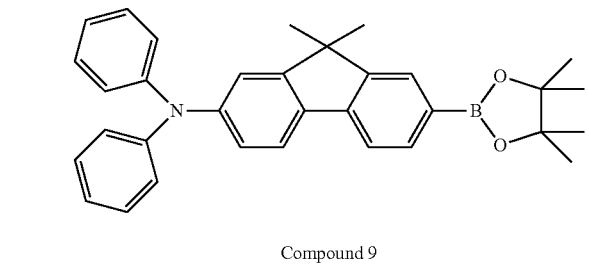

Compound 9

9,9-dimethyl-N,N-diphenyl-7-(4,4,5,5-tetramethyl-1,3,2-dioxaborolan-2-yl)-9H-fluoren-2-amine (Compound 9)

7-bromo-9,9-dimethyl-N,N-diphenyl-9H-fluoren-2-amine (Compound 8) (4.4 g, 10 mmol), bis(pinacolate)diborane (2.79 g, 11 mmol), Pd(dppf)Cl$_2$ (0.5 g, 0.68 mmol) and potassium acetate (2.94 g, 30 mmol) in dioxane (100 mL) was degassed and heated at about 85° C. for about 22 hours. After being cooled to RT, the whole was poured into ethyl acetate (200 mL), washed with water, then brine, dried over Na$_2$SO$_4$, loaded on silica gel and purified by flash column (hexanes to hexanes/ethyl acetate 10:1). The desired fraction was collected and removal of solvent gave a white solid (Compound 9) (4.7 g, in 96% yield).

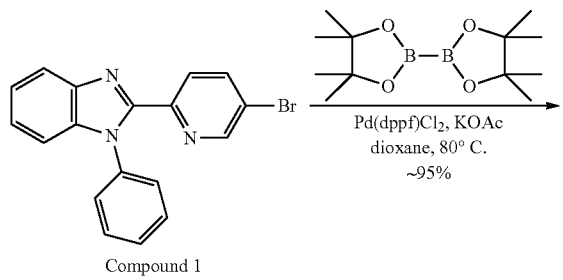

Compound 1

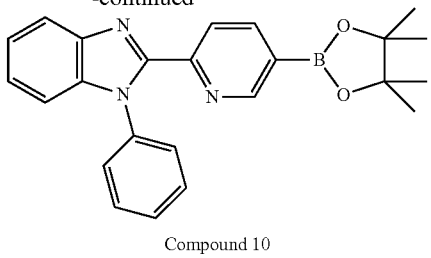

Compound 10

1-phenyl-2-(5-(4,4,5,5-tetramethyl-1,3,2-dioxaborolan-2-yl)pyridin-2-yl)-1H-benzo[d]imidazole (Compound 10)

A mixture of 2-(5-bromopyridin-2-yl)-1-phenyl-1H-benzo[d]imidazole (Compound 1) (1.048 g, 3 mmol), bis(pinacolate)diborane (0.787 g, 3.1 mmol), Pd(dppf)Cl$_2$ (0.219 g, 0.3 mmol) and potassium acetate (KOAc) (0.588 g, 6 mmol) in dioxane (50 mL) was degassed and heated at 80° C. for 18 hours. The whole was diluted with ethyl acetate (100 mL), washed with brine, and dried over Na$_2$SO$_4$. After removal of solvent, a brown solid (Compound 10) was obtained which was used in the next step without further purification.

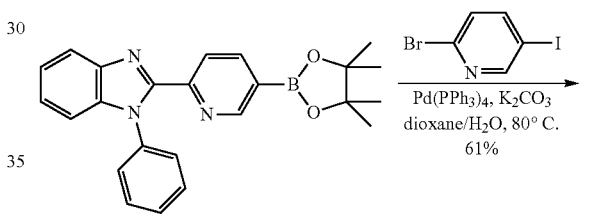

Molecular Weight: 397.28
Compound 10

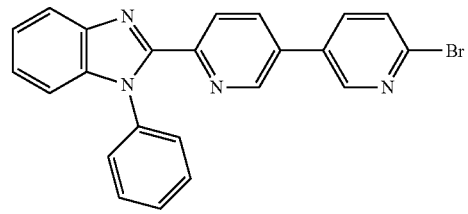

Compound 11

2-(6'-bromo-[3,3'-bipyridin]-6-yl)-1-phenyl-1H-benzo[d]imidazole (Compound 11)

A mixture of 1-phenyl-2-(5-(4,4,5,5-tetramethyl-1,3,2-dioxaborolan-2-yl)pyridin-2-yl)-1H-benzo[d]imidazole (3 mmol), 2-bromo-5-iodopyridine (1.98 g, 7 mmol) (Compound 10), Pd(PPh$_3$)$_4$ (0.346 g, 0.3 mmol) and potassium carbonate (0.828 g, 6 mmol) in dioxane/water (50 mL/10 mL) was degassed and heated at about 80° C. overnight. The mixture was poured into ethyl acetate (250 mL), washed with water, then brine, dried over Na$_2$SO$_4$, loaded on silica gel and purified by flash column (hexanes/dichloromethane 1:1 to dichloromethane to dichloromethane/ethyl acetate 9:1 to 4:1). The desired fraction was collected and concentrated, then filtered to give a light yellow solid (Compound 11) (0.78 g, in 61% yield).

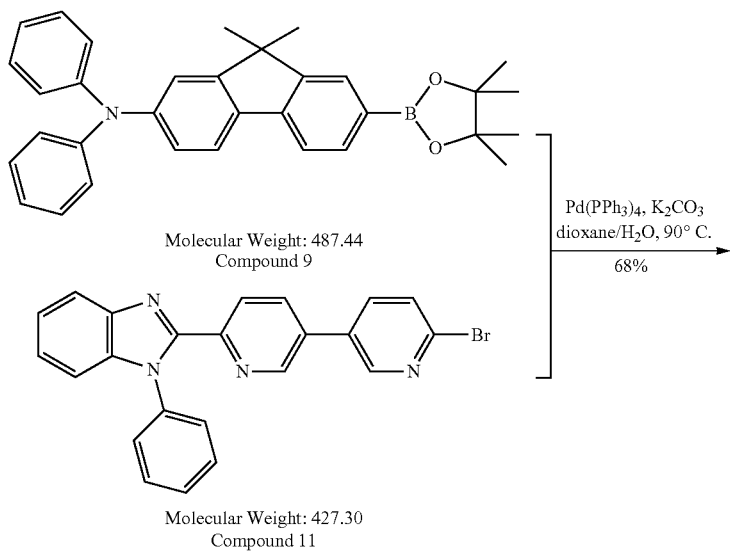

Compound BE-4

A mixture of 9,9-dimethyl-N,N-diphenyl-7-(4,4,5,5-tetramethyl-1,3,2-dioxaborolan-2-yl)-9H-fluoren-2-amine (0.892 g, 1.83 mmol) (Compound 9), 2-(6'-bromo-[3,3'-bipyridin]-6-yl)-1-phenyl-1H-benzo[d]imidazole (0.784 g, 1.83 mmol) (Compound 11), Pd(PPh$_3$)$_4$ (0.173 g, 0.15 mmol) and potassium carbonate (0.745 g, 5.4 mmol) in dioxane/water (50 mL/10 mL) was degassed and heated at about 90° C. for about 16 hours. After being cooled to RT, a yellow solid was collected by filtration, which was dissolved in dichloromethane (250 mL), and loaded on silica gel. Purification by flash column (dichloromethane to dichloromethane/ethyl acetate 9:1 to 4:1) gave a light yellow solid (Compound BE-4), after concentrating the solvent and filtration (0.88 g, in 68% yield). LCMS (APCI+) was calculated for C$_{50}$H$_{38}$N$_5$ (M+H)=708. found: m/e=708.

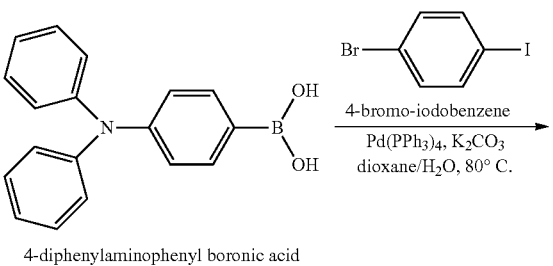

-continued
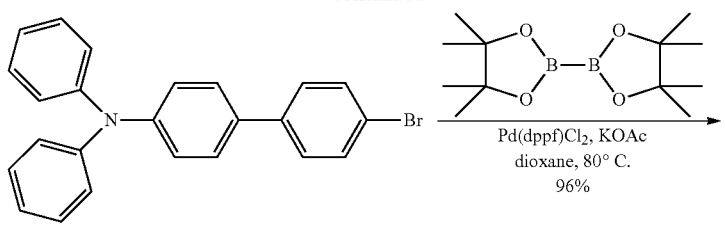
Molecular Weight: 400.31
Compound 12
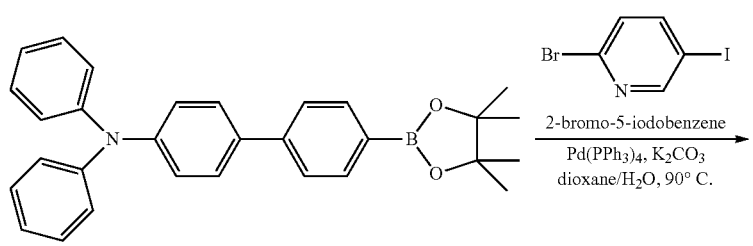
Molecular Weight: 447.38
Compound 13
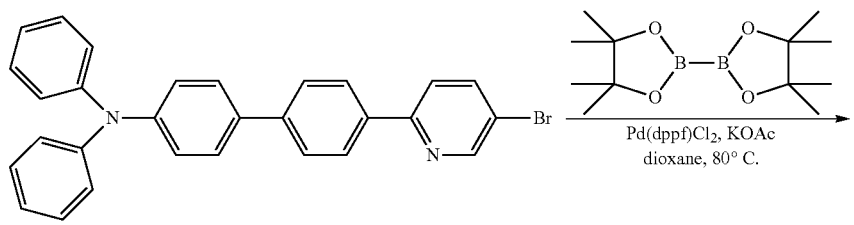
Compound 14
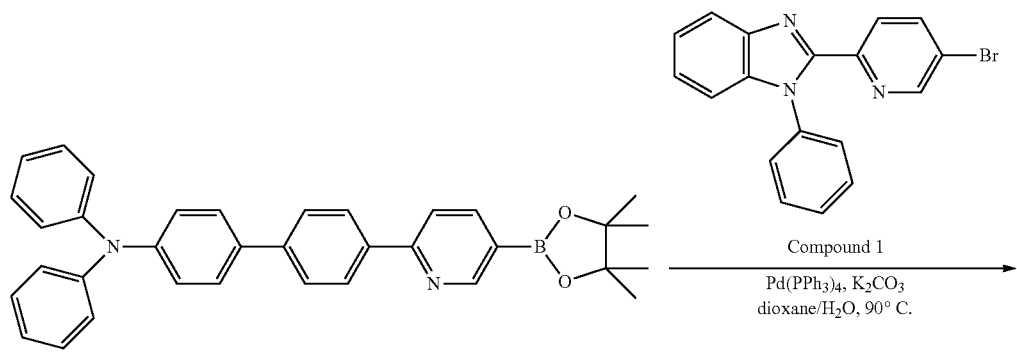
Compound 15
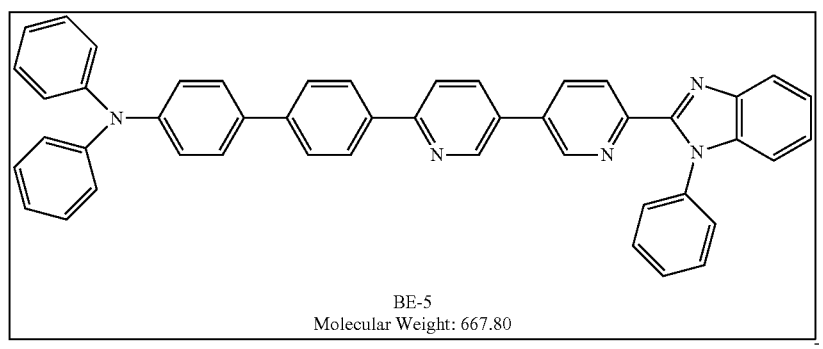
BE-5
Molecular Weight: 667.80

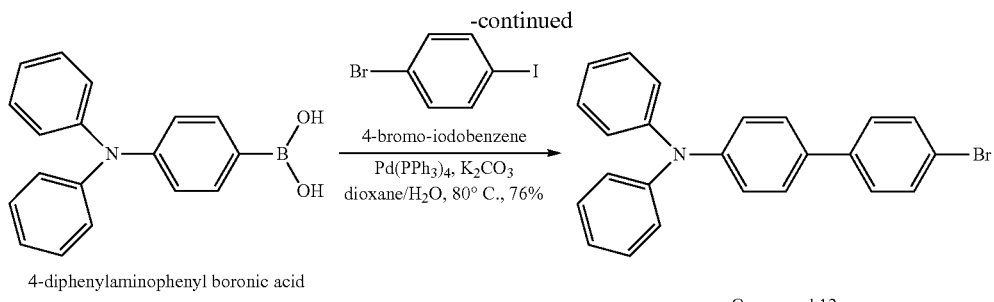

Compound 12

4'-bromo-N,N-diphenyl-[1,1'-biphenyl]-4-amine (Compound 12)

A mixture of 4-diphenylaminophenyl boronic acid (2.57 g, 8.9 mmol), 4-bromo-iodobenzene (5.03 g, 17.8 mmol), Pd(PPh$_3$)$_4$ (0.58 g, 0.5 mmol) and K$_2$CO$_3$ (3.0 g, 22 mmol) in dioxane/water (80 mL/15 mL) was degassed and heated at about 80° C. for about 20 hours. The whole was mixed with water/dichloromethane, the organic phase was collected and washed with brine, dried over Na$_2$SO$_4$, loaded on silica gel, and purified by flash column (hexanes to hexanes/dichloromethane 30:1). The desired fraction was collected, and concentrated to give a white solid (Compound 12), which was filtered and washed with methanol (2.70 g, in 76% yield).

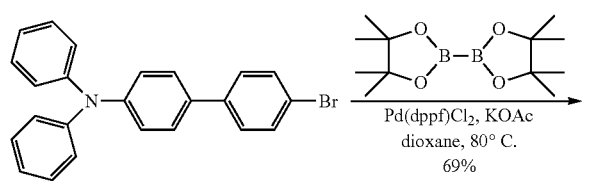

Molecular Weight: 400.31
Compound 12

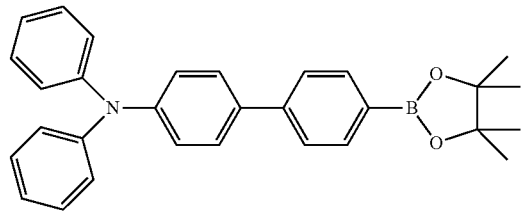

Compound 13

N,N-diphenyl-4'-(4,4,5,5-tetramethyl-1,3,2-dioxaborolan-2-yl)-[1,1'-biphenyl]-4-amine (Compound 13)

A mixture of 4'-bromo-N,N-diphenyl-[1,1'-biphenyl]-4-amine (Compound 12) (2.636 g, 6.6 mmol), bis(pinacolato) diborane (1.78 g, 7 mmol), Pd(dppf)Cl$_2$ (0.24 g, 0.33 mmol) and KOAc (1.47 g, 15 mmol) in dioxane (50 mL) was degassed and heated at about 80° C. for about 16 hours. The resulting mixture was poured into ethyl acetate (250 mL), washed with brine, dried over Na$_2$SO$_4$, loaded on silica gel, and purified by flash column (hexanes to hexanes/dichloromethane 30:1 to hexanes/ethyl acetate 9:1). The desired fraction was collected. After removal of solvent, a white solid (Compound 13) was obtained (2.05 g, in 69% yield).

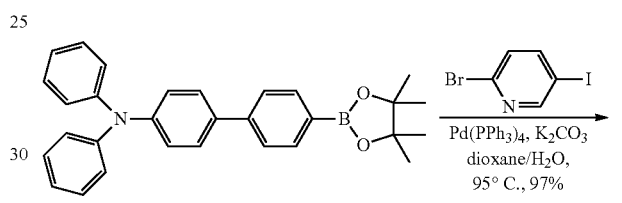

Molecular Weight: 447.38
Compound 13

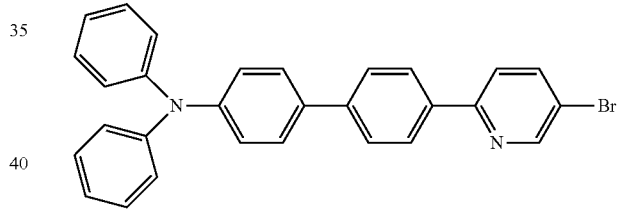

Compound 14

4'-(5-bromopyridin-2-yl)-N,N-diphenyl-[1,1'-biphenyl]-4-amine (Compound 14)

A mixture of N,N-diphenyl-4'-(4,4,5,5-tetramethyl-1,3,2-dioxaborolan-2-yl)-[1,1'-biphenyl]-4-amine (Compound 13) (1.0 g, 2.24 mmol), 2-bromo-5-iodopyridine (1.4 g, 4.9 mmol), Pd(PPh$_3$)$_4$ (0.2 g, 0.18 mmol) and K$_2$CO$_3$ (0.69 g, 5 mmol) in dioxane/water (30 mL/6 mL) was degassed, then heated at about 95° C. for about 24 hours. The mixture was allowed to cool to RT, and a yellow solid precipitated, which was filtered and dried under vacuum to give the desired product (Compound 14) (1.03 g, in 97% yield).

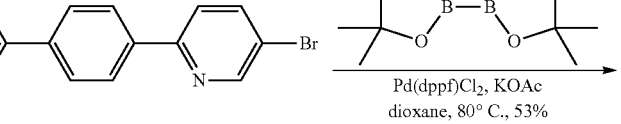

Compound 14

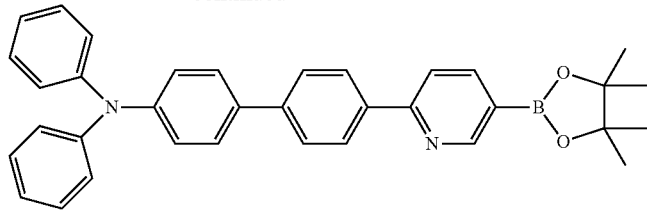

Compound 15

N,N-diphenyl-4'-(5-(4,4,5,5-tetramethyl-1,3,2-dioxaborolan-2-yl)pyridin-2-yl)-[1,1'-biphenyl]-4-amine (Compound 15)

A mixture of 4'-(5-bromopyridin-2-yl)-N,N-diphenyl-[1,1'-biphenyl]-4-amine (Compound 14) (1.03 g, 2.16 mmol), bis(pinacolate)diborane (0.584 g, 2.3 mmol), Pd(dppf)Cl$_2$ (0.1 g, 0.14 mmol) and KOAc (0.49 g, 5 mmol) in dioxane (50 mL) was degassed and heated at about 80° C. for about 15 hours. The mixture was poured into ethyl acetate (150 mL). After filtration, the solution was loaded on silica gel and purified by flash column (hexanes/dichloromethane 1:1 to dichloromethane to dichloromethane/ethyl acetate 4:1 to 2:1 to ethyl acetate). The desired fraction was collected and concentrated to give an oil (Compound 15) (0.6 g, in 53% yield).

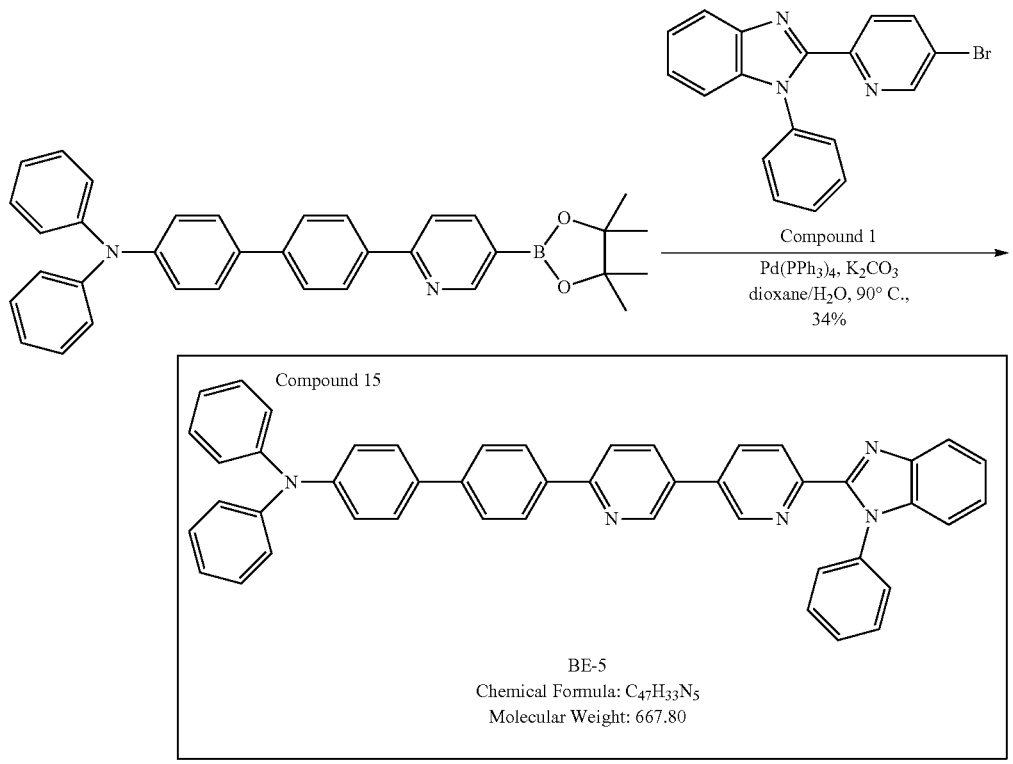

Compound BE-5

A mixture of N,N-diphenyl-4'-(5-(4,4,5,5-tetramethyl-1,3,2-dioxaborolan-2-yl)pyridin-2-yl)-[1,1'-biphenyl]-4-amine (0.6 g, 1.1 mmol) (Compound 15), 2-(6'-bromo-[3,3'-bipyridin]-6-yl)-1-phenyl-1H-benzo[d]imidazole (Compound 1) (0.35 g, 1.1 mmol), Pd(PPh$_3$)$_4$ (58 mg, 0.05 mmol) and K$_2$CO$_3$ (0.55 g, 4 mmol) in dioxane/water (30 mL/6 mL) was degassed and heated at 90° C. for 15 hours. After cooling to RT, the mixture was diluted with dichloromethane (100 mL), washed with brine, dried over Na$_2$SO$_4$, loaded on silica gel and purified by flash column (dichloromethane to dichloromethane/ethyl acetate 8:1 to 4:1 to 2:1). The desired fraction was collected, concentrated and filtered to give a light yellow solid (Compound BE-5) (0.25 g, in 34% yield). LCMS (APCI+) was calculated for C$_{47}$H$_{34}$N$_5$ (M+H)=668. found: m/e=668.

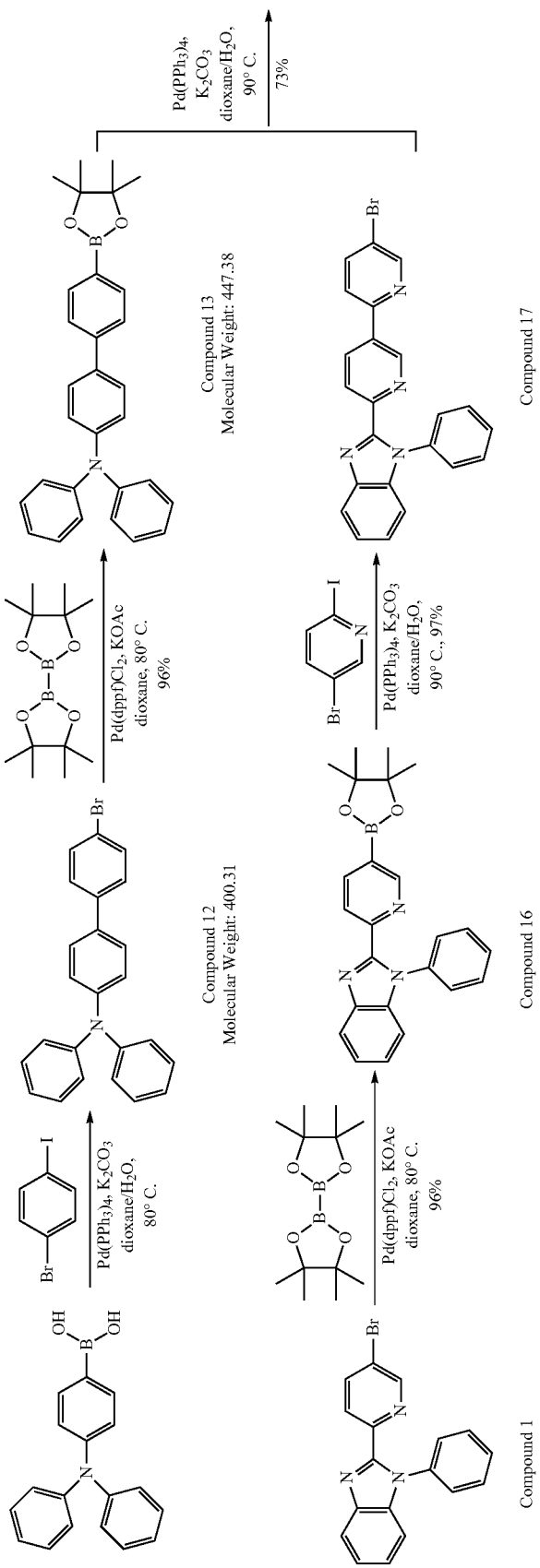

-continued
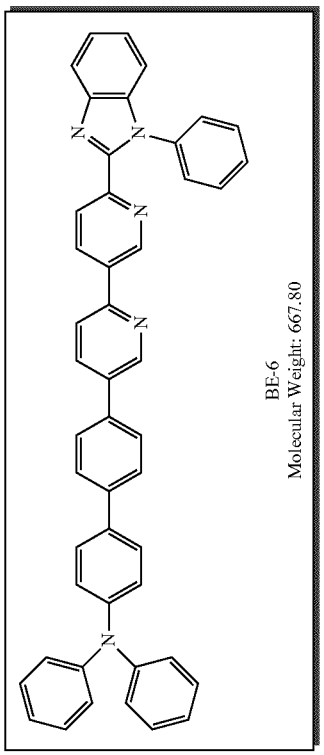
BE-6
Molecular Weight: 667.80
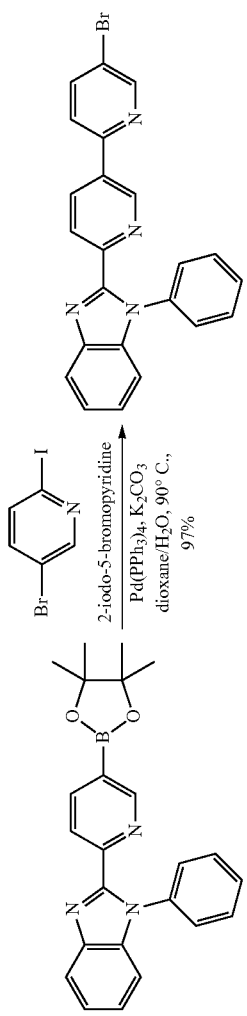

2-(5-bromo-[2,3'-bipyridin]-6'-yl)-1-phenyl-1H-benzo[d]imidazole (Compound 17)

A mixture of 1-phenyl-2-(5-(4,4,5,5-tetramethyl-1,3,2-dioxaborolan-2-yl)pyridin-2-yl)-1H-benzo[d]imidazole (Compound 16) (12 mmol), 2-iodo-5-bromo pyridine (6.816 g, 24 mmol), Pd(PPh$_3$)$_4$ (0.69 g, 0.6 mmol) and K$_2$CO$_3$ (3.3 g, 24 mmol) in dioxane/water (100 mL/20 mL) was degassed and heated at 90° C. for 20 hours. The whole was allowed to cool to RT, white precipitate formed. After filtration, a solid (Compound 17) was collected (5.0 g, in 97% yield).

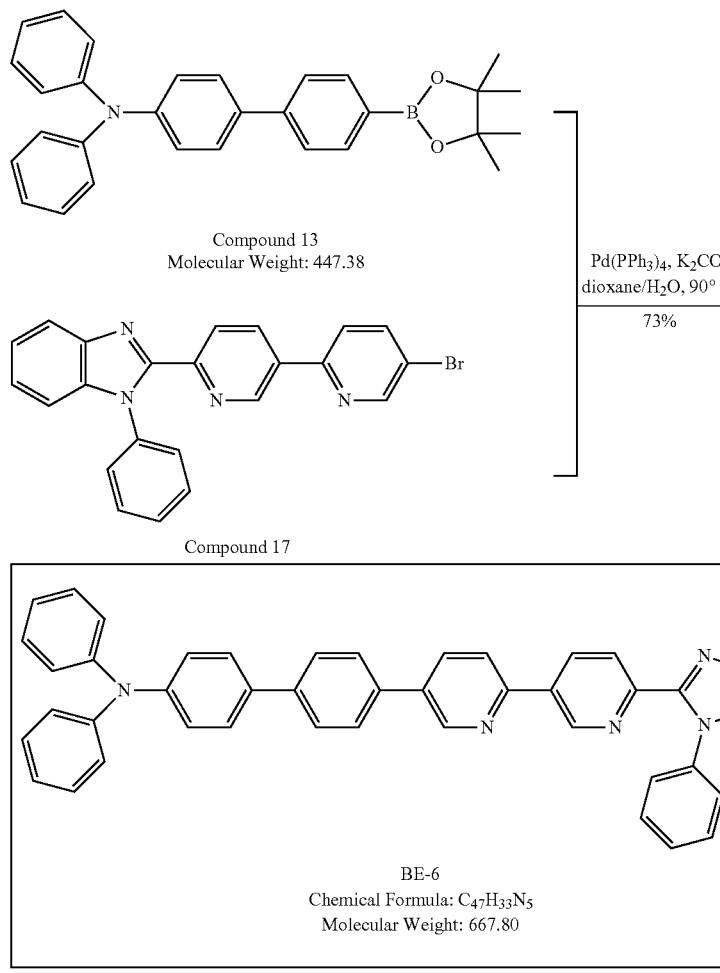

Compound BE-6

A mixture of N,N-diphenyl-4'-(4,4,5,5-tetramethyl-1,3,2-dioxaborolan-2-yl)-[1,1'-biphenyl]-4-amine (Compound 13) (0.90 g, 2 mmol), 2-(5-bromo-[2,3'-bipyridin]-6'-yl)-1-phenyl-1H-benzo[d]imidazole (Compound 17) (0.86 g, 2 mmol), Pd(PPh$_3$)$_4$ (0.12 g, 0.1 mmol) and K$_2$CO$_3$ (0.55 g, 4 mmol) in dioxane/water (40 mL/8 mL) was degassed and heated at 90° C. for 15 hours. The mixture was allowed to cool to RT, and a yellow solid precipitated. After filtration, the solid was washed with methanol, dried in air, then dissolved in dichloromethane (150 mL). The solution was loaded on silica gel and purified by flash column (hexanes/dichloromethane 1:1 to dichloromethane to dichloromethane/ethyl acetate 8:1 to 4:1). The desired fraction was collected, concentrated and recrystallized in dichloromethane/methanol to give a yellow solid (Compound BE-6) (0.98 g, in 73% yield). LCMS (APCI+) was calculated for C$_{47}$H$_{34}$N$_5$ (M+H)=668. found: m/e=668.

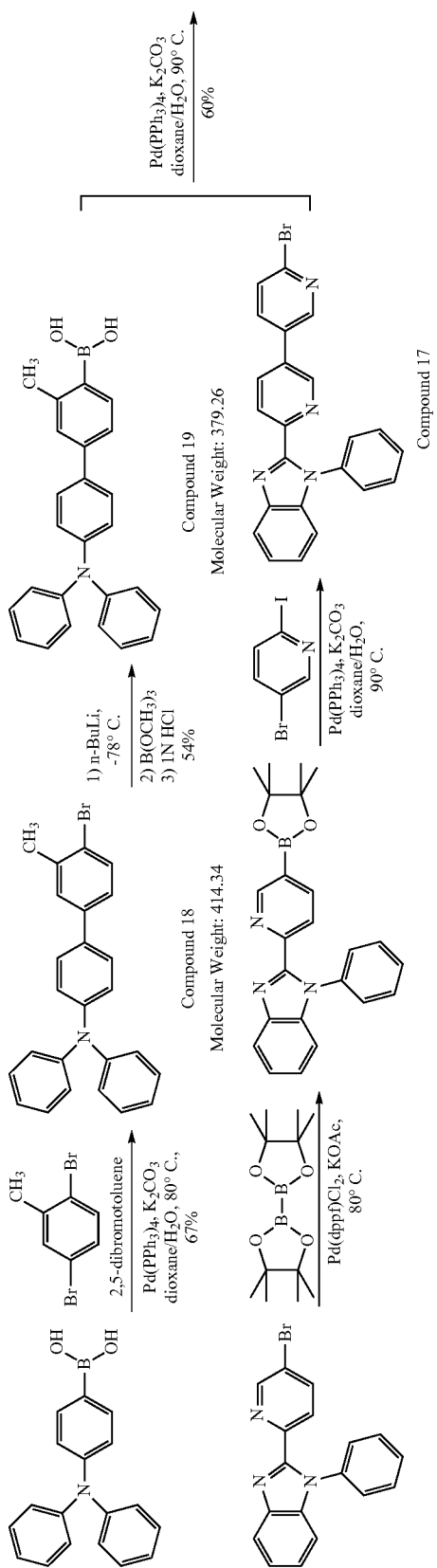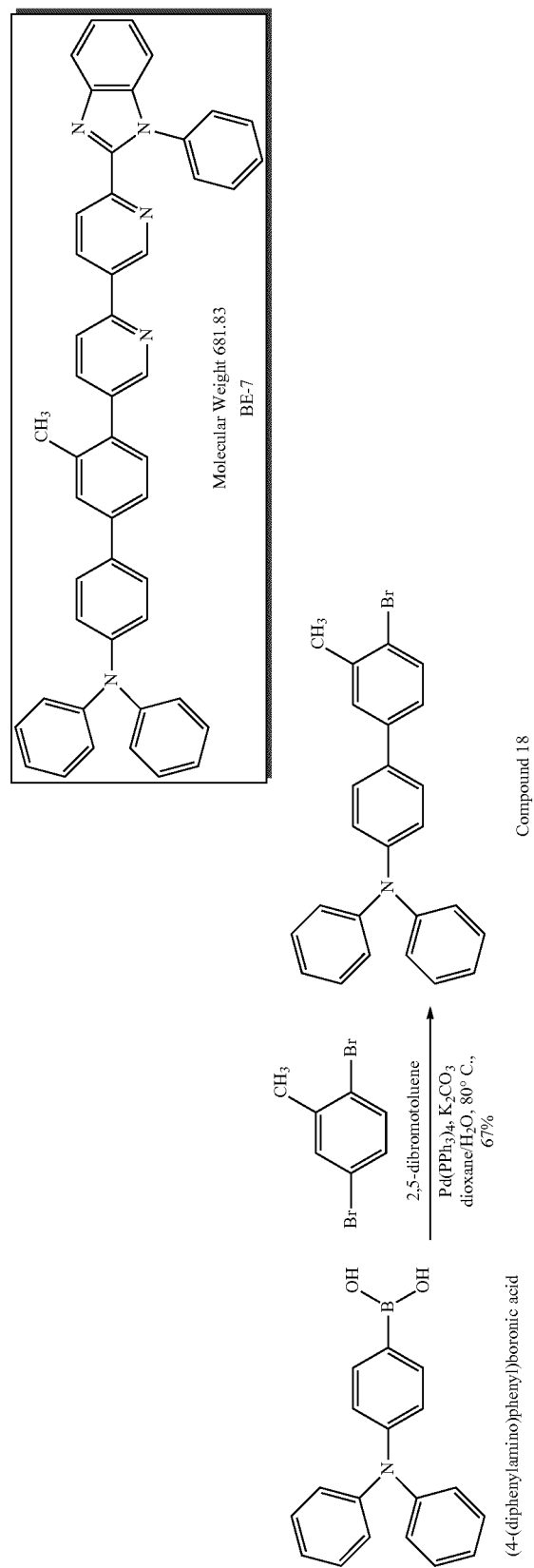

4'-bromo-3'-methyl-N,N-diphenyl-[1,1'-biphenyl]-4-amine (Compound 18)

A mixture of 4-diphenylaminophenyl boronic acid (1.25 g, 4.33 mmol), 2,5-dibromotoluene (2.16 g, 8.65 mmol), Pd(PPh$_3$)$_4$ (0.25 g, 0.22 mmol) and K$_2$CO$_3$ (1.38 g, 10 mmol) in dioxane/water (50 mL/9 mL) was degassed and heated at 80° C. for 15 hours. The resulting mixture was mixed with ethyl acetate/brine. The organic phase was dried over Na$_2$SO$_4$, loaded on silica gel, and purified by flash column (hexanes to hexanes/dichloromethane 9:1 to 4:1). The desired fraction was collected and concentrated. After removal of solvent, a white solid (Compound 18) was obtained (1.2 g, in 67% yield).

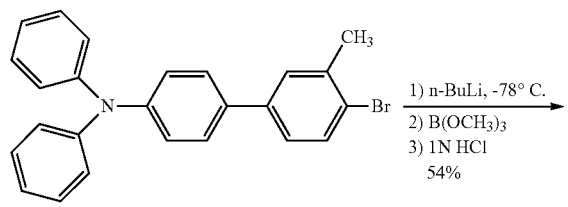

Compound 18

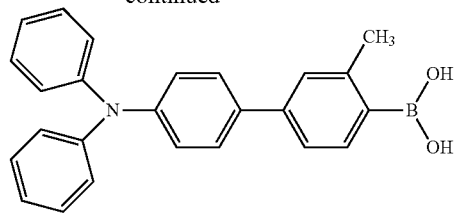

Compound 19
Molecular Weight: 414.34

(4'-(diphenylamino)-3-methyl-[1,1'-biphenyl]-4-yl) boronic acid (Compound 19)

To a solution of 4'-bromo-3'-methyl-N,N-diphenyl-[1,1'-biphenyl]-4-amine (Compound 18) (1.2 g, 2.9 mmol) in THF (25 mL), was added n-butyllithium (n-BuLi) solution (2.5M, 1.6 mL) at −78° C. The mixture was stirred at −78° C. for about one hour, then a freshly distilled trimethyl borate B(OCH$_3$)$_3$ (0.56 mL, 5 mmol) was added. The resulting mixture was stirred at RT for about one hour, then 1N HCl aqueous solution (50 mL) was added and stirred at RT overnight. The whole was mixed with dichloromethane/brine, extracted with dichloromethane (100 mL×2). The organic phase was dried over Na$_2$SO$_4$, loaded on silica gel, and purified by flash column (hexanes/dichloromethane 1:1 to dichloromethane to dichloromethane/ethyl acetate 4:1 to ethyl acetate/methanol 4:1). The desired fraction was collected, and solvent was removed under reduced pressure to give a white solid (Compound 19) (0.60 g, in 54% yield).

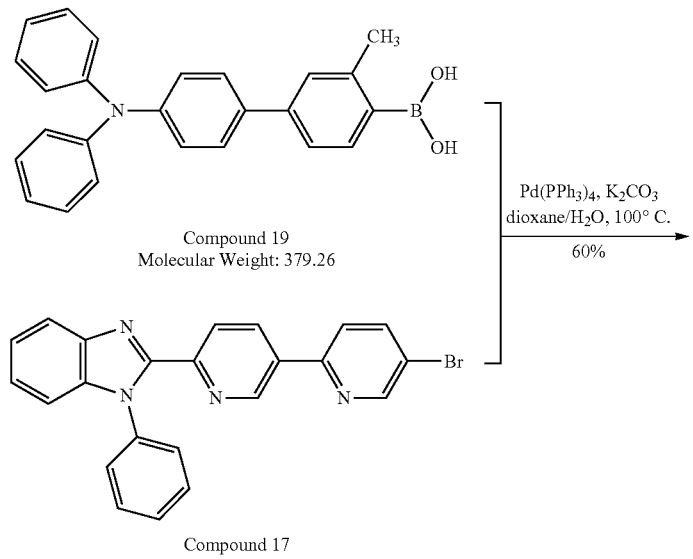

Compound 17

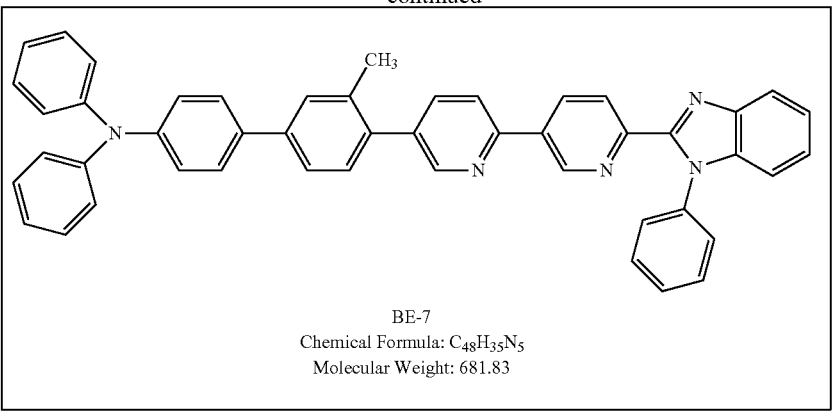

BE-7
Chemical Formula: C$_{48}$H$_{35}$N$_5$
Molecular Weight: 681.83

Compound BE-7

A mixture of (4'-(diphenylamino)-3-methyl-[1,1'-biphenyl]-4-yl)boronic acid (Compound 19) (0.60 g, 1.58 mmol), 2-(5-bromo-[2,3'-bipyridin]-6'-yl)-1-phenyl-1H-benzo[d]imidazole (Compound 17) (0.86 g, 2 mmol), Pd(PPh$_3$)$_4$ (0.20 g, 0.17 mmol) and K$_2$CO$_3$ (0.65 g, 4.7 mmol) in dioxane/water (30 mL/6 mL) was degassed and heated at 100° C. for 15 hours. The mixture was mixed with dichloromethane/brine, dried over Na$_2$SO$_4$, loaded on silica gel, and purified by flash column (dichloromethane to dichloromethane/ethyl acetate 8:1 to 4:1). The desired fraction was collected and concentrated, and recrystallized in dichloromethane/methanol to give a yellow solid (Compound BE-7) (0.64 g, in 60% yield). LCMS (APCI+) was calculated for C$_{48}$H$_{36}$N$_5$ (M+H)= 682. found: m/e=682.

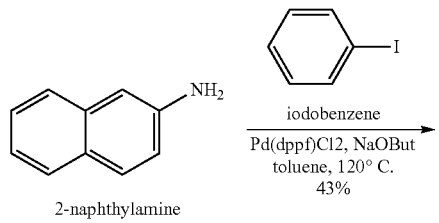

2-naphthylamine

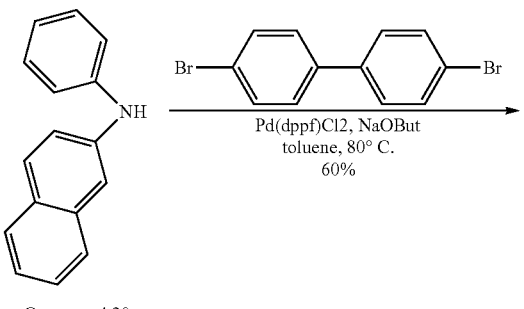

Compound 20

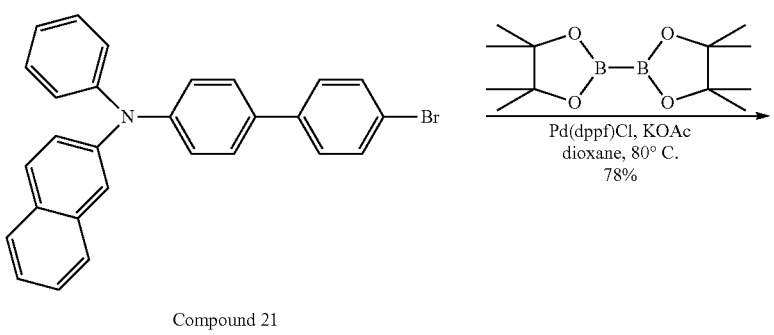

Compound 21

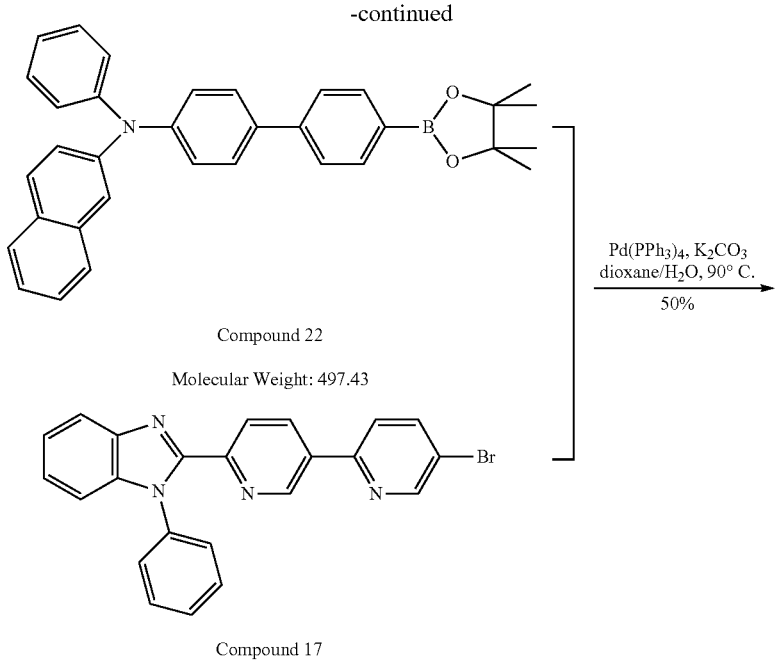

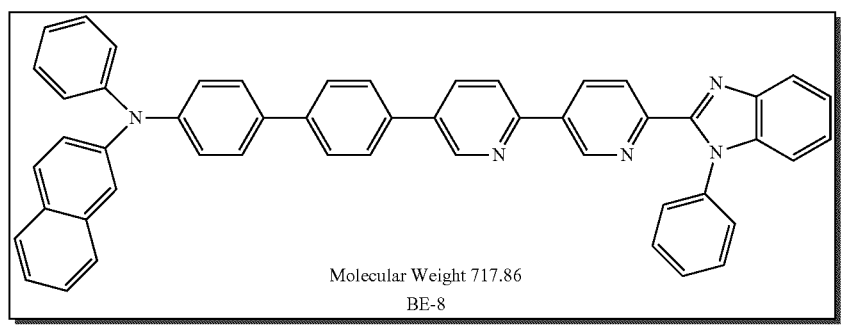

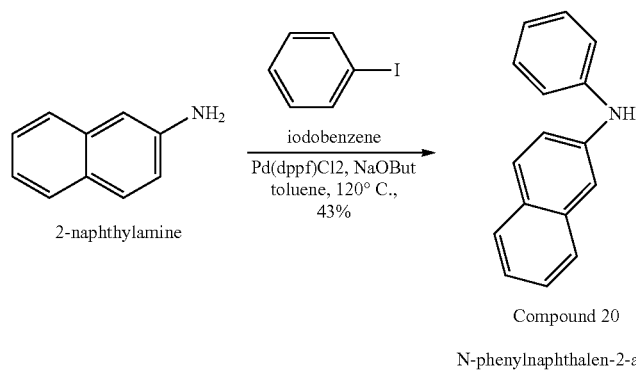

N-phenylnaphthalen-2-amine (Compound 20)

A mixture of 2-naphthylamine (8.0 g, 55.9 mmol), iodobenzene (12.24 g, 60 mmol), Pd(dppf)Cl$_2$ (0.731 g, 1 mmol) and sodium tert-butoxide (NaOBut) (5.76 g, 60 mmol) in toluene (200 mL) was degassed and heated at 120° C. overnight. The whole was poured into ethyl acetate (250 mL), washed with brine, dried over Na$_2$SO$_4$, loaded on silica gel and purified by flash column (hexanes to hexanes/dichloromethane 10:1). The desired fraction was collected, and concentrated. A white solid precipitated, which was filtered to give the product (Compound 20) (5.30 g, in 43% yield).

lected, and concentrated. The resulting solid was filtered, and washed with methanol to give a white solid (Compound 21) (6.15 g, in 60% yield).

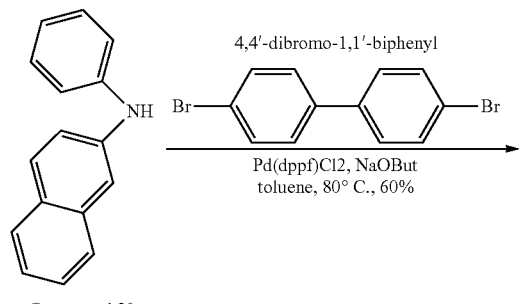

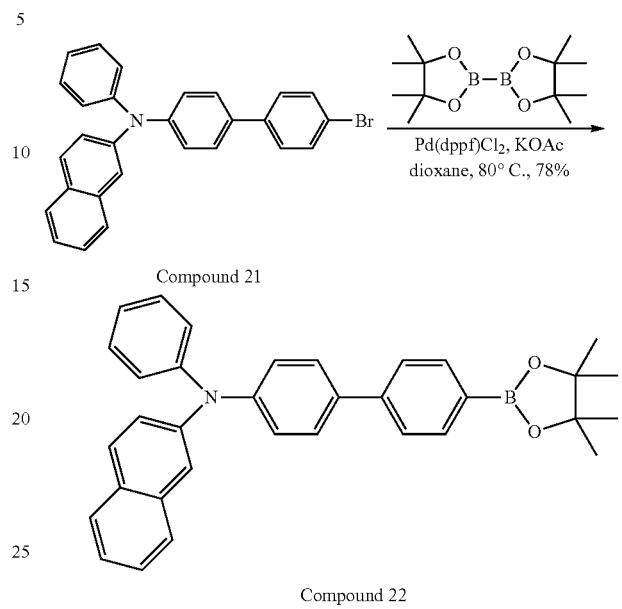

N-(4'-bromo-[1,1'-biphenyl]-4-yl)-N-phenylnaphthalen-2-amine (Compound 21)

A mixture of N-phenylnaphthalen-2-amine (Compound 20) (5.0 g, 22.8 mmol), 4,4'-dibromobiphenyl (17.8 g, 57 mmol), Pd(dppf)Cl₂ (0.73 g, 1 mmol) and sodium tert-butoxide (2.4 g, 25 mmol) in toluene (250 mL) was degassed and heated at 80° C. overnight. The whole was poured into ethyl acetate (250 mL), washed with brine, dried over Na₂SO₄, loaded on silica gel and purified by flash column (hexanes to hexanes/dichloromethane 9:1). The desired fraction was col-

N-phenyl-N-(4'-(4,4,5,5-tetramethyl-1,3,2-dioxaborolan-2-yl)-[1,1'-biphenyl]-4-yl)naphthalen-2-amine (Compound 22)

A mixture of N-(4'-bromo-[1,1'-biphenyl]-4-yl)-N-phenylnaphthalen-2-amine (Compound 21) (6.10 g, 13.6 mmol), bis(pinacolate)diborane (3.81 g, 15 mmol), Pd(dppf)Cl₂ (0.73 g, 1 mmol) and KOAc (5.0 g, 50 mmol) in dioxane (200 mL) was degassed and heated at 80° C. overnight. The mixture was poured into ethyl acetate (250 mL), washed with brine, dried over Na₂SO₄, loaded on silica gel, and purified by flash column (hexanes to hexanes/ethyl acetate 9:1). The desired fraction was collected, and concentrated. The resulting precipitate was filtered, and washed with methanol to give a white solid (Compound 22) (5.25 g, in 78% yield).

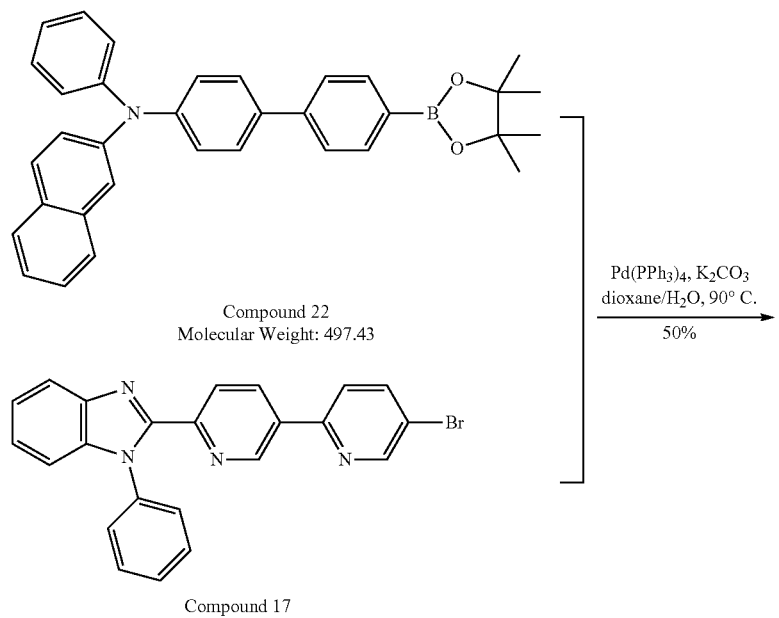

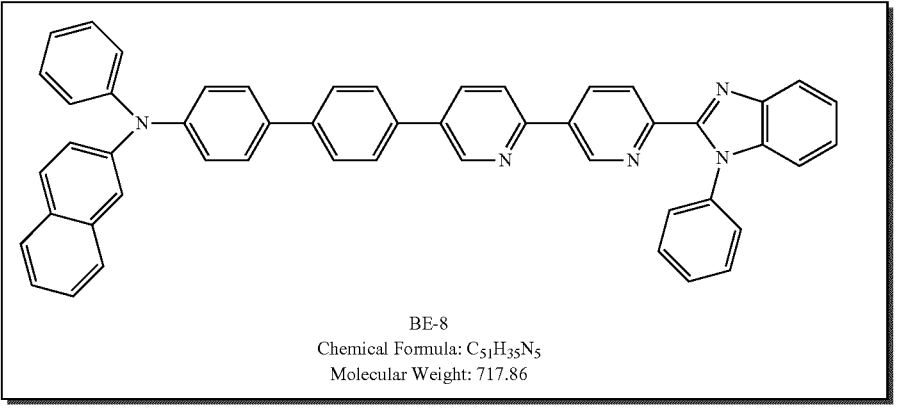

BE-8
Chemical Formula: $C_{51}H_{35}N_5$
Molecular Weight: 717.86

Compound BE-8

A mixture of N-phenyl-N-(4'-(4,4,5,5-tetramethyl-1,3,2-dioxaborolan-2-yl)-[1,1'-biphenyl]-4-yl)naphthalen-2-amine (Compound 22) (0.907 g, 1.82 mmol), 2-(5-bromo-[2,3'-bipyridin]-6'-yl)-1-phenyl-1H-benzo[d]imidazole (Compound 17) (1.4 g, 3.2 mmol), Pd(PPh$_3$)$_4$ (0.20 g, 0.17 mmol) and K$_2$CO$_3$ (0.552 g, 4 mmol) in dioxane/water (50 mL/9 mL) was degassed and heated at 90° C. for 30 hours. The resulting mixture was mixed with dichloromethane/brine. The organic phase was dried over Na$_2$SO$_4$, loaded on silica gel, and purified by flash column (dichloromethane to dichloromethane/ethyl acetate 9:1 to 4:1). The desired yellow emission fraction was collected, and concentrated. The solid was recrystallized in dichloromethane/methanol to give a yellow solid (Compound BE-8) (0.65 g, in 50% yield). LCMS (APCI+) was calculated for $C_{51}H_{36}N_5$ (M+H)=718. found: m/e=718.

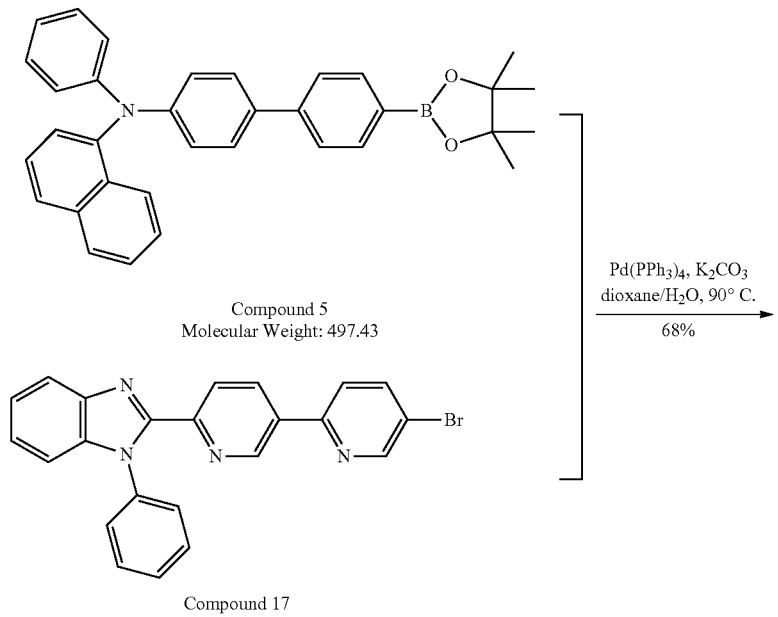

Compound 5
Molecular Weight: 497.43

Pd(PPh$_3$)$_4$, K$_2$CO$_3$
dioxane/H$_2$O, 90° C.
68%

Compound 17

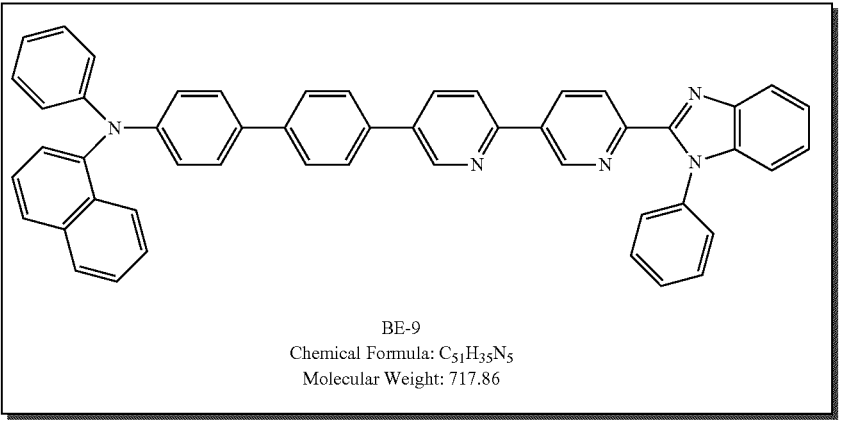

BE-9
Chemical Formula: $C_{51}H_{35}N_5$
Molecular Weight: 717.86

Compound BE-9

A mixture of N-phenyl-N-(4'-(4,4,5,5-tetramethyl-1,3,2-dioxaborolan-2-yl)-[1,1'-biphenyl]-4-yl)naphthalen-1-amine (Compound 5) (0.737 g, 1.48 mmol), 2-(5-bromo-[2,3'-bipyridin]-6'-yl)-1-phenyl-1H-benzo[d]imidazole (Compound 17) (1.27 g, 3 mmol), Pd(PPh$_3$)$_4$ (0.17 g, 0.147 mmol) and K$_2$CO$_3$ (0.552 g, 4 mmol) in dioxane/water (50 mL/10 mL) was degassed and heated at 90° C. for 16 hours. The mixture was mixed with dichloromethane/brine, dried over Na$_2$SO$_4$, loaded on silica gel, and purified by flash column (dichloromethane to dichloromethane/ethyl acetate 9:1 to 4:1). The desired yellow green emissive fraction was collected, and concentrated. Reprecipitation in dichloromethane/methanol gave a yellow solid (Compound BE-9) (0.72 g, in 68% yield). LCMS (APCI+) was calculated for $C_{51}H_{36}N_5$ (M+H)=718. found: m/e=718.

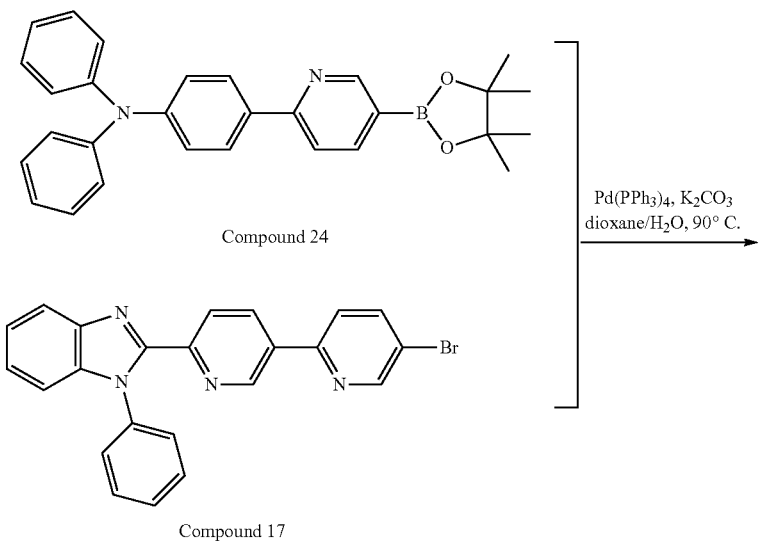

Compound 24

Pd(PPh$_3$)$_4$, K$_2$CO$_3$
dioxane/H$_2$O, 90° C.

Compound 17

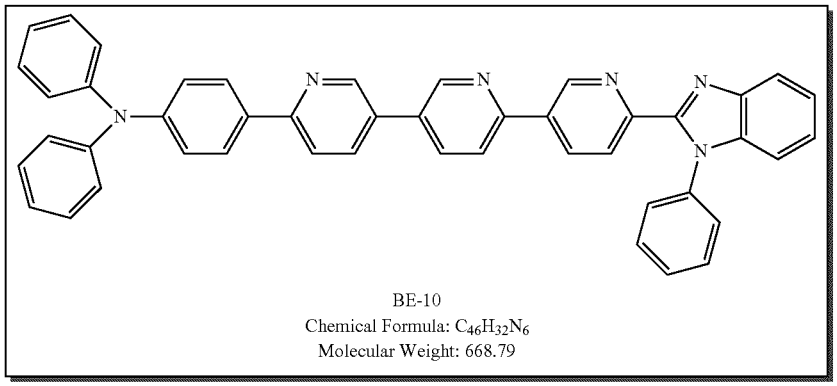

BE-10
Chemical Formula: $C_{46}H_{32}N_6$
Molecular Weight: 668.79

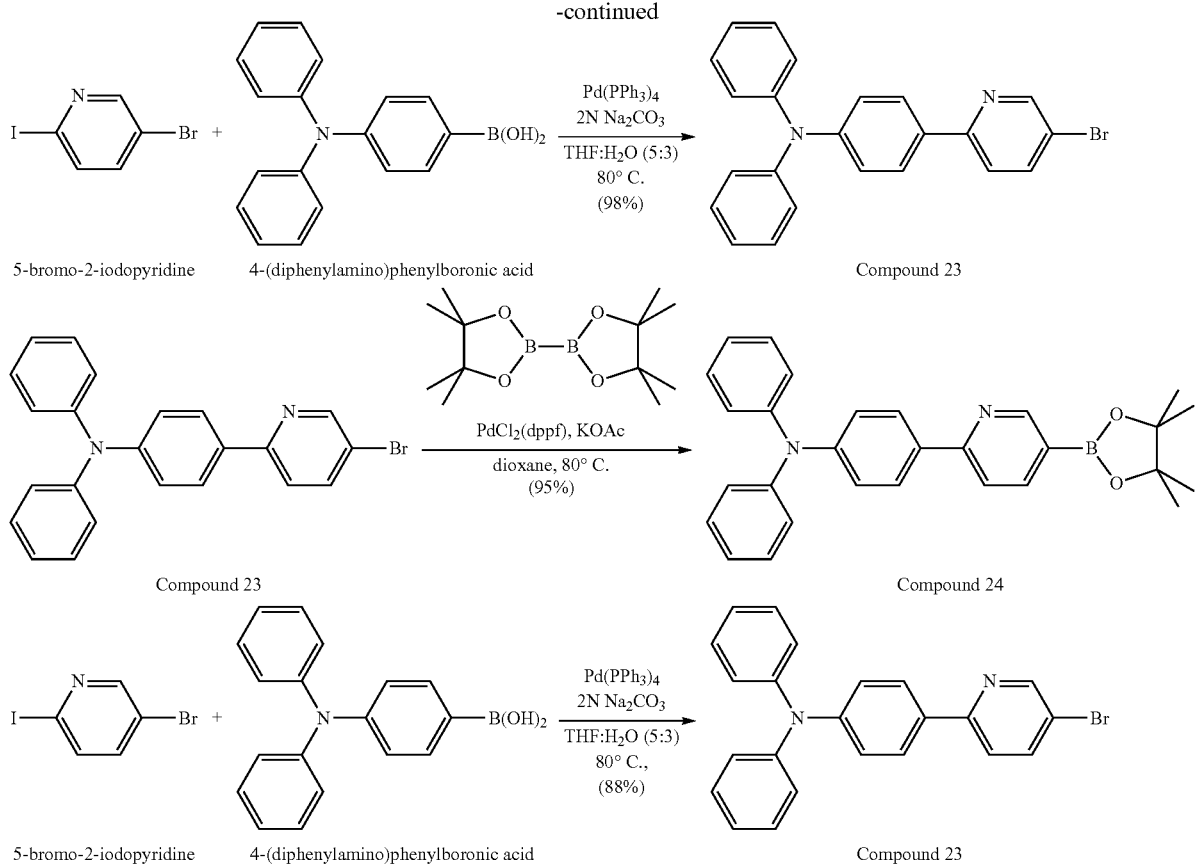

4-(5-bromopyridin-2-yl)-N,N-diphenylaniline (Compound 23)

A mixture of 4-(diphenylamino)phenylboronic acid (7.00 g, 24.2 mmol), 5-bromo-2-iodopyridine (7.56 g, 26.6 mmol), tetrakis(triphenylphosphine)palladium(0) (1.40 g, 1.21 mmol), $Na_2CO_3$ (9.18 g, 86.6 mmol), $H_2O$ (84 mL) and tetrahydrofuran (THF) (140 mL) was degassed with argon for about 1.5 h. while stirring. The stirring reaction mixture was then maintained under argon at 80° C. for about 19 h. Upon confirming consumption of the starting material by thin layer chromatography (TLC) ($SiO_2$, 19:1 hexanes-EtOAc), the reaction was cooled to RT and poured over EtOAc (500 mL). The organics were then washed with saturated sodium bicarbonate ($NaHCO_3$, $H_2O$) and brine, dried over $MgSO_4$, filtered and concentrated in vacuo. The crude product was then purified via flash chromatography ($SiO_2$, 2:1 hexanes-dichloromethane) to afford Compound 23 (9.54 g, 98% yield) as a light yellow, crystalline solid.

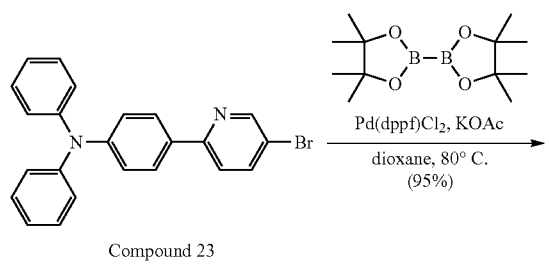

N,N-diphenyl-4-(5-(4,4,5,5-tetramethyl-1,3,2-dioxaborolan-2-yl)pyridin-2-yl)aniline (Compound 24)

A mixture of Compound 23 (6.00 g, 15.0 mmol), bis(pinacolato)diboron (4.18 g, 16.4 mmol), [1,1'-bis(diphenylphosphino)-ferrocene]dichloropalladium(II) (0.656 g, 0.897 mmol), potassium acetate (4.40 g, 44.9 mmol) and anhydrous 1,4-dioxane (90 mL) was degassed with argon for about 50 min. while stirring. The stirring reaction mixture was then maintained under argon at 80° C. for about 67 h. Upon confirming consumption of the starting material by TLC ($SiO_2$, 4:1 hexanes-acetone), the reaction was cooled to RT, filtered and the filtrant washed copiously with EtOAc (ca. 200 mL). The organics were then washed with saturated $NaHCO_3$, $H_2O$, saturated ammonium chloride ($NH_4Cl$) and brine, dried over $MgSO_4$, filtered and concentrated in vacuo. The crude product was then taken up in hexanes (ca. 300 mL), the insolubles filtered off and the filtrate concentrated to yield Compound 24 (6.34 g, 95% yield) as a yellow foam, which was carried forward without further purification.

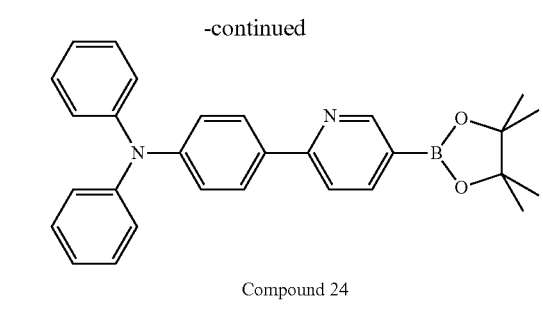

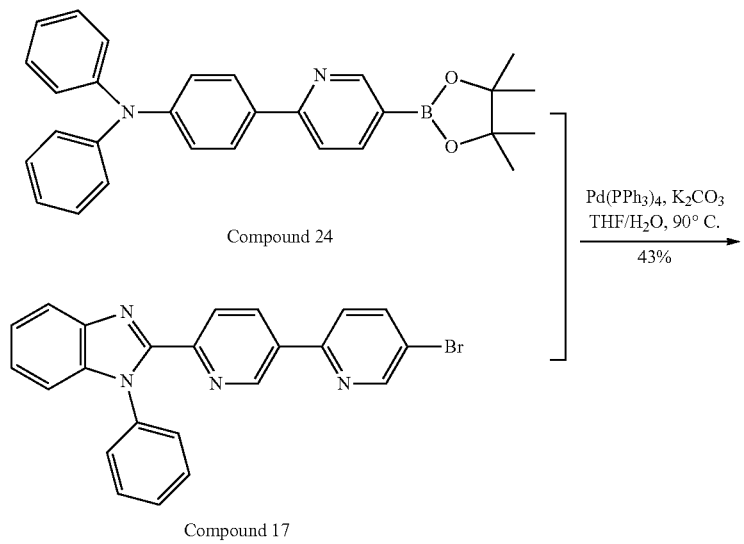

Compound 24

Compound 17

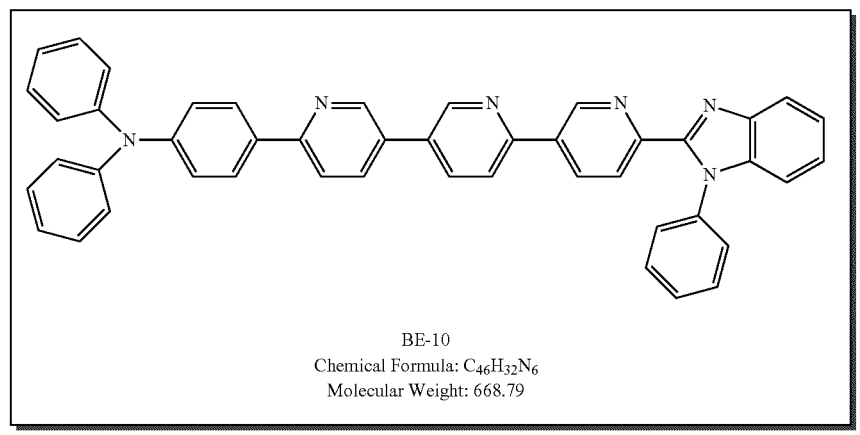

BE-10
Chemical Formula: C$_{46}$H$_{32}$N$_6$
Molecular Weight: 668.79

Compound BE-10

A mixture of N,N-diphenyl-4-(5-(4,4,5,5-tetramethyl-1,3,2-dioxaborolan-2-yl)pyridin-2-yl)aniline (Compound 24) (0.306 g, 0.68 mmol), 2-(5-bromo-[2,3'-bipyridin]-6'-yl)-1-phenyl-1H-benzo[d]imidazole (Compound 17) (0.55 g, 1.3 mmol), Pd(PPh$_3$)$_4$ (0.9 g, 0.078 mmol) and K$_2$CO$_3$ (0.276 g, 2 mmol) in THF/water (30 mL/6 mL) was degassed, and heated at 90° C. for 24 hours. The whole was mixed with dichloromethane/brine, dried over Na$_2$SO$_4$, and purified by flash column (dichloromethane to dichloromethane/ethyl acetate 9:1 to 2:1). The desired yellow emissive fraction was collected, concentrated and filtered to give a yellow solid (Compound BE-10) (0.20 g, in 43% yield). LCMS (APCI+) was calculated for C$_{46}$H$_{33}$N$_6$ (M+H)=669. found: m/e=669.

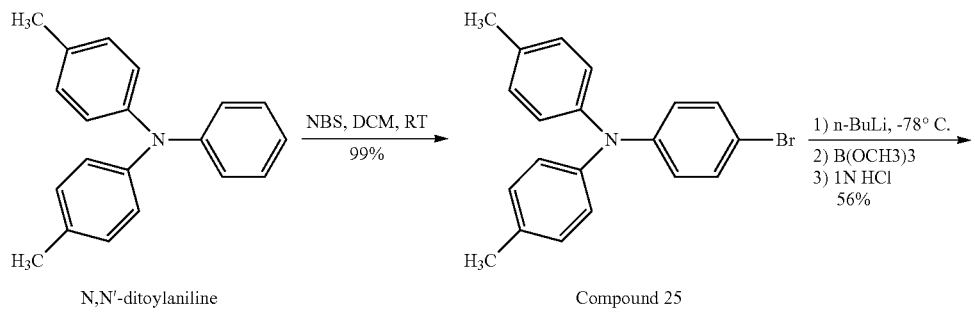

N,N'-ditoylaniline

Compound 25

-continued
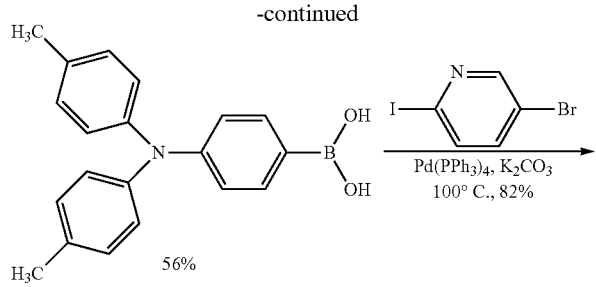
Compound 26, 56%
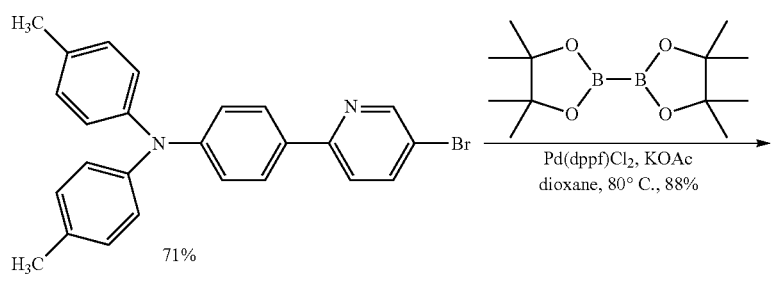
Compound 27, 71%
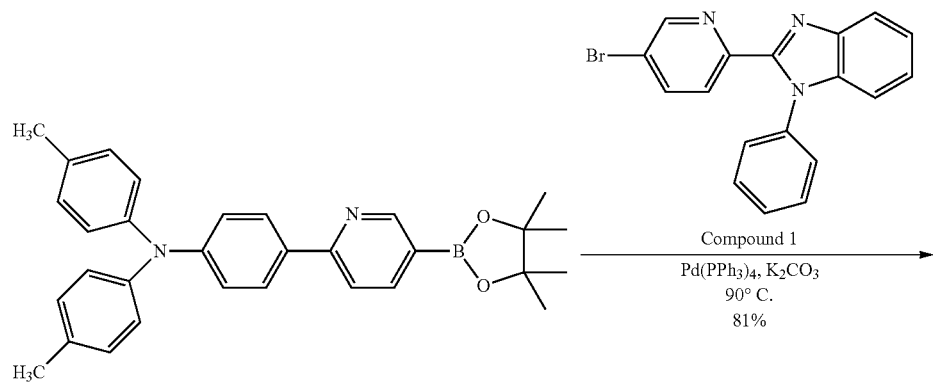
Compound 28
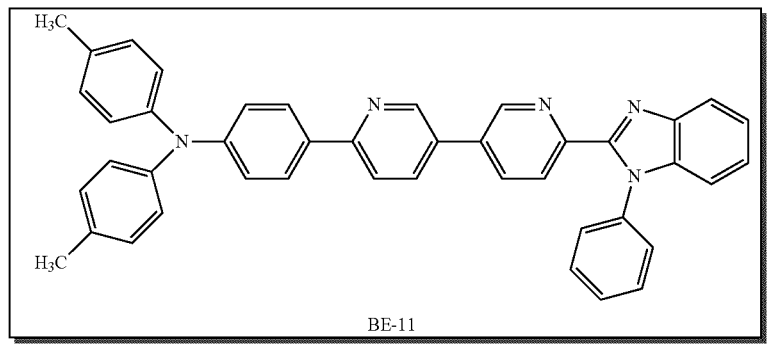
BE-11
Molecular Weight: 619.76

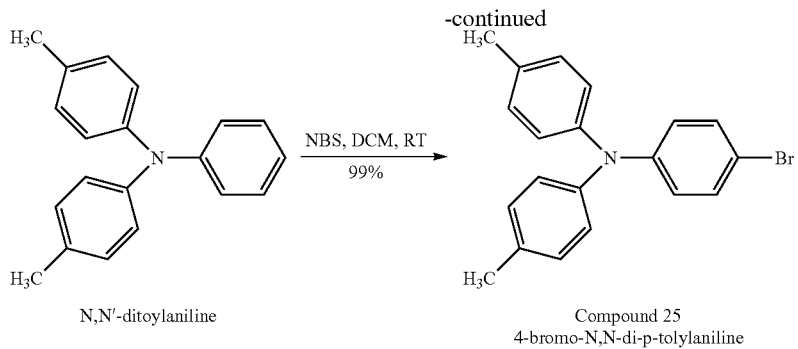

N,N'-ditoylaniline

Compound 25
4-bromo-N,N-di-p-tolylaniline

4-bromo-N,N-di-p-tolylaniline

To a solution of N,N'-ditolylaniline (10 g, 36.6 mmol) in dichloromethane (200 mL) was added n-bromosuccinimide (NBS) (6.764 g, 38 mmol) at RT. The whole was stirred for about 3 hours. After filtering off the solid, the solution was loaded on silica gel, and purified by flash column (hexanes to hexanes dichloromethane 4:1). The desired fraction was collected and a white solid (Compound 25) was obtained after removal of solvents (12.86 g, in 99.7% yield)

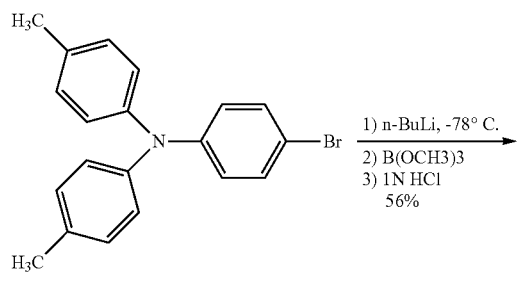

Compound 25

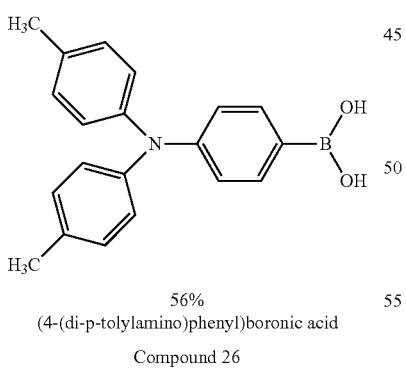

56%
(4-(di-p-tolylamino)phenyl)boronic acid
Compound 26

(4-(di-p-tolylamino)phenyl)boronic acid (Compound 26)

To a solution of 4-bromo-N,N-di-p-tolylaniline (Compound 25) (12.55 g, 35.6 mmol) in anhydrous THF (100 mL), was added n-BuLi solution (16 mL, 2.5 M in hexanes) at −78° C. slowly. The resulting solution was stirred at −78° C. for about one hour. Then a freshly distilled trimethyl borate (B(OCH$_3$)$_3$) (5.6 mL) was added. The solution turned to yellow immediately, and was stirred at RT for about 2 hours. After addition of 1N HCl solution (150 mL), the whole was stirred at RT for about 18 hours and concentrated. The resulting solid was filtered and washed with diethyl ether to give a light yellow solid (Compound 26) (5.8 g, in 56% yield).

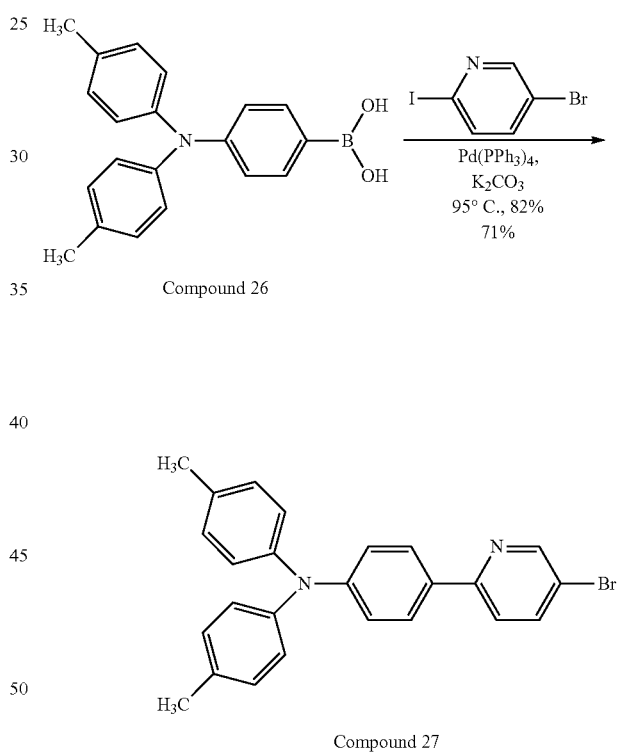

Compound 26

Compound 27

4-(5-bromopyridin-2-yl)-N,N-di-p-tolylaniline (Compound 27)

A mixture of (4-(di-p-tolylamino)phenyl)boronic acid (Compound 26) (3.17 g, 10 mmol), 2-iodo-5-bromo-pyridine (5.68 g, 20 mmol), Pd(PPh$_3$)$_4$ (0.58 g, 0.5 mmol) and K$_2$CO$_3$ (2.76 g, 20 mmol) in dioxane/water (80 mL/15 mL) was degassed and heated at about 95° C. overnight. The resulting solution was diluted with ethyl acetate (200 mL), loaded on silica gel, and purified by flash column (hexanes to hexanes/dichloromethane 9:1 to 4:1 to 3:2). The desired fraction was collected and concentrated to give a light yellow solid (Compound 27) (3.5 g, in 82% yield).

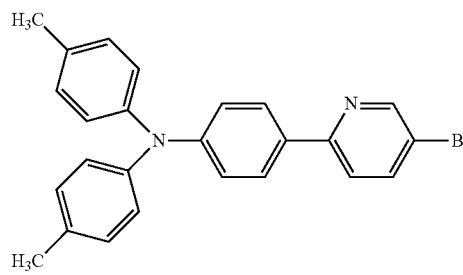

Compound 27

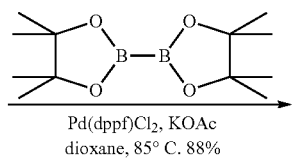

Pd(dppf)Cl₂, KOAc
dioxane, 85° C. 88%

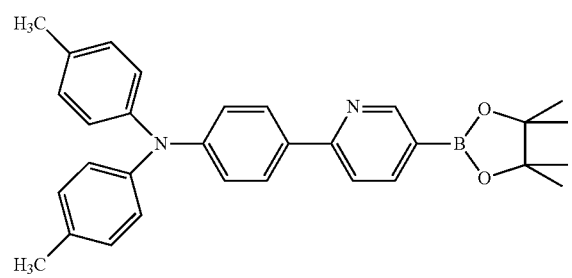

Compound 28

4-methyl-N-(4-(5-(4,4,5,5-tetramethyl-1,3,2-dioxaborolan-2-yl)pyridin-2-yl)phenyl)-N-(p-tolyl)aniline (Compound 28)

A mixture of 4-(5-bromopyridin-2-yl)-N,N-di-p-tolylaniline (Compound 27) (3.44 g, 8 mmol), bis(pinacolate)diborane (2.286 g, 9 mmol), Pd(dppf)Cl₂ (0.365 g, 0.5 mmol) and KOAc (1.96 g, 20 mmol) in dioxane (60 mL) was degassed and heated at about 85° C. overnight. The mixture was diluted with ethyl acetate, and the precipitate filtered off, then loaded on silica gel and purified by flash column (dichloromethane to dichloromethane/ethyl acetate 9:1 to 2:1). The desired fraction was collected and a yellow solid (Compound 28) was obtained after removal of solvents (3.34 g, in 88% yield).

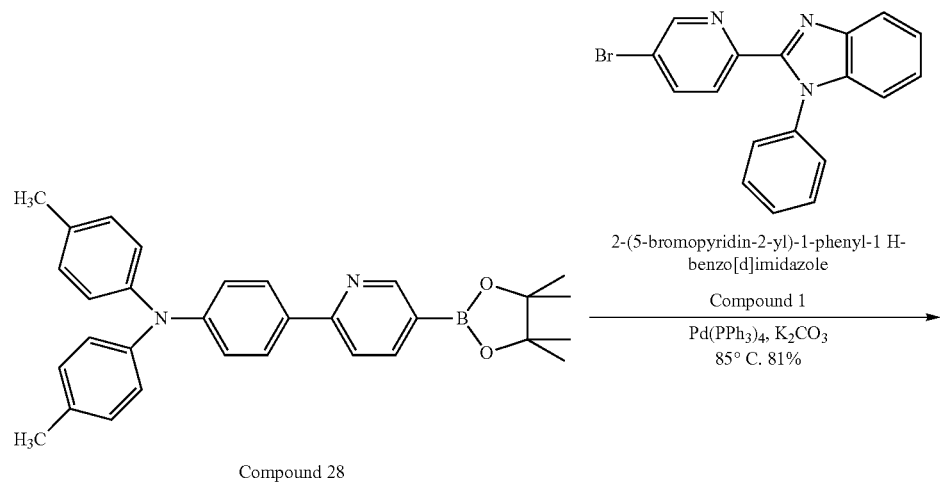

Compound 28

2-(5-bromopyridin-2-yl)-1-phenyl-1 H-benzo[d]imidazole

Compound 1

Pd(PPh₃)₄, K₂CO₃
85° C. 81%

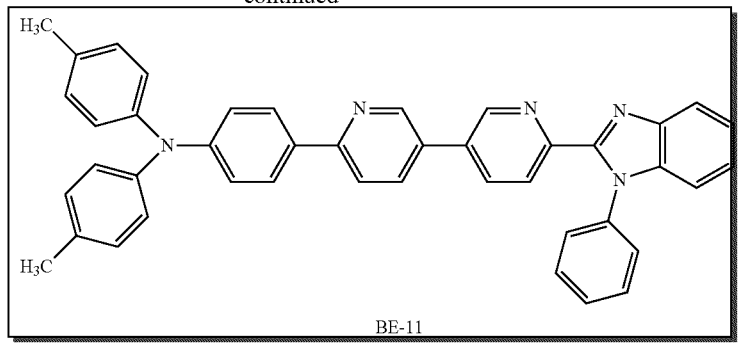

BE-11

Chemical Formula: C$_{43}$H$_{33}$N$_5$
Molecular Weight: 619.76

Compound BE-11

A mixture of 4-methyl-N-(4-(5-(4,4,5,5-tetramethyl-1,3,2-dioxaborolan-2-yl)pyridin-2-yl)phenyl)-N-(p-tolyl)aniline (Compound 28) (1.7 g, 3.57 mmol), 2-(5-bromopyridin-2-yl)-1-phenyl-1H-benzo[d]imidazole (Compound 1) (1.25 g, 3.57 mmol), Pd(PPh$_3$)$_4$ (0.2 g, 0.18 mmol) and K$_2$CO$_3$ (1.1 g, 8 mmol) in dioxane/water (80 mL/15 mL) was degassed and heated at 85° C. overnight. The resulting yellow precipitate was filtered and collected, then purified by flash column (dichloromethane to dichloromethane/ethyl acetate 9:1 to 4:1). The desired fraction was collected and concentrated. A bright yellow solid (Compound BE-11) was obtained (1.8 g, in 81% yield). LCMS (APCI+) was calculated for C$_{43}$H$_{34}$N$_5$ (M+H)=620. found: m/e=620.

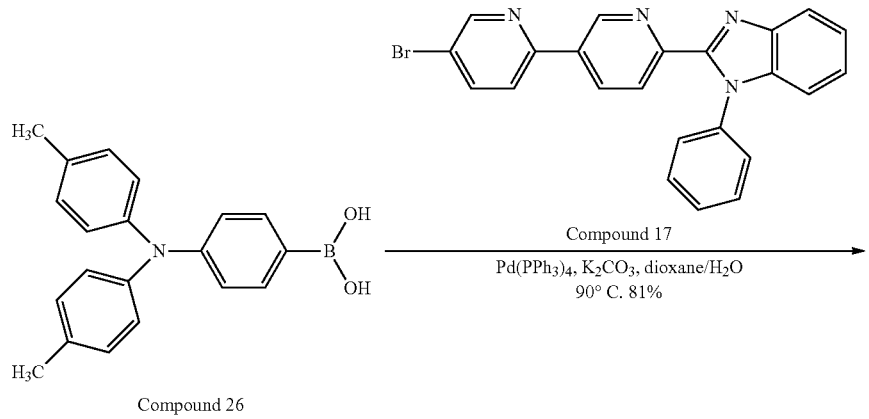

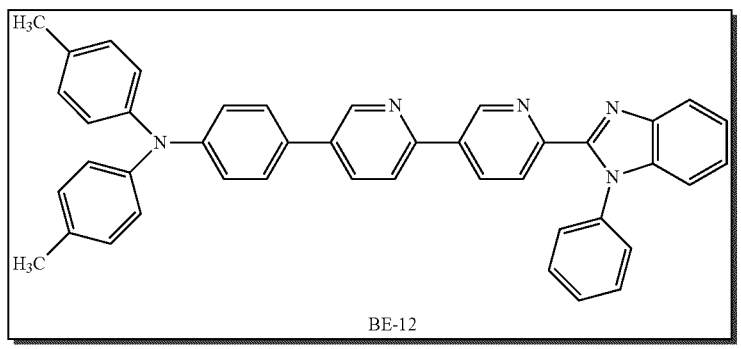

BE-12

Chemical Formula: C$_{43}$H$_{33}$N$_5$
Molecular Weight: 619.76

Compound BE-12

A mixture of (4-(di-p-tolylamino)phenyl)boronic acid (Compound 26) (0.76 g, 2.4 mmol), 2-(5-bromo-[2,3'-bipyridin]-6'-yl)-1-phenyl-1H-benzo[d]imidazole (Compound 17) (2.05 g, 4.8 mmol), Pd(PPh$_3$)$_4$ (0.138 g, 0.12 mmol) and K$_2$CO$_3$ (0.69 g, 5 mmol) in dioxane/water (50 mL/9 mL) was degassed and heated at about 90° C. for about 6 hours. The whole was poured into dichloromethane (150 mL), then washed with brine, dried over Na$_2$SO$_4$, loaded on silica gel and purified by flash column (hexanes/dichloromethane 1:1 to dichloromethane to dichloromethane/ethyl acetate 9:1 to 4:1). The desired fraction was collected and concentrated to give a yellow solid (Compound BE-12) (1.20 g, in 81% yield). LCMS (APCI+) was calculated for C$_{43}$H$_{34}$N$_5$ (M+H)= 620. found: m/e=620.

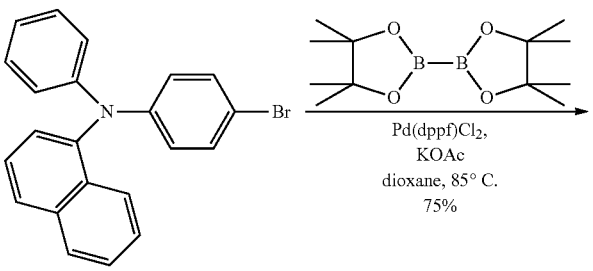

N-(4-bromophenyl)-N-phenylnaphthalen-1-amine

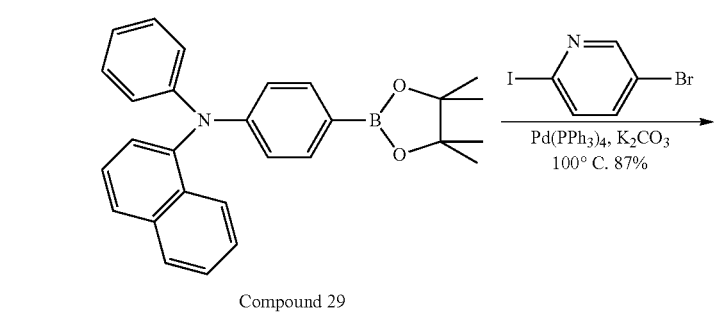

Compound 29

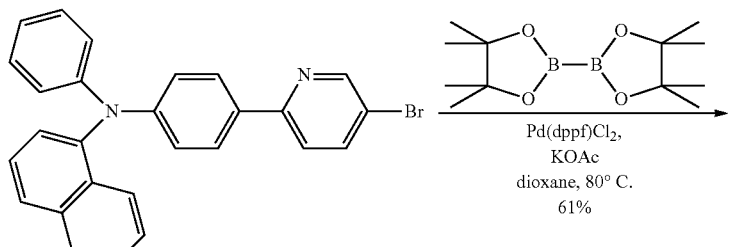

Compound 30

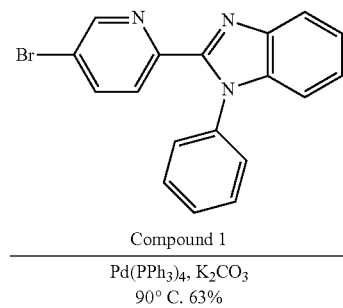

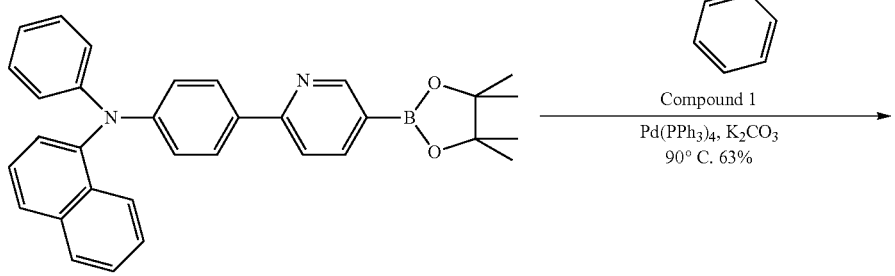

Compound 31

-continued

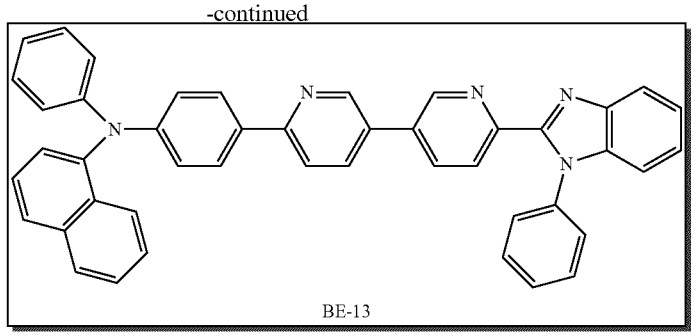

BE-13

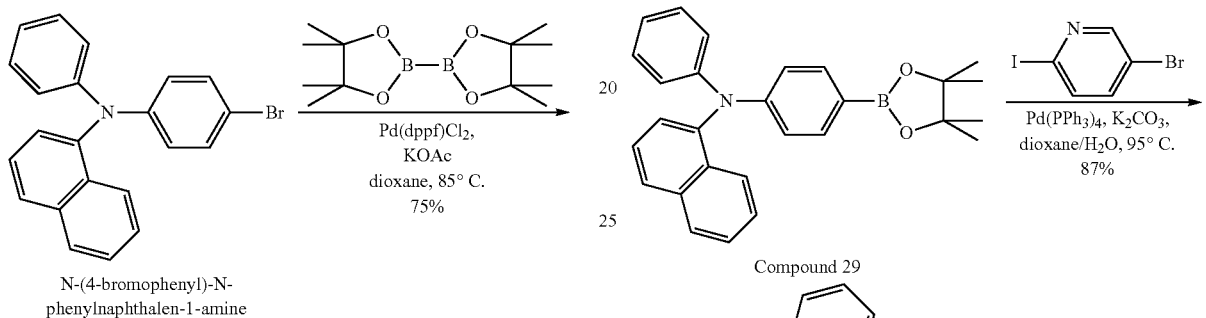

N-(4-bromophenyl)-N-phenylnaphthalen-1-amine

Compound 29

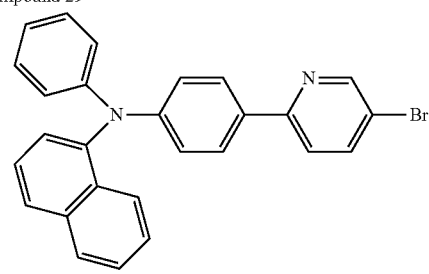

Compound 30

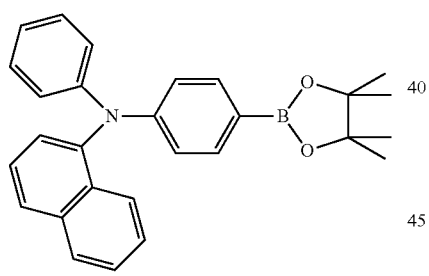

Compound 29

N-phenyl-N-(4-(4,4,5,5-tetramethyl-1,3,2-dioxaborolan-2-yl)phenyl)naphthalen-1-amine (Compound 29)

A mixture of N-(4-bromophenyl)-N-phenylnaphthalen-1-amine (7.14 g, 19.1 mmol), bis(pinacolate)diborane (5.08 g, 20 mmol), Pd(dppf)Cl$_2$ (0.73 g, 1.0 mmol) and KOAc (4.9 g, 50 mmol) in dioxane (100 mL) was degassed and heated at about 85° C. for about 15 hours. The resulting mixture was poured into ethyl acetate (250 mL), then the precipitate was filtered off. The solution was loaded on silica gel, and purified by flash column (hexanes to hexanes/dichloromethane 8:1 to 6:1 to 2:1). The desired fraction was collected, and concentrated. A white solid (Compound 29) was obtained after removal of solvent (6.0 g, in 75% yield).

N-(4-(5-bromopyridin-2-yl)phenyl)-N-phenylnaphthalen-1-amine (Compound 30)

A mixture of N-phenyl-N-(4-(4,4,5,5-tetramethyl-1,3,2-dioxaborolan-2-yl)phenyl)naphthalen-1-amine (Compound 29) (2.32 g, 5.51 mmol), 2-iodo-5-bromo-pyridine (3.13 g, 11 mmol), Pd(PPh$_3$)$_4$ (0.346 g, 0.3 mmol) and K$_2$CO$_3$ (1.38 g, 10 mmol) in dioxane/water (60 mL/10 mL) was degassed and heated at about 95° C. overnight. The resulting mixture was mixed with ethyl acetate/brine, dried over Na$_2$SO$_4$, loaded on silica gel, and purified by flash column (hexanes to hexanes/dichloromethane 9:1 to 3:1). The desired fraction was collected and a light yellow solid (Compound 30) was obtained after removal of solvents (2.17 g, in 87% yield).

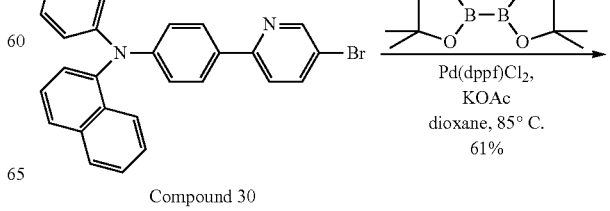

Compound 30

-continued

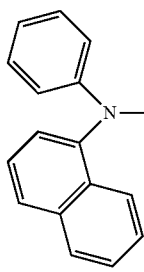

Compound 31

N-phenyl-N-(4-(5-(4,4,5,5-tetramethyl-1,3,2-dioxaborolan-2-yl)pyridin-2-yl)phenyl)naphthalen-1-amine

N-phenyl-N-(4-(5-(4,4,5,5-tetramethyl-1,3,2-dioxaborolan-2-yl)pyridin-2-yl)phenyl)naphthalen-1-amine (Compound 31)

A mixture of N-(4-(5-bromopyridin-2-yl)phenyl)-N-phenylnaphthalen-1-amine (Compound 30) (2.21 g, 4.91 mmol), bis(pinacolate)diborane (1.27 g, 5 mmol), Pd(dppf)Cl$_2$ (0.18 g, 0.25 mmol) and KOAc (0.98 g, 10 mmol) in dioxane (50 mL) was degassed and heated at about 85° C. overnight. The resulting mixture was diluted with ethyl acetate (200 mL). After filtering off the precipitate, the solution was loaded on silica gel, and purified by flash column (dichloromethane to dichloromethane/ethyl acetate 4:1 to 1:1). After removal of solvent, a yellow solid (Compound 31) was obtained (1.5 g, in 61% yield).

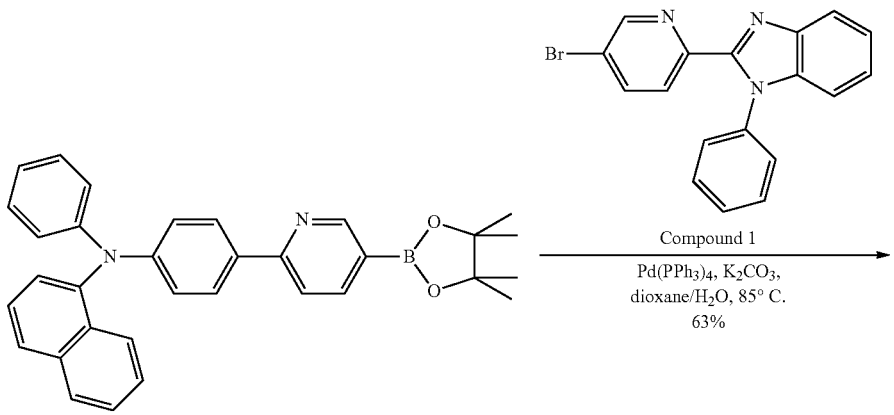

Compound 31

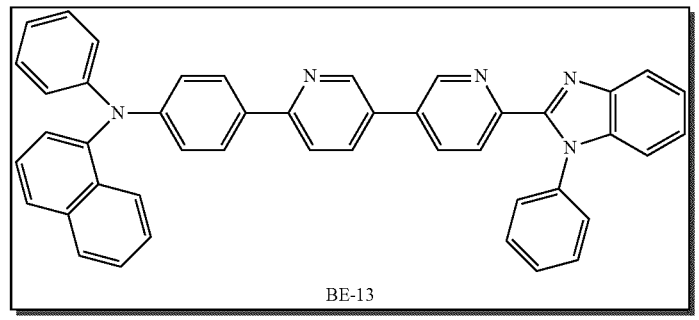

BE-13

Chemical Formula: C$_{45}$H$_{31}$N$_5$
Molecular Weight: 641.76

Compound BE-13

A mixture of N-phenyl-N-(4-(5-(4,4,5,5-tetramethyl-1,3,2-dioxaborolan-2-yl)pyridin-2-yl)phenyl)naphthalen-1-amine (Compound 31) (1.3 g, 2.6 mmol), 2-(5-bromopyridin-2-yl)-1-phenyl-1H-benzo[d]imidazole (Compound 1) (0.91 g, 2.6 mmol), Pd(PPh$_3$)$_4$ (0.23 g, 0.2 mmol) and K$_2$CO$_3$ (0.69 g, 5 mmol) in dioxane/water (50 mL/8 mL) was degassed and heated at about 85° C. for about 5 hours. The resulting mixture was mixed with ethyl acetate (200 mL) and brine. The organic phase was dried over Na$_2$SO$_4$, loaded on silica gel, and purified by flash column (dichloromethane to dichloromethane/ethyl acetate 9:1 to 4:1). The desired fraction was collected and solvent was removed under reduced pressure. The resulting solid was recrystallized in dichloromethane/hexanes to give the desired product (Compound BE-13) (1.05 g, in 63% yield). LCMS (APCI+) was calculated for C$_{45}$H$_{32}$N$_5$ (M+H)=642. found: m/e=642.

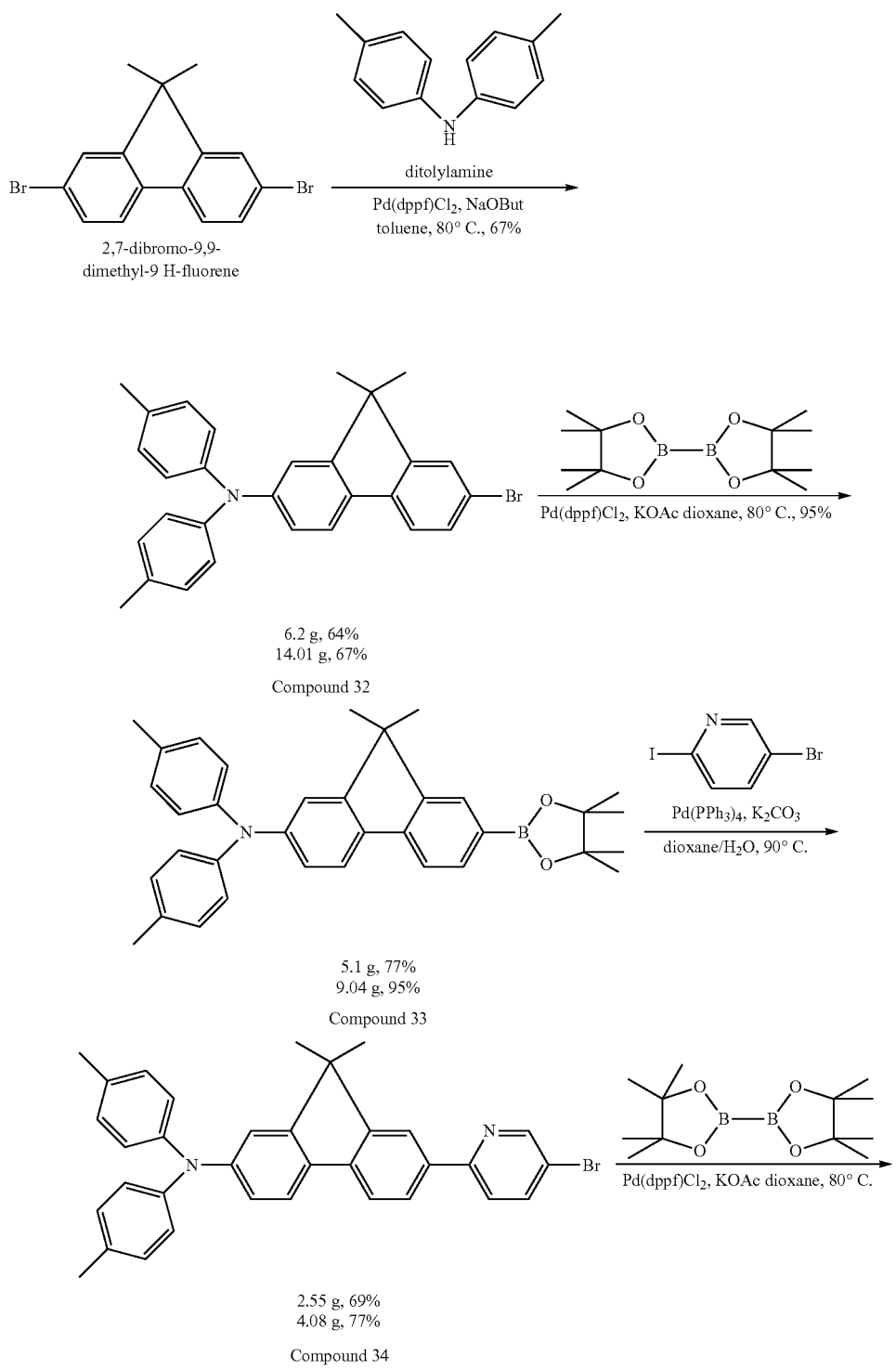

-continued

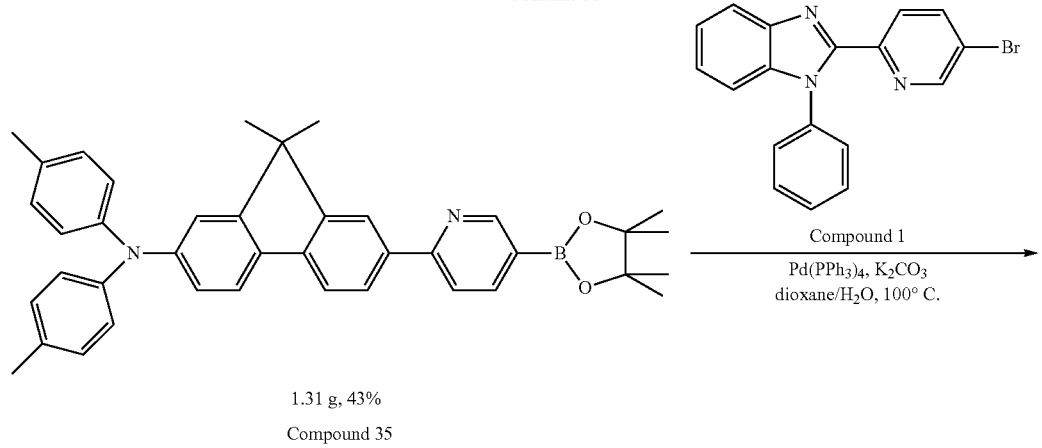

1.31 g, 43%
Compound 35

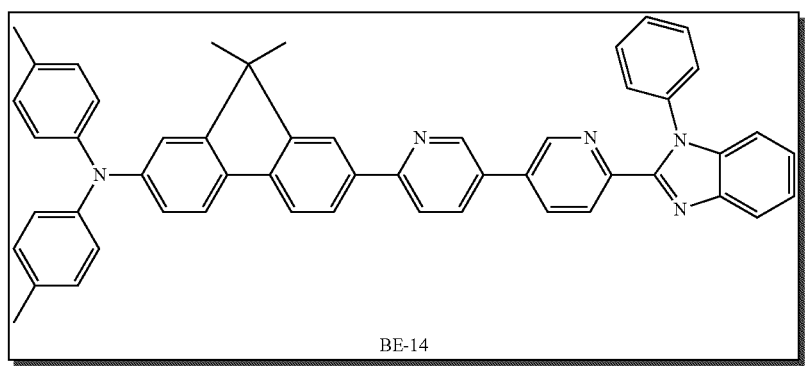

BE-14

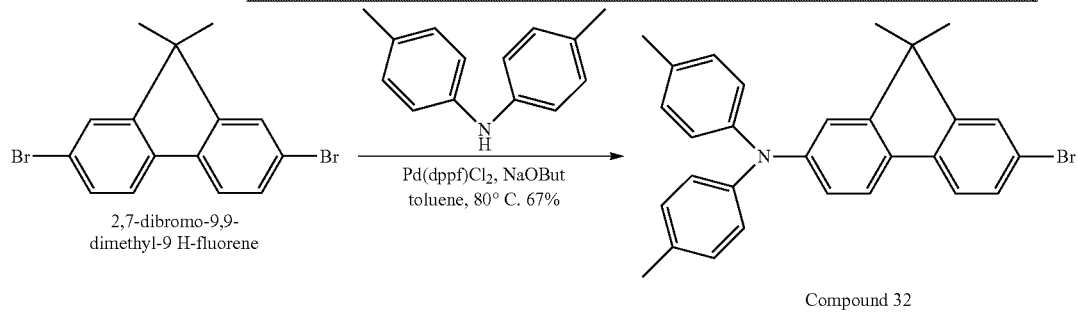

Compound 32

7-bromo-9,9-dimethyl-N,N-di-p-tolyl-9H-fluoren-2-amine (Compound 32)

A mixture of 2,7-dibromo-9,9-dimethyl-9H-fluorene (31.64 g, 89.87 mmol), ditolylamine (8.865 g, 44.9 mmol), Pd(dppf)Cl$_2$ (1.644 g, 2.25 mmol) and sodium tert-butoxide (10.796 g, 112.3 mmol) in toluene 400 mL was degassed and heated at about 80° C. overnight. The resulting mixture was poured into ethyl acetate (500 mL). After the precipitate was filtered off, the solution was washed with water and brine, dried over Na$_2$SO$_4$, loaded on silica gel and purified by flash column (hexane to hexanes/dichloromethane 99:1 to 95:5 gradients). After removal of solvent and recrystallization in dichloromethane/hexanes, a white solid (Compound 32) was obtained (14.0169 g, in 66.6% yield).

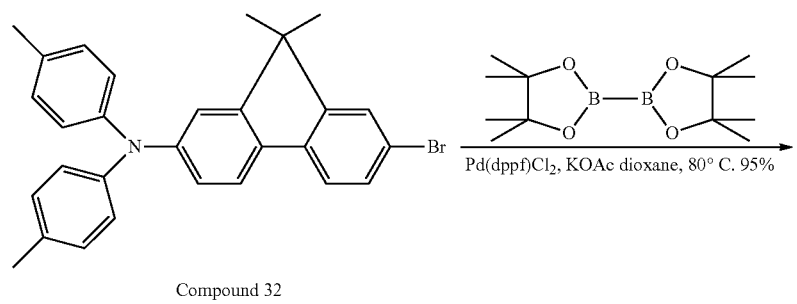

Compound 32

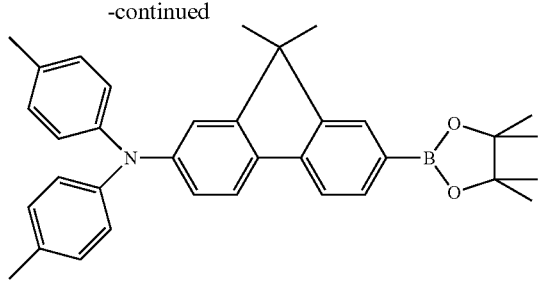

Compound 33

9,9-dimethyl-7-(4,4,5,5-tetramethyl-1,3,2-dioxaborolan-2-yl)-N,N-di-p-tolyl-9H-fluoren-2-amine (Compound 33)

A mixture of 7-bromo-9,9-dimethyl-N,N-di-p-tolyl-9H-fluoren-2-amine (Compound 32) (9.0 g, 19.21 mmol), bis(pinacolate)diborane (5.367 g, 21.13 mmol), Pd(dppf)Cl$_2$ (0.984 g, 1.34 mmol) and potassium acetate (8.485 g, 86.46 mmol) in dioxane (120 mL) was degassed an heated at about 80° C. overnight. The whole was poured into ethyl acetate (300 mL), then washed with water and brine. The organic phase was dried over MgSO$_4$, loaded on silica gel, and purified by flash column (ethyl acetate/hexanes 1:5 to 1:1 to ethyl acetate). The desired fraction was collected, concentrated and recrystallized in dichloromethane/hexanes to give a white solid (Compound 33) (9.452 g, in 95.4% yield).

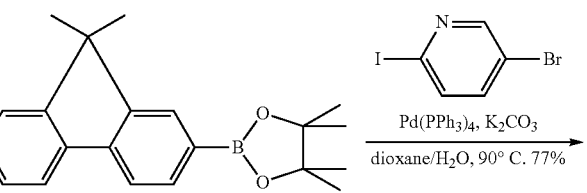

Compound 33

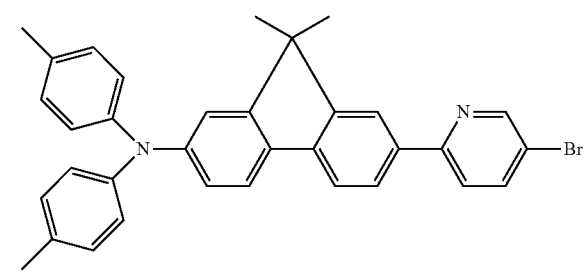

Compound 34

7-(5-bromopyridin-2-yl)-9,9-dimethyl-N,N-di-p-tolyl-9H-fluoren-2-amine (Compound 34)

A mixture of 9,9-dimethyl-7-(4,4,5,5-tetramethyl-1,3,2-dioxaborolan-2-yl)-N,N-di-p-tolyl-9H-fluoren-2-amine (Compound 33) (5.0 g, 9.7 mmol), 2-iodo-5-bromo-pyridine (8.26 g, 29.1 mmol), Pd(PPh$_3$)$_4$ (0.56 g, 0.48 mmol) and K$_2$CO$_3$ (5.36 g, 38.8 mmol) in dioxane/water (65 mL/13 mL) was degassed and heated at about 90° C. overnight. The resulting mixture was worked up with ethyl acetate and brine. The organic phase was dried over Na$_2$SO$_4$, loaded on silica gel, purified by flash column (hexanes/dichloromethane 5:1 to 1:3 to dichloromethane). The desired fraction was collected, concentrated and recrystallized in dichloromethane/hexanes to give a white solid (Compound 34) (4.085 g, in 77% yield).

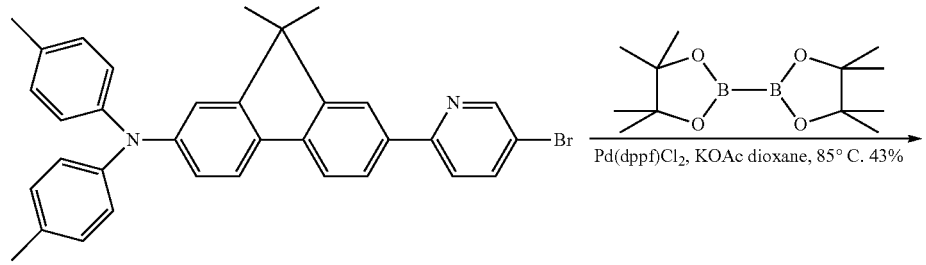

Compound 34

9,9-dimethyl-7-(5-(4,4,5,5-tetramethyl-1,3,2-dioxaborolan-2-yl)pyridin-2-yl)-N,N-di-p-tolyl-9H-fluoren-2-amine (Compound 35)

A mixture of 7-(5-bromopyridin-2-yl)-9,9-dimethyl-N,N-di-p-tolyl-9H-fluoren-2-amine (Compound 34) (2.00 g, 3.67 mmol), bis(pinacolate)diborane (1.024 g, 4.03 mmol), Pd(dppf)Cl$_2$ (0.188 g, 0.26 mmol) and KOAc (1.619 g, 16.5 mmol) in dioxane (25 mL) was degassed and heated at about 85° C. overnight. The resulting mixture was mixed with ethyl acetate/brine. The organic phase was dried over Na$_2$SO$_4$, loaded on silica gel, and purified by flash column (dichloromethane to dichloromethane ethyl acetate 9:1 to 1:1 to ethyl acetate). After removal of solvents, a white solid (Compound 35) was obtained (1.305 g, in 43% yield).

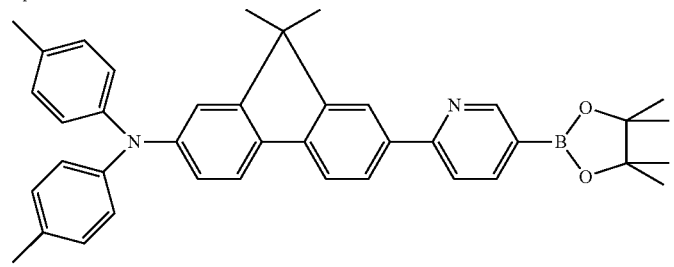

Compound 35

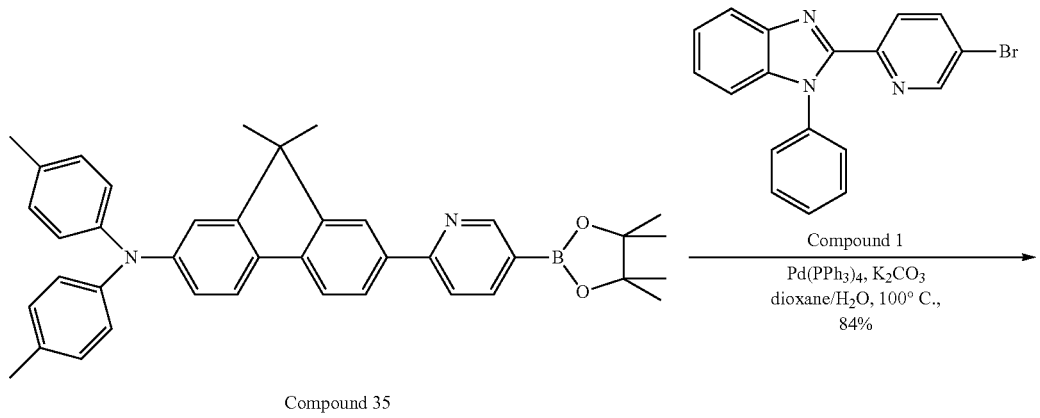

Compound 35

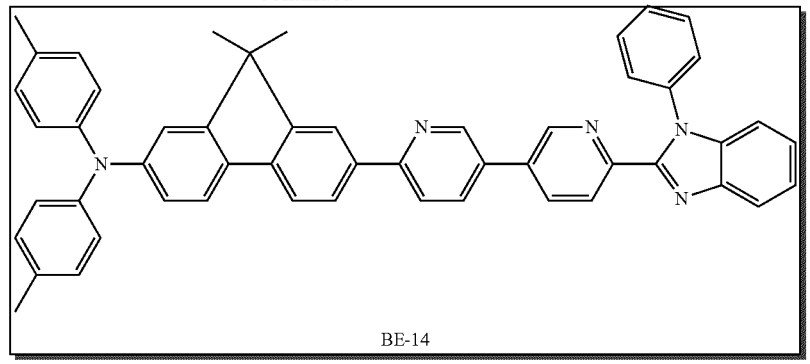

BE-14

Chemical Formula: $C_{52}H_{41}N_5$
Molecular Weight: 735.92

Compound BE-14

A mixture of 9,9-dimethyl-7-(5-(4,4,5,5-tetramethyl-1,3,2-dioxaborolan-2-yl)pyridin-2-yl)-N,N-di-p-tolyl-9H-fluoren-2-amine (Compound 35) (1.3 g, 2.19 mmol), 2-(5-bromopyridin-2-yl)-1-phenyl-1H-benzo[d]imidazole (Compound 1) (0.845 g, 2.41 mmol), $Pd(PPh_3)_4$ (0.127 g, 0.11 mmol) and $K_2CO_3$ (1.364 g, 9.87 mmol) in dioxane/water (25 mL/5 mL) was degassed and heated at about 100° C. overnight. The product precipitated after being cooled to RT. The precipitate was filtered and washed with water, methanol, and then dried. The resulting solid was dissolved in dichloromethane and purified by flash column (hexanes/ethyl acetate 3:2 to ethyl acetate). The desired fraction was collected, concentrated and recrystallized in dichloromethane/hexanes to give a light yellow solid (Compound BE-14) (1.356 g, in 84% yield). LCMS (APCI+) was calculated for $C_{52}H_{42}N_5$ (M+H)=736. found: m/e=736.

Example 2

Example of OLED Device Configuration and Performance; Fabrication of a Hybrid White Light-Emitting Device ITO coated glass substrates are cleaned by ultrasound consecutively in water, acetone, and 2-propanol, baked at 110° C. for 3 hours, followed by treatment with oxygen plasma for 5 min. A layer of PEDOT:PSS (Baytron P, purchased from H.C. Starck) is spin-coated at 3000 rpm onto the pre-cleaned and $O_2$-plasma treated ITO substrate and annealed at 180° C. for 30 min., to yield a thickness of around 55 nm. In a glove-box hosted vacuum deposition system at a pressure of $10^{-7}$ torr (1 torr=133.322 Pa), DTASi is first deposited on top of a PEDOT/PSS layer at deposition rate of 0.06 nm/s., yielding a 30 nm thick film. Then the Compound BE-2 is heated and deposited on top of DTASi, yielding a film about 5 nm thick, followed by co-deposition of Compound BE-2 and Ir(PIQ)2(acac) at depositions rates of about 0.06 nm/s. to form a 5 nm thick layer, and deposition of another Compound BE-2 layer having a thickness of about 5 nm. Then 1,3,5-tris(N-phenyl-benzimidizol-2-yl)benzene (TPBI) at a deposition rate of about 0.06 nm/s. is deposited on the Ir; $(PIQ)_2(acac)$/BE-2 layer to form a 40 nm thick film. LiF (1.0 nm) and Al (100 nm) are then deposited successively at deposition rates of 0.005 and 0.2 nm/s., respectively. Each individual device has an area of 0.14 $cm^2$.

Example 3

Device A

Figure 2:
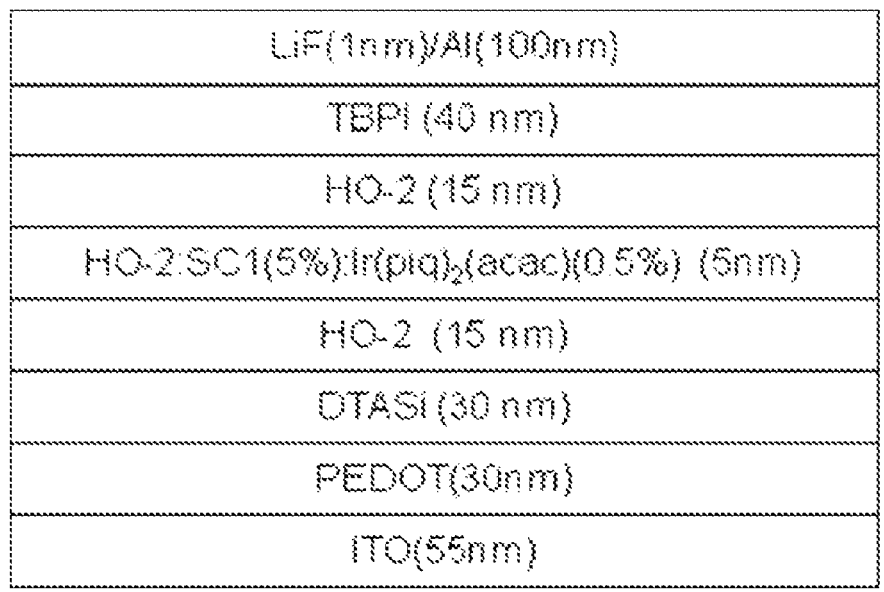
FIG. 2 is a schematic drawing of an embodiment of an OLED device described in Example 1.

All spectra are measured with an Ocean Optics HR 4000 spectrometer, and I-V-L characteristics are taken with a Keithley 2400 SourceMeter, Newport 2832-C power meter and 818 UV detector. All device operations are performed inside a nitrogen-filled glove-box. An example of a configuration of the device thus described (Device A) is shown in FIG. 2.

Upon determining the luminescent efficiency and power efficiency as a function of luminance of Device A, a plot of the electroluminescence spectrum of Device A, and the CRI of Device A, Compound BE-2 is suitable as a host material in hybrid OLED devices.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A compound represented by a formula:

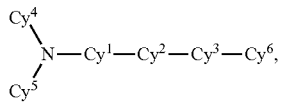

wherein $Cy^1$ is unsubstituted p-phenylene or p-phenylene having 1 methyl substituent;

$Cy^2$ is unsubstituted p-phenylene or p-phenylene having 1 methyl substituent;

$Cy^{3a}$ is unsubstituted p-pyridinylene or p-pyridinylene having 1 methyl substituent;

$Cy^{3b}$ is unsubstituted p-pyridinylene or p-pyridinylene having 1 methyl substituent;

$Cy^4$ and $Cy^5$ are independently unsubstituted phenyl or phenyl having 1 methyl substituent or unsubstituted naphthyl or naphthyl having 1 methyl substituent; and, $Cy^6$ is unsubstituted benzimidazol-2-yl or benzimidazol-2-yl having 1 methyl substituent.

2. The compound of claim 1, further represented by a formula:

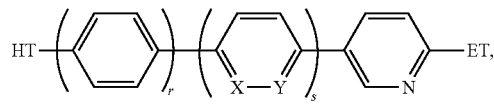

wherein HT is unsubstituted diphenylamine or diphenylamine having 1 methyl substituent or unsubstituted phenylnaphthylamine or phenylnaphthylamine having 1 methyl substituent;

ET is unsubstituted benzimidazol-2-yl or benzimidazol-2-yl having 1 methyl substituent and/or a phenyl group;

X is CH or N;

Y is CH or N, provided that when X is N, Y is CH and when Y is N, X is CH, and provided that when X is CH, Y is N and when Y is CH, X is N;

r is 2; and, s is 1.

3. The compound of claim 2, wherein HT is

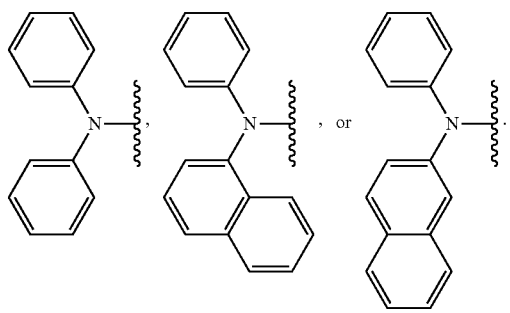

4. The compound of claim 2, wherein ET is

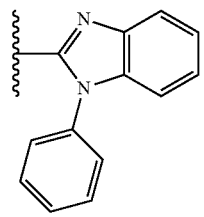 [SMILES: *c1nc2ccccc2n1-c1ccccc1]

5. The compound of claim 1, wherein $Cy^1$ and $Cy^2$ are unsubstituted.

6. The compound of claim 1, wherein $Cy^2$ and $Cy^3$ are unsubstituted.

7. The compound of claim 1, wherein $Cy^1$ and $Cy^3$ are unsubstituted.

8. The compound of claim 1, wherein $Cy^1$, $Cy^2$ and $Cy^3$ are unsubstituted.

9. The compound of claim 1, wherein the compound is:

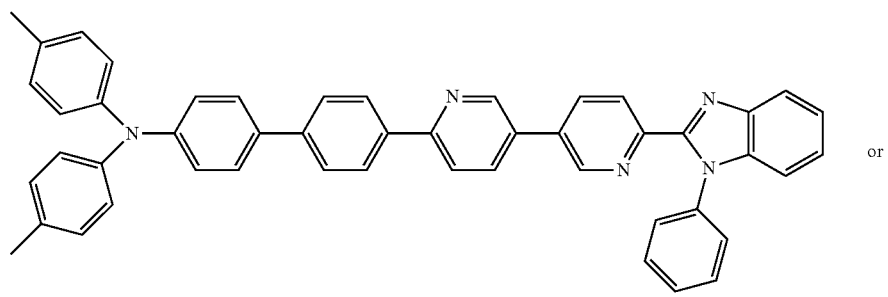

or

-continued
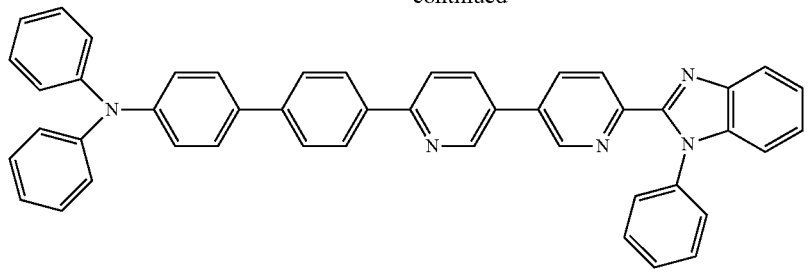
10. The compound of claim 1, wherein the compound is:
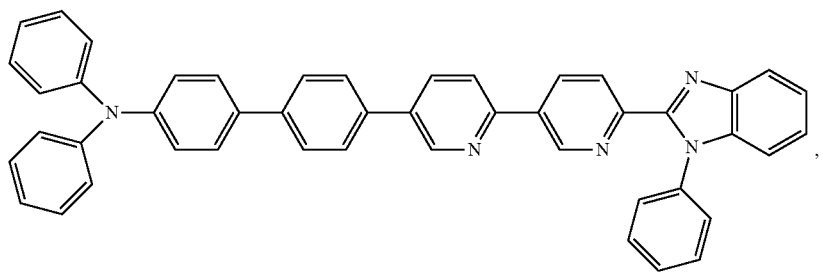,
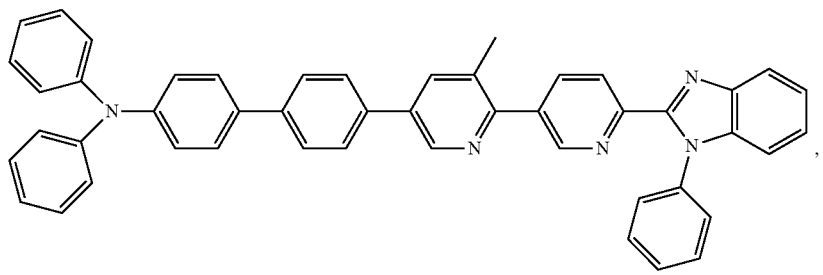,
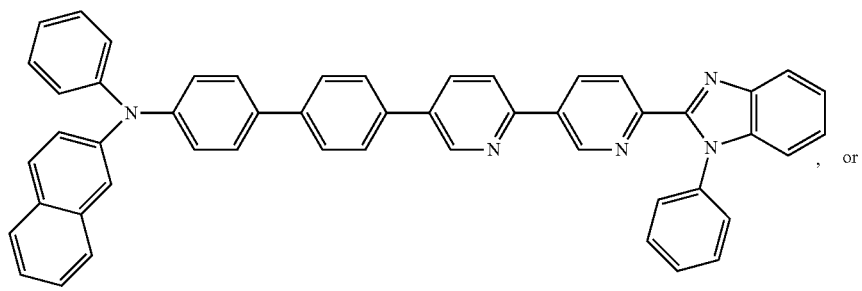, or
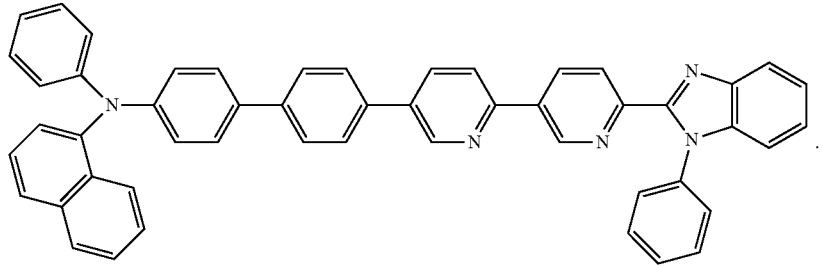.

11. A compound of claim 1, further represented by a formula:

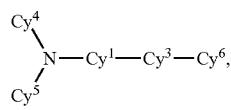

wherein Cy¹ and Cy² are each unsubstituted p-phenylene or p-phenylene having 1 methyl substituent on one or both Cy¹ and Cy²;

Cy³ is unsubstituted 2,3'-bipyridinyl or 2,3'-bipyridinyl having 1 methyl substituent, or unsubstituted 3,3'-bi-pyridinyl or 3,3'-bi-pyridinyl having 1 methyl substituent;

Cy⁴ and Cy⁵ are unsubstituted phenyl or phenyl having 1 methyl substituent on one or both Cy⁴ and Cy⁵ or unsubstituted naphthyl or naphthyl having 1 methyl substituent on one or both Cy⁴ and Cy⁵; and, Cy⁶ is unsubstituted 1-phenyl-1H-benzo[d]imidazol-2-yl or 1-phenyl-1H-benzo[d]imidazol-2-yl having 1 methyl substituent.

12. A compound having a structure:

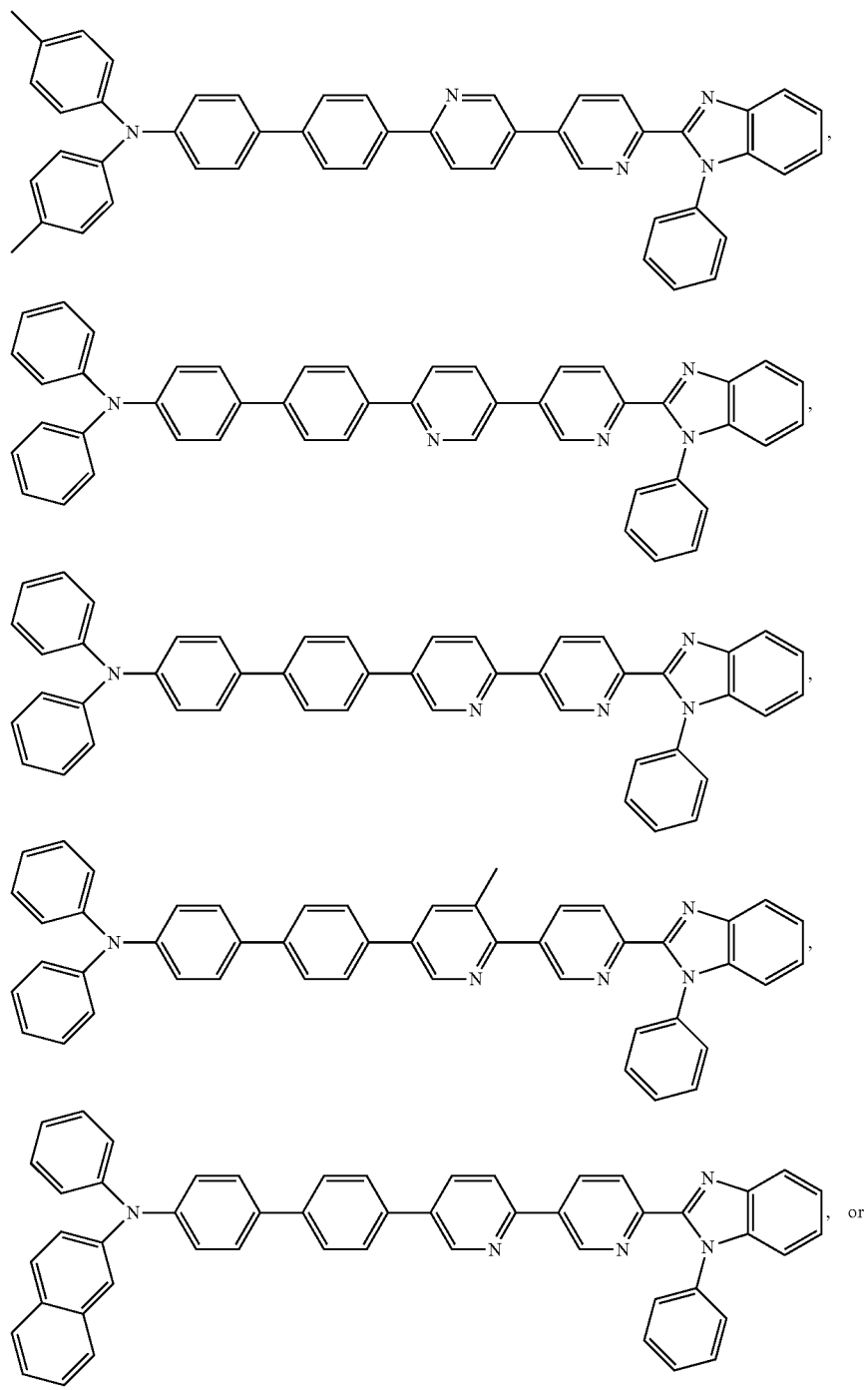

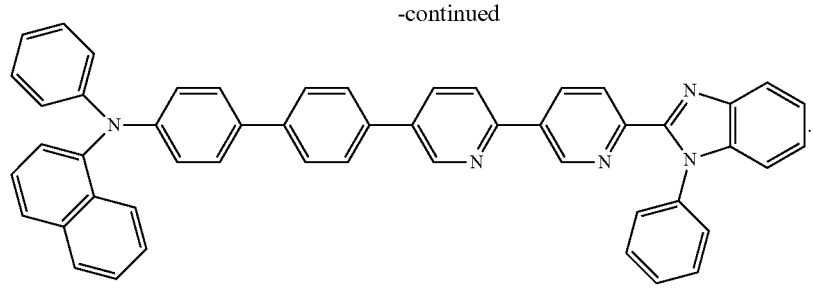
* * * * *